(12) United States Patent
Julian

(10) Patent No.: US 11,864,842 B2
(45) Date of Patent: Jan. 9, 2024

(54) DEVICES, SYSTEMS, AND METHODS FOR MANUALLY AND ROBOTICALLY DRIVING MEDICAL INSTRUMENTS

(71) Applicant: Auris Health, Inc., Redwood City, CA (US)

(72) Inventor: Christopher Allen Julian, Los Gatos, CA (US)

(73) Assignee: Auris Health, Inc., Redwood City, CA (US)

(*) Notice: Subject to any disclaimer, the term of this patent is extended or adjusted under 35 U.S.C. 154(b) by 506 days.

(21) Appl. No.: 17/080,408

(22) Filed: Oct. 26, 2020

(65) Prior Publication Data

US 2021/0121240 A1 Apr. 29, 2021

Related U.S. Application Data

(63) Continuation of application No. 16/583,653, filed on Sep. 26, 2019, now Pat. No. 10,820,947.

(Continued)

(51) Int. Cl.
*A61B 34/20* (2016.01)
*A61B 34/00* (2016.01)
(Continued)

(52) U.S. Cl.
CPC .............. *A61B 34/20* (2016.02); *A61B 34/32* (2016.02); *A61B 34/74* (2016.02);
(Continued)

(58) Field of Classification Search
CPC ......... A61B 34/20; A61B 34/32; A61B 34/74; A61B 2034/2051; A61B 2034/2057;
(Continued)

(56) References Cited

U.S. PATENT DOCUMENTS 2,556,601 A 6/1951 Schofield
2,566,183 A 8/1951 Forss
(Continued)

FOREIGN PATENT DOCUMENTS

CN 101161426 4/2008
CN 103037799 4/2011
(Continued)

OTHER PUBLICATIONS

European Search Report for Appl. No. 19866441.9, dated May 25, 2022, 11 pages.

(Continued)

*Primary Examiner* — Richard G Louis
(74) *Attorney, Agent, or Firm* — Chang & Hale LLP

(57) ABSTRACT

Certain aspects relate to systems and techniques for manually and robotically driving a medical instrument. For example, a system can include a handle configured to receive an elongated shaft of a medical instrument. The handle can include a gripping mechanism for selectively engaging the elongated shaft, and an articulation input and configured for receiving user inputs of commanded articulation of the elongated shaft. The system can include an instrument drive mechanism configured to engage a base of the medical instrument. The instrument drive mechanism can include at least one robotic drive output configured to engage a robotic drive input of the base to cause articulation of the elongated shaft based on the user inputs received at the articulation input, and a first connector configured to removably couple the instrument drive mechanism to an instrument positioning device.

19 Claims, 35 Drawing Sheets

Related U.S. Application Data

(60) Provisional application No. 62/738,436, filed on Sep. 28, 2018.

(51) Int. Cl.
*A61B 34/32* (2016.01)
*A61B 34/30* (2016.01)

(52) U.S. Cl.
CPC .............. *A61B 2034/2051* (2016.02); *A61B 2034/2057* (2016.02); *A61B 2034/2074* (2016.02); *A61B 2034/301* (2016.02); *A61B 2034/305* (2016.02); *A61B 2034/742* (2016.02)

(58) Field of Classification Search
CPC ...... A61B 2034/2074; A61B 2034/301; A61B 2034/305; A61B 2034/742; A61B 2017/00477; A61B 34/37; A61B 34/25; A61B 2017/00809; A61B 2017/00818; A61B 2034/105; A61B 2034/2059; A61B 2034/2061; A61B 2034/2065; A61B 2090/306; A61B 2090/309; A61B 2090/3614; A61B 2090/376; A61G 13/04; A61G 13/1295

See application file for complete search history.

(56) References Cited

U.S. PATENT DOCUMENTS

| | | |
|---|---|---|
| 2,623,175 A | 12/1952 | Finke |
| 2,730,699 A | 1/1956 | Gratian |
| 2,884,808 A | 5/1959 | Mueller |
| 3,294,183 A | 12/1966 | Riley et al. |
| 3,472,083 A | 10/1969 | Schnepel |
| 3,513,724 A | 5/1970 | Box |
| 3,595,074 A | 7/1971 | Johnson |
| 3,734,207 A | 5/1973 | Fishbein |
| 3,739,923 A | 6/1973 | Totsuka |
| 3,784,031 A | 1/1974 | Nitu |
| 3,790,002 A | 2/1974 | Guilbaud et al. |
| 3,921,536 A | 11/1975 | Savage |
| 3,926,386 A | 12/1975 | Stahmann |
| 4,141,245 A | 2/1979 | Brandstetter |
| 4,241,884 A | 12/1980 | Lynch |
| 4,243,034 A | 1/1981 | Brandt |
| 4,351,493 A | 9/1982 | Sonnek |
| 4,357,843 A | 11/1982 | Peck et al. |
| 4,384,493 A | 5/1983 | Grunbaum |
| 4,507,026 A | 3/1985 | Lund |
| 4,530,471 A | 7/1985 | Inoue |
| 4,555,960 A | 12/1985 | King |
| 4,688,555 A | 8/1987 | Wardle |
| 4,745,908 A | 5/1988 | Wardle |
| 4,784,150 A | 11/1988 | Voorhies et al. |
| 4,857,058 A | 8/1989 | Payton |
| 4,907,168 A | 3/1990 | Boggs |
| 4,945,790 A | 8/1990 | Golden |
| 5,207,128 A | 5/1993 | Albright |
| 5,234,428 A | 8/1993 | Kaufman |
| 5,256,150 A | 10/1993 | Quiachon et al. |
| 5,277,085 A | 1/1994 | Tanimura et al. |
| 5,350,101 A | 9/1994 | Godlewski |
| 5,426,687 A | 6/1995 | Goodall et al. |
| 5,507,725 A | 4/1996 | Savage et al. |
| 5,524,180 A | 6/1996 | Wang et al. |
| 5,559,294 A | 9/1996 | Hoium et al. |
| 5,709,661 A | 1/1998 | Van Egmond et al. |
| 5,767,840 A | 6/1998 | Selker |
| 5,779,623 A | 7/1998 | Bonnell |
| 5,792,135 A | 8/1998 | Madhani et al. |
| 5,797,900 A | 8/1998 | Madhani |
| 5,842,390 A | 12/1998 | Bouligny |
| 5,855,583 A | 1/1999 | Wang et al. |
| 5,921,968 A | 7/1999 | Lampropoulos et al. |
| 5,967,934 A | 10/1999 | Ishida et al. |
| 6,077,219 A | 6/2000 | Viebach et al. |
| 6,084,371 A | 7/2000 | Kress et al. |
| 6,154,000 A | 11/2000 | Rastegar et al. |
| 6,171,234 B1 | 1/2001 | White et al. |
| 6,185,478 B1 | 2/2001 | Koakutsu et al. |
| 6,272,371 B1 | 8/2001 | Shlomo |
| 6,289,579 B1 | 9/2001 | Viza et al. |
| 6,394,998 B1 | 5/2002 | Wallace et al. |
| 6,401,572 B1 | 6/2002 | Provost |
| 6,436,107 B1 | 8/2002 | Wang et al. |
| 6,487,940 B2 | 12/2002 | Hart et al. |
| 6,491,701 B2 | 12/2002 | Tierney et al. |
| 6,695,818 B2 | 2/2004 | Wollschlager |
| 6,726,675 B1 | 4/2004 | Beyar |
| 6,786,896 B1 | 9/2004 | Madhani et al. |
| 6,827,712 B2 | 12/2004 | Tovey et al. |
| 7,044,936 B2 | 5/2006 | Harding |
| 7,172,580 B2 | 2/2007 | Hruska et al. |
| 7,248,944 B2 | 7/2007 | Green |
| 7,276,044 B2 | 10/2007 | Ferry et al. |
| 7,615,042 B2 | 11/2009 | Beyar et al. |
| 7,635,342 B2 | 12/2009 | Ferry et al. |
| 7,766,856 B2 | 8/2010 | Ferry et al. |
| 7,938,809 B2 | 5/2011 | Lampropoulos et al. |
| 7,972,298 B2 | 7/2011 | Wallace et al. |
| 7,974,674 B2 | 7/2011 | Hauck et al. |
| 7,998,020 B2 | 8/2011 | Kidd et al. |
| 8,052,636 B2 | 11/2011 | Moll et al. |
| 8,157,308 B2 | 4/2012 | Pedersen |
| 8,182,415 B2 | 5/2012 | Larkin et al. |
| 8,277,417 B2 | 10/2012 | Fedinec et al. |
| 8,291,791 B2 | 10/2012 | Light et al. |
| 8,414,505 B1 | 4/2013 | Weitzner |
| 8,425,465 B2 | 4/2013 | Nagano |
| 8,541,970 B2 | 9/2013 | Nowlin |
| 8,671,817 B1 | 3/2014 | Bogusky |
| 8,720,448 B2 | 5/2014 | Reis et al. |
| 8,746,252 B2 | 6/2014 | McGrogan et al. |
| 8,870,815 B2 | 10/2014 | Bhat et al. |
| 8,961,533 B2 | 2/2015 | Stahler et al. |
| 8,968,333 B2 | 3/2015 | Yu et al. |
| 8,992,542 B2 | 3/2015 | Hagag et al. |
| 9,173,713 B2 | 11/2015 | Hart et al. |
| 9,204,933 B2 | 12/2015 | Reis et al. |
| 9,259,280 B2 | 2/2016 | Au |
| 9,259,281 B2 | 2/2016 | Griffiths et al. |
| 9,326,822 B2 | 5/2016 | Lewis et al. |
| 9,408,669 B2 | 8/2016 | Kokish et al. |
| 9,446,177 B2 | 9/2016 | Millman et al. |
| 9,452,018 B2 | 9/2016 | Yu |
| 9,457,168 B2 | 10/2016 | Moll et al. |
| 9,498,601 B2 | 11/2016 | Tanner et al. |
| 9,504,604 B2 | 11/2016 | Alvarez |
| 9,561,083 B2 | 2/2017 | Yu et al. |
| 9,622,827 B2 | 4/2017 | Yu et al. |
| 9,636,184 B2 | 5/2017 | Lee et al. |
| 9,636,483 B2 | 5/2017 | Hart et al. |
| 9,668,814 B2 | 6/2017 | Kokish |
| 9,713,509 B2 | 7/2017 | Schuh et al. |
| 9,727,963 B2 | 8/2017 | Mintz et al. |
| 9,737,371 B2 | 8/2017 | Romo et al. |
| 9,737,373 B2 | 8/2017 | Schuh |
| 9,744,335 B2 | 8/2017 | Jiang |
| 9,763,741 B2 | 9/2017 | Alvarez et al. |
| 9,788,910 B2 | 10/2017 | Schuh |
| 9,844,412 B2 | 12/2017 | Bogusky et al. |
| 9,867,635 B2 | 1/2018 | Alvarez et al. |
| 9,918,659 B2 | 3/2018 | Chopra |
| 9,918,681 B2 | 3/2018 | Wallace et al. |
| 9,931,025 B1 | 4/2018 | Graetzel et al. |
| 9,949,749 B2 | 4/2018 | Noonan et al. |
| 9,955,986 B2 | 5/2018 | Shah |
| 9,962,228 B2 | 5/2018 | Schuh et al. |
| 9,980,785 B2 | 5/2018 | Schuh |
| 9,993,313 B2 | 6/2018 | Schuh et al. |
| 9,993,614 B2 | 6/2018 | Pacheco |
| 10,016,900 B1 | 7/2018 | Meyer et al. |
| 10,022,192 B1 | 7/2018 | Ummalaneni |

(56) References Cited

U.S. PATENT DOCUMENTS

| | | |
|---|---|---|
| 10,046,140 B2 | 8/2018 | Kokish et al. |
| 10,080,576 B2 | 9/2018 | Romo et al. |
| 10,136,959 B2 | 11/2018 | Mintz et al. |
| 10,143,360 B2 | 12/2018 | Roelle et al. |
| 10,145,747 B1 | 12/2018 | Lin et al. |
| 10,149,720 B2 | 12/2018 | Romo |
| 10,159,532 B1 | 12/2018 | Ummalaneni et al. |
| 10,159,533 B2 | 12/2018 | Moll et al. |
| 10,169,875 B2 | 1/2019 | Mintz et al. |
| 10,213,264 B2 | 2/2019 | Tanner et al. |
| 10,219,874 B2 | 3/2019 | Yu et al. |
| 10,231,793 B2 | 3/2019 | Romo |
| 10,231,867 B2 | 3/2019 | Alvarez et al. |
| 10,244,926 B2 | 4/2019 | Noonan et al. |
| 10,258,285 B2 | 4/2019 | Hauck |
| 10,285,574 B2 | 5/2019 | Landey et al. |
| 10,299,870 B2 | 5/2019 | Connolly et al. |
| 10,314,463 B2 | 6/2019 | Agrawal et al. |
| 10,383,765 B2 | 8/2019 | Alvarez et al. |
| 10,398,518 B2 | 9/2019 | Yu et al. |
| 10,405,939 B2 | 9/2019 | Romo et al. |
| 10,405,940 B2 | 9/2019 | Romo |
| 10,426,559 B2 | 10/2019 | Graetzel et al. |
| 10,426,661 B2 | 10/2019 | Kintz |
| 10,434,660 B2 | 10/2019 | Meyer |
| 10,454,347 B2 | 10/2019 | Covington et al. |
| 10,464,209 B2 | 11/2019 | Ho et al. |
| 10,470,830 B2 | 11/2019 | Hill |
| 10,478,595 B2 | 11/2019 | Kokish |
| 10,482,599 B2 | 11/2019 | Mintz et al. |
| 10,493,239 B2 | 12/2019 | Hart et al. |
| 10,493,241 B2 | 12/2019 | Jiang |
| 10,499,795 B2 | 12/2019 | Ogawa et al. |
| 10,500,001 B2 | 12/2019 | Yu et al. |
| 10,517,692 B2 | 12/2019 | Eyre et al. |
| 10,524,866 B2 | 1/2020 | Srinivasan |
| 10,524,867 B2 | 1/2020 | Kokish et al. |
| 10,539,478 B2 | 1/2020 | Lin |
| 10,543,047 B2 | 1/2020 | Yu |
| 10,543,048 B2 | 1/2020 | Noonan et al. |
| 10,555,778 B2 | 2/2020 | Ummalaneni et al. |
| 10,556,092 B2 | 2/2020 | Yu et al. |
| 10,569,052 B2 | 2/2020 | Kokish et al. |
| 10,631,949 B2 | 4/2020 | Schuh et al. |
| 10,639,108 B2 | 5/2020 | Romo et al. |
| 10,639,109 B2 | 5/2020 | Bovay et al. |
| 10,639,114 B2 | 5/2020 | Schuh |
| 10,667,871 B2 | 6/2020 | Romo et al. |
| 10,667,875 B2 | 6/2020 | DeFonzo |
| 10,682,189 B2 | 6/2020 | Schuh et al. |
| 10,687,903 B2 | 6/2020 | Lewis et al. |
| 10,695,536 B2 | 6/2020 | Weitzner et al. |
| 10,702,348 B2 | 7/2020 | Moll et al. |
| 10,716,461 B2 | 7/2020 | Jenkins |
| 10,743,751 B2 | 8/2020 | Landey et al. |
| 10,744,035 B2 | 8/2020 | Alvarez et al. |
| 10,751,140 B2 | 8/2020 | Wallace et al. |
| 10,765,303 B2 | 9/2020 | Graetzel et al. |
| 10,765,487 B2 | 9/2020 | Ho |
| 10,779,898 B2 | 9/2020 | Hill |
| 10,786,329 B2 | 9/2020 | Schuh et al. |
| 10,786,432 B2 | 10/2020 | Mintz et al. |
| 10,792,112 B2 | 10/2020 | Kokish et al. |
| 10,792,464 B2 | 10/2020 | Romo et al. |
| 10,792,466 B2 | 10/2020 | Landey et al. |
| 10,813,539 B2 | 10/2020 | Graetzel et al. |
| 10,814,101 B2 | 10/2020 | Jiang |
| 10,820,947 B2 | 11/2020 | Julian |
| 10,820,952 B2 | 11/2020 | Yu |
| 10,820,954 B2 | 11/2020 | Marsot et al. |
| 10,827,913 B2 | 11/2020 | Ummalaneni et al. |
| 10,828,118 B2 | 11/2020 | Schuh et al. |
| 10,835,153 B2 | 11/2020 | Rafil-Tari et al. |
| 10,850,013 B2 | 12/2020 | Hsu |
| 2001/0042643 A1 | 11/2001 | Krueger et al. |
| 2002/0045905 A1 | 4/2002 | Gerbi et al. |
| 2002/0098938 A1 | 7/2002 | Milbourne et al. |
| 2002/0100254 A1 | 8/2002 | Dharssi |
| 2002/0103418 A1 | 8/2002 | Maeda et al. |
| 2002/0107573 A1 | 8/2002 | Steinberg |
| 2002/0117017 A1 | 8/2002 | Bernhardt et al. |
| 2002/0161355 A1 | 10/2002 | Wollschlager |
| 2002/0161426 A1 | 10/2002 | Lancea |
| 2002/0177789 A1 | 11/2002 | Ferry et al. |
| 2003/0056561 A1 | 3/2003 | Butscher et al. |
| 2003/0167623 A1 | 9/2003 | Lorenz |
| 2003/0212308 A1 | 11/2003 | Bendall |
| 2004/0015053 A1 | 1/2004 | Bieger |
| 2004/0152972 A1 | 8/2004 | Hunter |
| 2004/0243147 A1 | 12/2004 | Lipow |
| 2004/0254566 A1 | 12/2004 | Plicchi |
| 2005/0004579 A1 | 1/2005 | Schneider et al. |
| 2005/0177026 A1 | 8/2005 | Hoeg et al. |
| 2005/0183532 A1 | 8/2005 | Najaf et al. |
| 2005/0222554 A1 | 10/2005 | Wallace et al. |
| 2006/0041245 A1 | 2/2006 | Ferry |
| 2006/0111692 A1 | 5/2006 | Hlavka et al. |
| 2006/0142657 A1 | 6/2006 | Quaid |
| 2006/0146010 A1 | 7/2006 | Schneider |
| 2006/0201688 A1 | 9/2006 | Jenner et al. |
| 2006/0229587 A1 | 10/2006 | Beyar et al. |
| 2006/0237205 A1 | 10/2006 | Sia et al. |
| 2007/0000498 A1 | 1/2007 | Glynn et al. |
| 2007/0013336 A1 | 1/2007 | Nowlin et al. |
| 2007/0060879 A1 | 3/2007 | Weitzner et al. |
| 2007/0100201 A1 | 5/2007 | Komiya et al. |
| 2007/0100254 A1 | 5/2007 | Murakami |
| 2007/0112355 A1 | 5/2007 | Salahieh |
| 2007/0119274 A1* | 5/2007 | Devengenzo .......... A61B 34/71 74/490.01 |
| 2007/0149946 A1 | 6/2007 | Viswanathan |
| 2007/0185485 A1 | 8/2007 | Hauck et al. |
| 2007/0191177 A1 | 8/2007 | Nagai et al. |
| 2007/0239028 A1 | 10/2007 | Houser |
| 2007/0245175 A1 | 10/2007 | Zheng et al. |
| 2007/0299427 A1 | 12/2007 | Yeung et al. |
| 2008/0039255 A1 | 2/2008 | Jinno et al. |
| 2008/0046122 A1 | 2/2008 | Manzo et al. |
| 2008/0065103 A1 | 3/2008 | Cooper et al. |
| 2008/0147011 A1 | 6/2008 | Urmey |
| 2008/0177285 A1 | 7/2008 | Brock et al. |
| 2008/0214925 A1 | 9/2008 | Wilson et al. |
| 2008/0243064 A1 | 10/2008 | Stahler et al. |
| 2008/0249536 A1 | 10/2008 | Stahler et al. |
| 2008/0253108 A1 | 10/2008 | Yu et al. |
| 2008/0262301 A1 | 10/2008 | Gibbons et al. |
| 2008/0287963 A1 | 11/2008 | Rogers et al. |
| 2008/0302200 A1 | 12/2008 | Tobey |
| 2009/0005768 A1 | 1/2009 | Sharareh |
| 2009/0082722 A1 | 3/2009 | Munger et al. |
| 2009/0098971 A1 | 4/2009 | Ho et al. |
| 2009/0105645 A1 | 4/2009 | Kidd et al. |
| 2009/0163948 A1 | 6/2009 | Sunaoshi et al. |
| 2009/0171371 A1 | 7/2009 | Nixon |
| 2009/0247944 A1 | 10/2009 | Kirschenman et al. |
| 2009/0248039 A1 | 10/2009 | Cooper et al. |
| 2010/0030023 A1 | 2/2010 | Yoshie |
| 2010/0069833 A1 | 3/2010 | Wenderow et al. |
| 2010/0073150 A1 | 3/2010 | Olson et al. |
| 2010/0082041 A1 | 4/2010 | Prisco |
| 2010/0130923 A1 | 5/2010 | Cleary et al. |
| 2010/0130987 A1 | 5/2010 | Wenderow et al. |
| 2010/0175701 A1 | 7/2010 | Reis et al. |
| 2010/0204646 A1 | 8/2010 | Plicchi et al. |
| 2010/0210923 A1 | 8/2010 | Li et al. |
| 2010/0248177 A1 | 9/2010 | Mangelberger et al. |
| 2010/0249506 A1 | 9/2010 | Prisco |
| 2010/0274078 A1 | 10/2010 | Kim et al. |
| 2010/0332033 A1 | 12/2010 | Diolaiti |
| 2011/0009863 A1 | 1/2011 | Stanislaw |
| 2011/0015484 A1 | 1/2011 | Alvarez et al. |
| 2011/0015648 A1 | 1/2011 | Alvarez et al. |
| 2011/0015650 A1 | 1/2011 | Choi et al. |
| 2011/0028790 A1 | 2/2011 | Farr et al. |

(56) References Cited

U.S. PATENT DOCUMENTS

| | | |
|---|---|---|
| 2011/0028991 A1 | 2/2011 | Ikeda et al. |
| 2011/0130718 A1 | 6/2011 | Kidd et al. |
| 2011/0147030 A1 | 6/2011 | Blum et al. |
| 2011/0152880 A1 | 6/2011 | Alvarez et al. |
| 2011/0238083 A1 | 9/2011 | Moll et al. |
| 2011/0261183 A1 | 10/2011 | Ma et al. |
| 2011/0277775 A1 | 11/2011 | Holop et al. |
| 2011/0288573 A1 | 11/2011 | Yates et al. |
| 2011/0306836 A1 | 12/2011 | Ohline et al. |
| 2012/0071821 A1 | 3/2012 | Yu |
| 2012/0071894 A1 | 3/2012 | Tanner et al. |
| 2012/0071895 A1 | 3/2012 | Stahler et al. |
| 2012/0132018 A1 | 5/2012 | Tang |
| 2012/0136419 A1 | 5/2012 | Zarembo et al. |
| 2012/0143226 A1 | 6/2012 | Belson et al. |
| 2012/0150154 A1 | 6/2012 | Brisson et al. |
| 2012/0186194 A1 | 7/2012 | Schlieper |
| 2012/0191107 A1 | 7/2012 | Tanner et al. |
| 2012/0232476 A1 | 9/2012 | Bhat et al. |
| 2012/0239012 A1 | 9/2012 | Laurent et al. |
| 2012/0277730 A1 | 11/2012 | Salahieh |
| 2012/0283747 A1 | 11/2012 | Popovic |
| 2013/0018400 A1 | 1/2013 | Milton et al. |
| 2013/0066335 A1 | 3/2013 | Barwinkel |
| 2013/0144116 A1 | 6/2013 | Cooper et al. |
| 2013/0204124 A1 | 8/2013 | Duindam |
| 2013/0226151 A1 | 8/2013 | Suehara |
| 2013/0231678 A1 | 9/2013 | Wenderow |
| 2013/0304084 A1 | 11/2013 | Beira et al. |
| 2013/0317519 A1 | 11/2013 | Romo et al. |
| 2013/0345519 A1 | 12/2013 | Piskun et al. |
| 2014/0000411 A1 | 1/2014 | Shelton, IV et al. |
| 2014/0066944 A1 | 3/2014 | Taylor et al. |
| 2014/0069437 A1 | 3/2014 | Reis et al. |
| 2014/0142591 A1 | 5/2014 | Alvarez et al. |
| 2014/0166023 A1 | 6/2014 | Kishi |
| 2014/0171778 A1 | 6/2014 | Tsusaka |
| 2014/0180063 A1 | 6/2014 | Zhao |
| 2014/0222019 A1 | 8/2014 | Brudnick |
| 2014/0243849 A1 | 8/2014 | Saglam et al. |
| 2014/0276233 A1 | 9/2014 | Murphy |
| 2014/0276389 A1 | 9/2014 | Walker |
| 2014/0276394 A1 | 9/2014 | Wong et al. |
| 2014/0276594 A1 | 9/2014 | Tanner et al. |
| 2014/0276935 A1 | 9/2014 | Yu |
| 2014/0276936 A1 | 9/2014 | Kokish et al. |
| 2014/0277334 A1 | 9/2014 | Yu et al. |
| 2014/0357984 A1 | 12/2014 | Wallace et al. |
| 2014/0375784 A1 | 12/2014 | Massetti |
| 2015/0012134 A1 | 1/2015 | Robinson |
| 2015/0090063 A1 | 4/2015 | Lantermann et al. |
| 2015/0133963 A1 | 5/2015 | Barbagli |
| 2015/0142013 A1 | 5/2015 | Tanner et al. |
| 2015/0144514 A1 | 5/2015 | Brennan et al. |
| 2015/0148600 A1 | 5/2015 | Ashinuma et al. |
| 2015/0150635 A1 | 6/2015 | Kilroy |
| 2015/0182250 A1 | 7/2015 | Conlon et al. |
| 2015/0231364 A1 | 8/2015 | Blanchard |
| 2015/0374445 A1 | 12/2015 | Gombert et al. |
| 2016/0000512 A1 | 1/2016 | Gombert et al. |
| 2016/0157945 A1 | 6/2016 | Madhani |
| 2016/0166234 A1 | 6/2016 | Zhang |
| 2016/0192860 A1 | 7/2016 | Allenby |
| 2016/0206389 A1 | 7/2016 | Miller |
| 2016/0213435 A1 | 7/2016 | Hourtash |
| 2016/0270865 A1 | 9/2016 | Landey et al. |
| 2016/0287279 A1 | 10/2016 | Bovay et al. |
| 2016/0338783 A1 | 11/2016 | Romo et al. |
| 2016/0346049 A1 | 12/2016 | Allen et al. |
| 2017/0007337 A1 | 1/2017 | Dan |
| 2017/0020615 A1 | 1/2017 | Koenig et al. |
| 2017/0151028 A1 | 6/2017 | Ogawa et al. |
| 2017/0202627 A1 | 7/2017 | Sramek et al. |
| 2017/0209073 A1 | 7/2017 | Sramek et al. |
| 2017/0252096 A1 | 9/2017 | Felder |
| 2017/0258534 A1 | 9/2017 | Hourtash |
| 2017/0281049 A1 | 10/2017 | Yamamoto |
| 2017/0290631 A1 | 10/2017 | Lee et al. |
| 2017/0325932 A1 | 11/2017 | Hoelzle |
| 2018/0025666 A1 | 1/2018 | Ho et al. |
| 2018/0042464 A1 | 2/2018 | Arai |
| 2018/0042686 A1 | 2/2018 | Peine |
| 2018/0049792 A1 | 2/2018 | Eckert |
| 2018/0055577 A1* | 3/2018 | Barral .................... A61B 34/20 |
| 2018/0056044 A1 | 3/2018 | Choi et al. |
| 2018/0104820 A1 | 4/2018 | Troy et al. |
| 2018/0116735 A1 | 5/2018 | Tiemey et al. |
| 2018/0206927 A1 | 7/2018 | Prisco et al. |
| 2018/0221038 A1 | 8/2018 | Noonan et al. |
| 2018/0221039 A1 | 8/2018 | Shah |
| 2018/0243048 A1 | 8/2018 | Shan |
| 2018/0279852 A1 | 10/2018 | Rafii-Tari et al. |
| 2018/0289431 A1 | 10/2018 | Draper et al. |
| 2018/0296299 A1 | 10/2018 | Iceman |
| 2018/0303566 A1 | 10/2018 | Soundararajan |
| 2018/0325499 A1 | 11/2018 | Landey et al. |
| 2018/0326181 A1 | 11/2018 | Kokish et al. |
| 2018/0360435 A1 | 12/2018 | Romo |
| 2019/0000559 A1 | 1/2019 | Berman et al. |
| 2019/0000560 A1 | 1/2019 | Berman et al. |
| 2019/0000576 A1 | 1/2019 | Mintz et al. |
| 2019/0110839 A1 | 4/2019 | Rafii-Tari et al. |
| 2019/0151148 A1 | 4/2019 | Alvarez et al. |
| 2019/0142537 A1 | 5/2019 | Covington et al. |
| 2019/0167366 A1 | 6/2019 | Ummalaneni |
| 2019/0175009 A1 | 6/2019 | Mintz |
| 2019/0183585 A1 | 6/2019 | Rafii-Tari et al. |
| 2019/0183587 A1 | 6/2019 | Rafii-Tari et al. |
| 2019/0216548 A1 | 7/2019 | Ummalaneni |
| 2019/0216576 A1 | 7/2019 | Eyre |
| 2019/0223967 A1 | 7/2019 | Abbott |
| 2019/0223974 A1 | 7/2019 | Romo |
| 2019/0231458 A1 | 8/2019 | DiMaio |
| 2019/0262086 A1 | 8/2019 | Connolly et al. |
| 2019/0269468 A1 | 9/2019 | Hsu et al. |
| 2019/0274764 A1 | 9/2019 | Romo |
| 2019/0290109 A1 | 9/2019 | Agrawal et al. |
| 2019/0298460 A1 | 10/2019 | Al-Jadda |
| 2019/0298465 A1 | 10/2019 | Chin |
| 2019/0336238 A1 | 11/2019 | Yu |
| 2019/0365201 A1 | 12/2019 | Noonan et al. |
| 2019/0365209 A1 | 12/2019 | Ye et al. |
| 2019/0365479 A1 | 12/2019 | Rafii-Tari |
| 2019/0365486 A1 | 12/2019 | Srinivasan et al. |
| 2019/0375383 A1 | 12/2019 | Alvarez |
| 2019/0380787 A1 | 12/2019 | Ye |
| 2019/0380797 A1 | 12/2019 | Yu |
| 2020/0000533 A1 | 1/2020 | Schuh |
| 2020/0008874 A1 | 1/2020 | Barbagli et al. |
| 2020/0038123 A1 | 2/2020 | Graetzel |
| 2020/0039086 A1 | 2/2020 | Meyer |
| 2020/0046434 A1 | 2/2020 | Graetzel |
| 2020/0060516 A1 | 2/2020 | Baez |
| 2020/0085516 A1 | 3/2020 | DeFonzo |
| 2020/0086087 A1 | 3/2020 | Hart et al. |
| 2020/0091799 A1 | 3/2020 | Covington et al. |
| 2020/0093549 A1 | 3/2020 | Chin |
| 2020/0093554 A1 | 3/2020 | Schuh |
| 2020/0100855 A1 | 4/2020 | Leparmentier |
| 2020/0107894 A1 | 4/2020 | Wallace |
| 2020/0121502 A1 | 4/2020 | Kintz |
| 2020/0129252 A1 | 4/2020 | Kokish |
| 2020/0146769 A1 | 5/2020 | Eyre |
| 2020/0155245 A1 | 5/2020 | Yu |
| 2020/0155801 A1 | 5/2020 | Kokish |
| 2020/0170720 A1 | 6/2020 | Ummalaneni |
| 2020/0171660 A1 | 6/2020 | Ho |
| 2020/0188043 A1 | 6/2020 | Yu |
| 2020/0197112 A1 | 6/2020 | Chin |
| 2020/0206472 A1 | 7/2020 | Ma |
| 2020/0217733 A1 | 7/2020 | Lin |
| 2020/0222134 A1 | 7/2020 | Schuh |
| 2020/0230360 A1 | 7/2020 | Yu |
| 2020/0237458 A1 | 7/2020 | DeFonzo |

(56) References Cited

U.S. PATENT DOCUMENTS

| | | |
|---|---|---|
| 2020/0261172 A1 | 8/2020 | Romo |
| 2020/0268459 A1 | 8/2020 | Noonan et al. |
| 2020/0268460 A1 | 8/2020 | Tse |
| 2020/0281787 A1 | 9/2020 | Ruiz |
| 2020/0297437 A1 | 9/2020 | Schuh |
| 2020/0297444 A1 | 9/2020 | Camarillo |
| 2020/0305983 A1 | 10/2020 | Yampolsky |
| 2020/0305989 A1 | 10/2020 | Schuh |
| 2020/0305992 A1 | 10/2020 | Schuh |
| 2020/0315717 A1 | 10/2020 | Bovay |
| 2020/0315723 A1 | 10/2020 | Hassan |
| 2020/0323596 A1 | 10/2020 | Moll |
| 2020/0330167 A1 | 10/2020 | Romo |
| 2020/0345216 A1 | 11/2020 | Jenkins |
| 2020/0352420 A1 | 11/2020 | Graetzel |
| 2020/0360183 A1 | 11/2020 | Alvarez |
| 2020/0367726 A1 | 11/2020 | Landey et al. |
| 2020/0367981 A1 | 11/2020 | Ho et al. |
| 2020/0375678 A1 | 12/2020 | Wallace |
| 2020/0383735 A1 | 12/2020 | Lewis et al. |

FOREIGN PATENT DOCUMENTS

| | | |
|---|---|---|
| CN | 201884596 U | 6/2011 |
| CN | 102316817 | 1/2012 |
| CN | 102327118 | 1/2012 |
| CN | 102458295 | 5/2012 |
| CN | 102665590 | 9/2012 |
| CN | 102834043 | 12/2012 |
| CN | 102973317 | 3/2013 |
| CN | 102015759 | 4/2013 |
| CN | 103735313 | 4/2014 |
| CN | 105147393 | 12/2015 |
| CN | 105559850 | 5/2016 |
| CN | 105559886 | 5/2016 |
| DE | 19649082 | 1/1998 |
| DE | 102004020465 | 9/2005 |
| EP | 1 442 720 | 8/2004 |
| EP | 2 567 670 | 3/2013 |
| EP | 3 025 630 | 6/2016 |
| EP | 3025633 A1 | 6/2016 |
| JP | 07-136173 | 5/1995 |
| JP | 2009-139187 | 6/2009 |
| JP | 2010-046384 | 3/2010 |
| JP | 2014-159071 | 9/2014 |
| WO | WO 94/14494 | 7/1994 |
| WO | WO 02/74178 | 9/2002 |
| WO | WO 07/146987 | 12/2007 |
| WO | WO 09/092059 | 7/2009 |
| WO | 2010002544 A1 | 1/2010 |
| WO | WO 11/005335 | 1/2011 |
| WO | WO 12/037506 | 3/2012 |
| WO | WO 13/179600 | 12/2013 |
| WO | WO 15/127231 | 8/2015 |
| WO | 2016043845 A1 | 3/2016 |
| WO | WO 17/059412 | 4/2017 |
| WO | WO 17/151993 | 9/2017 |

OTHER PUBLICATIONS

Mayo Clinic, Robotic Surgery, https://www.mayoclinic.org/tests-procedures/robotic-surgery/about/pac- 20394974?p=1, downloaded from the internet on Jul. 12, 2018, 2 pgs.
Non-Final Rejection for U.S. Appl. No. 16/583,653, dated Jan. 22, 2020, 12 pages.
Notice of Allowance for U.S. Appl. No. 16/583,653, dated Jul. 23, 2020, 8 pages.
Mayo Clinic, Robotic Surgery, https://www.mayoclinic.org/tests-procedures/robotic-surgery/about/pac-20394974?p=1, downloaded from the internet on Jul. 12, 2018, 2 pp.
International search report and written opinion dated Jan. 22, 2020 in application No. PCT/US2019/53093.

* cited by examiner

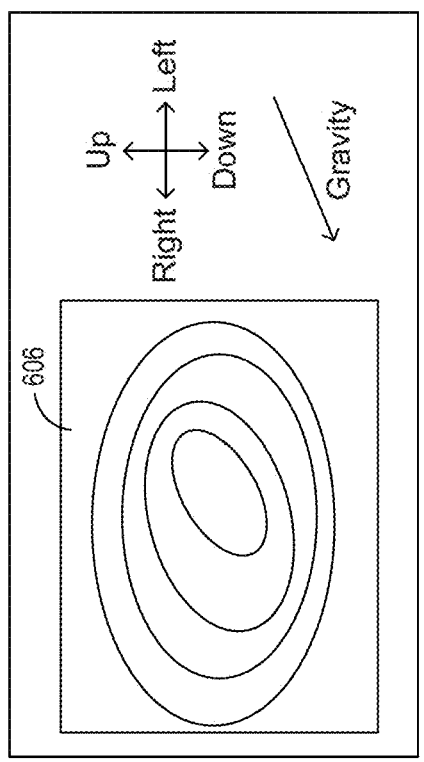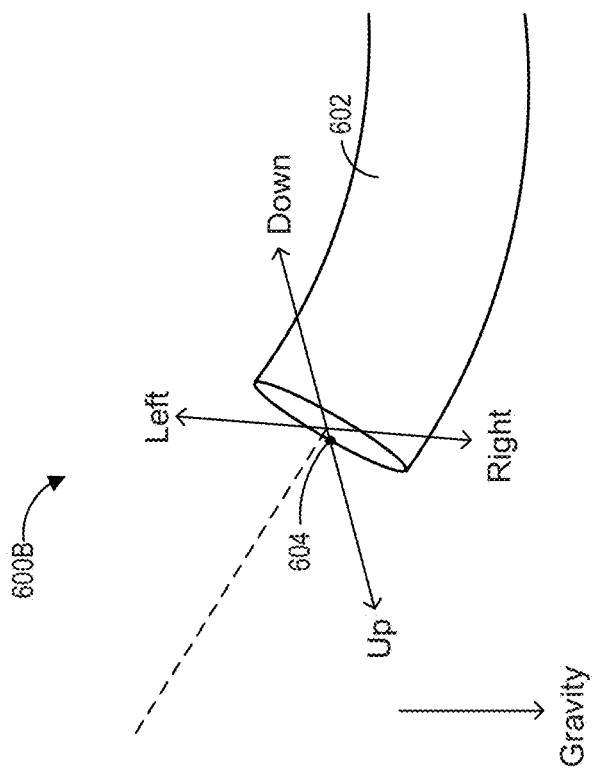
FIG. 29A

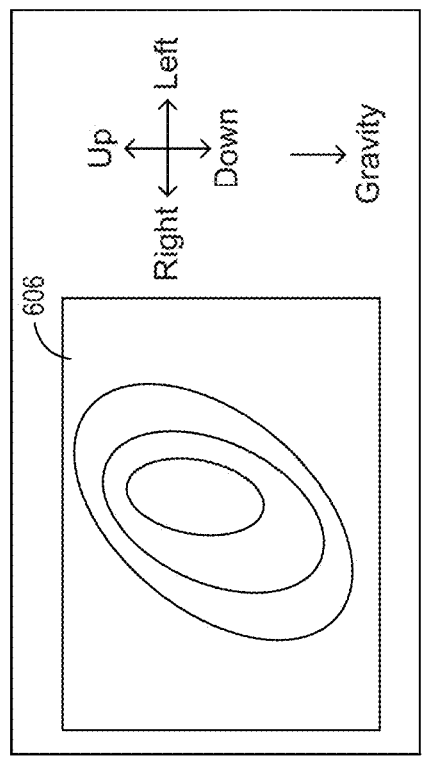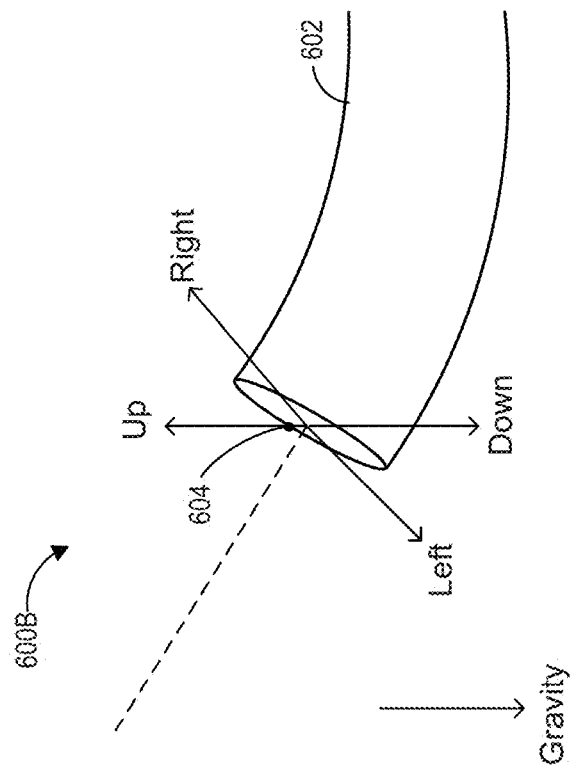
FIG. 29B

DEVICES, SYSTEMS, AND METHODS FOR MANUALLY AND ROBOTICALLY DRIVING MEDICAL INSTRUMENTS

PRIORITY APPLICATION(S)

This application is continuation of U.S. application Ser. No. 16/583,653, filed Sep. 26, 2019, which claims priority to U.S. Provisional Application No. 62/738,436, filed Sep. 28, 2018, each of which is incorporated herein by reference. Any and all applications for which a foreign or domestic priority claim is identified in the Application Data Sheet as filed with the present application are hereby incorporated by reference under 37 CFR 1.57.

TECHNICAL FIELD

This application relates to devices, systems, and methods for driving medical instruments, and more particularly, to devices, systems, and methods for manually and robotically driving medical instruments, such as endoscopes, for example.

BACKGROUND

Medical procedures such as endoscopy may involve accessing and visualizing the inside of a patient's anatomy for diagnostic and/or therapeutic purposes. For example, gastroenterology, urology, and bronchology involve medical procedures that allow a physician to examine patient lumens, such as the ureter, gastrointestinal tract, and airways (bronchi and bronchioles). During these procedures, a thin, flexible tubular tool or instrument, known as an endoscope, is inserted into the patient through an orifice (such as a natural orifice) and advanced towards a tissue site identified for subsequent diagnosis and/or treatment. The medical instrument can be controllable and articulable to facilitate navigation through the anatomy.

SUMMARY

The systems, methods and devices of this disclosure each have several innovative aspects, no single one of which is solely responsible for the desirable attributes disclosed herein.

In a first aspect, a device for driving a medical instrument includes a handle configured to receive an elongated shaft of a medical instrument; a gripping mechanism positioned in the handle for selectively engaging the elongated shaft, the gripping mechanism configured to fixedly attach to the elongated shaft when engaged and to allow the handle to slide along the elongated shaft when disengaged; an articulation input configured to receive user inputs of commanded articulation of the elongated shaft; and a communications circuit positioned in the handle and configured to transmit user inputs received at the articulation input to an instrument drive mechanism attached to the medical instrument, the instrument drive mechanism configured to cause articulation of the elongated shaft based on the transmitted user inputs.

In some embodiments, the device includes one or more of the following features in any combination: (a) wherein the articulation input is positioned on the handle; (b) wherein the articulation input is separate from the handle; (c) wherein the handle comprises a channel configured to receive the elongated shaft; (d) wherein the gripping mechanism comprises: a clamping mechanism positioned within the channel and configured to clamp onto the elongated shaft, and an actuator configured to release the clamping mechanism such that the elongated shaft is slidable within the channel when the actuator is actuated; (e) an insertion mechanism for driving insertion of the elongated shaft relative to the handle; (f) a roll mechanism for driving roll of the elongated shaft; (g) wherein the device is configured to automatically roll the elongated shaft using the roll mechanism to retain a gravity based orientation of the medical instrument; (h) wherein the device is configured to provide on-axis navigation such that user inputs of commanded articulation cause articulation of the elongated shaft in the gravity based orientation irrespective of roll of the elongated shaft; (i) wherein the articulation input is configured to receive user inputs indicative of movements in at least two directions; (j) wherein the articulation input comprises a joystick; (k) wherein the handle extends along a longitudinal axis, the joystick extends along the longitudinal axis, and the joystick is articulable about the longitudinal axis; (l) wherein the articulation input comprises one or more buttons positioned on the handle; (m) wherein the communications circuit comprises a wireless communication transmitter and receiver; (n) wherein the device is configured to allow a user to advance, retract, and articulate the elongated shaft of the medical instrument with a single hand; and/or (o) wherein the handle is positionable on the elongated shaft of the instrument between a base of the instrument and a distal end of the elongated shaft.

In another aspect, a system for driving a medical instrument includes: a handle configured to receive an elongated shaft of a medical instrument, the handle comprising a gripping mechanism for selectively engaging the elongated shaft, the gripping mechanism configured to fixedly attach to the elongated shaft when engaged and to allow the handle to slide along the elongated shaft when disengaged, and an articulation input configured for receiving user inputs of commanded articulation of the elongated shaft; and an instrument drive mechanism configured to engage a base of the medical instrument, the instrument drive mechanism comprising at least one robotic drive output configured to engage a robotic drive input of the base to cause articulation of the elongated shaft based on the user inputs received at the articulation input, and a first connector configured to removably couple the instrument drive mechanism to an instrument positioning device.

In some embodiments, the system further includes one more of the following features in any combination: (a) an instrument positioning device, the instrument positioning device comprising a second connector configured to removably couple the instrument drive mechanism to the first connector of the instrument positioning device; (b) wherein the instrument positioning device comprises a robotic arm; (c) wherein the handle comprises communication circuitry configured to transmit the user inputs to the instrument drive mechanism, and the instrument drive mechanism is configured to cause articulation of the elongated shaft based on the transmitted user inputs; (d) wherein the communication circuitry is wireless; (e) wherein the communication circuitry directly transmits the user inputs to the instrument drive mechanism; (f) wherein the communication circuitry indirectly transmits the user inputs to the instrument drive mechanism; (g) wherein the instrument drive mechanism is autoclavable; and/or (h) wherein the medical instrument is an endoscope.

In another aspect a method for driving a medical instrument includes: attaching a base of a medical instrument to an instrument drive mechanism such that at least one robotic drive output engages a robotic drive input of the base;

positioning a handle on the elongated shaft of the medical instrument between a distal end of the elongated shaft and the base of the medical instrument; advancing or retracting the elongated shaft into or out of a patient using the handle; and providing user inputs for commanded articulation of the elongated shaft using an articulation input on the handle, wherein the instrument drive mechanism causes articulation of the elongated shaft using the at least one robotic drive output based on the user inputs.

In some embodiments, the method further includes one or more of the following features in any combination: (a) wherein positioning the handle on the elongated shaft comprises disengaging a gripping mechanism to slide the handle along the elongated shaft, and engaging the gripping mechanism to fixedly attach the handle to the elongated shaft; (b) wherein advancing or retracting the elongated shaft into or out of the patient using the handle comprises moving the handle toward or away from the patient while the gripping mechanism is engaged; (c) repositioning the handle along the elongated shaft by disengaging the gripping mechanism, sliding the handle along the elongated shaft, and reengaging the gripping mechanism to fixedly attach the handle to the elongated shaft; (d) wherein advancing or retracting the elongated shaft into or out of the patient using the handle and providing user inputs for commanded articulation of the elongated shaft using the articulation input on the handle are performed with a single hand; (e) wherein advancing or retracting the elongated shaft into or out of the patient using the handle and providing user inputs for commanded articulation of the elongated shaft using the articulation input on the handle are performed simultaneously; (f) connecting the instrument drive mechanism to an instrument positioning device; (g) wherein the instrument positioning device is a robotic arm; (h) advancing or retracting the elongated shaft with the robotic arm; (i) wherein the medical instrument is an endoscope; and/or (j) wherein the method comprises a method for colonoscopy.

BRIEF DESCRIPTION OF THE DRAWINGS

The disclosed aspects will hereinafter be described in conjunction with the appended drawings, provided to illustrate and not to limit the disclosed aspects, wherein like designations denote like elements.

FIG. 29A illustrates a first example control scheme for a robotic medical system in which articulation inputs for causing articulation of the elongated shaft of a medical instrument are provided in an instrument-based orientation.

FIG. 29B illustrates a second example control scheme for a robotic medical system in which articulation inputs for causing articulation of the elongated shaft of a medical instrument are provided in a gravity-based orientation.

DETAILED DESCRIPTION

1. Overview

Aspects of the present disclosure may be integrated into a robotically-enabled medical system capable of performing a variety of medical procedures, including both minimally invasive, such as laparoscopy, and non-invasive, such as endoscopy, procedures. Among endoscopy procedures, the system may be capable of performing bronchoscopy, ureteroscopy, gastroscopy, etc.

In addition to performing the breadth of procedures, the system may provide additional benefits, such as enhanced imaging and guidance to assist the physician. Additionally, the system may provide the physician with the ability to perform the procedure from an ergonomic position without the need for awkward arm motions and positions. Still further, the system may provide the physician with the ability to perform the procedure with improved ease of use such that one or more of the instruments of the system can be controlled by a single user.

Various embodiments will be described below in conjunction with the drawings for purposes of illustration. It should be appreciated that many other implementations of the disclosed concepts are possible, and various advantages can be achieved with the disclosed implementations. Headings are included herein for reference and to aid in locating various sections. These headings are not intended to limit the scope of the concepts described with respect thereto. Such concepts may have applicability throughout the entire specification.

A. Robotic System—Cart

Figure 1:
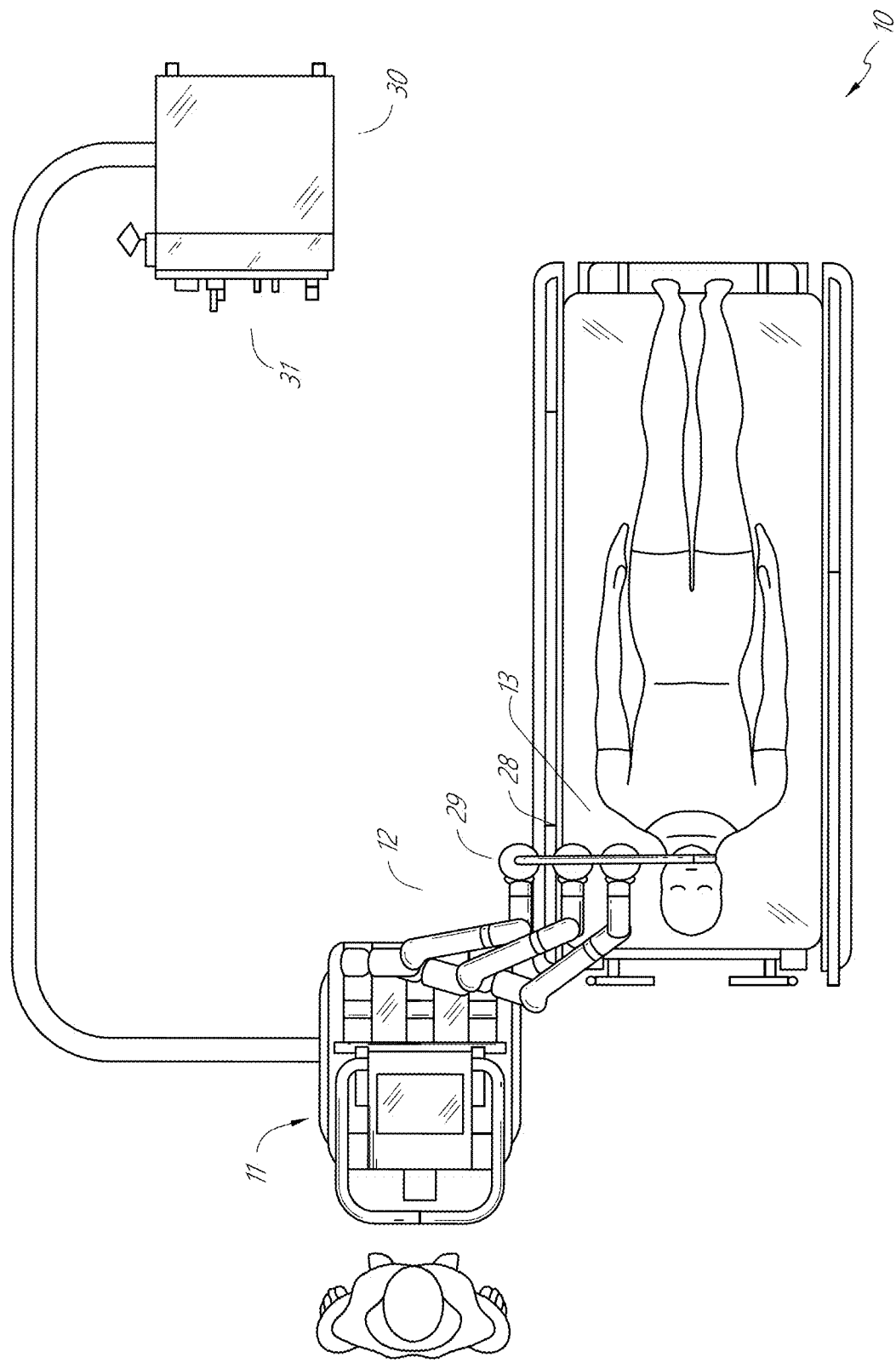
FIG. 1 illustrates an embodiment of a cart-based robotic system arranged for diagnostic and/or therapeutic bronchoscopy procedure(s).
Figure 2:
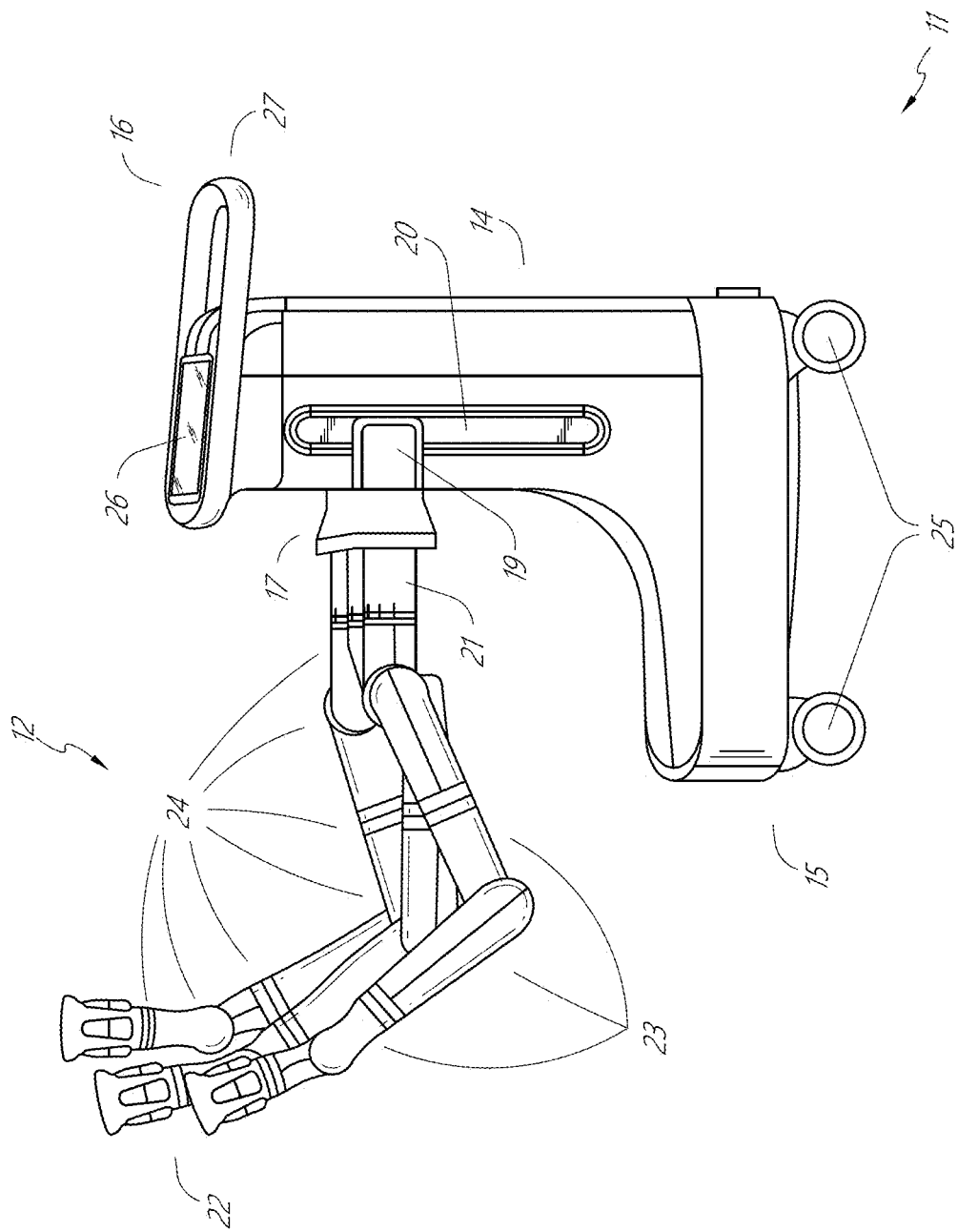
FIG. 2 depicts further aspects of the robotic system of FIG. 1.

The robotically-enabled medical system may be configured in a variety of ways depending on the particular procedure. FIG. 1 illustrates an embodiment of a cart-based robotically-enabled system 10 arranged for a diagnostic and/or therapeutic bronchoscopy procedure. During a bronchoscopy, the system 10 may comprise a cart 11 having one or more robotic arms 12 to deliver a medical instrument, such as a steerable endoscope 13, which may be a procedure-specific bronchoscope for bronchoscopy, to a natural orifice access point (i.e., the mouth of the patient positioned on a table in the present example) to deliver diagnostic and/or therapeutic tools. As shown, the cart 11 may be positioned proximate to the patient's upper torso in order to provide access to the access point. Similarly, the robotic arms 12 may be actuated to position the bronchoscope relative to the access point. The arrangement in FIG. 1 may also be utilized when performing a gastro-intestinal (GI) procedure with a gastroscope, a specialized endoscope for GI procedures. FIG. 2 depicts an example embodiment of the cart in greater detail.

With continued reference to FIG. 1, once the cart 11 is properly positioned, the robotic arms 12 may insert the steerable endoscope 13 into the patient robotically, manually, or a combination thereof. As shown, the steerable endoscope 13 may comprise at least two telescoping parts, such as an inner leader portion and an outer sheath portion, each portion coupled to a separate instrument driver from the set of instrument drivers 28, each instrument driver coupled to the distal end of an individual robotic arm. This linear arrangement of the instrument drivers 28, which facilitates coaxially aligning the leader portion with the sheath portion, creates a "virtual rail" 29 that may be repositioned in space by manipulating the one or more robotic arms 12 into different angles and/or positions. The virtual rails described herein are depicted in the Figures using dashed lines, and accordingly the dashed lines do not depict any physical structure of the system. Translation of the instrument drivers 28 along the virtual rail 29 telescopes the inner leader portion relative to the outer sheath portion or advances or retracts the endoscope 13 from the patient. The angle of the virtual rail 29 may be adjusted, translated, and pivoted based on clinical application or physician preference. For example, in bronchoscopy, the angle and position of the virtual rail 29 as shown represents a compromise between providing physician access to the endoscope 13 while minimizing friction that results from bending the endoscope 13 into the patient's mouth.

The endoscope 13 may be directed down the patient's trachea and lungs after insertion using precise commands from the robotic system until reaching the target destination or operative site. In order to enhance navigation through the patient's lung network and/or reach the desired target, the endoscope 13 may be manipulated to telescopically extend the inner leader portion from the outer sheath portion to obtain enhanced articulation and greater bend radius. The use of separate instrument drivers 28 also allows the leader portion and sheath portion to be driven independent of each other.

For example, the endoscope 13 may be directed to deliver a biopsy needle to a target, such as, for example, a lesion or nodule within the lungs of a patient. The needle may be deployed down a working channel that runs the length of the endoscope to obtain a tissue sample to be analyzed by a pathologist. Depending on the pathology results, additional tools may be deployed down the working channel of the endoscope for additional biopsies. After identifying a nodule to be malignant, the endoscope 13 may endoscopically deliver tools to resect the potentially cancerous tissue. In some instances, diagnostic and therapeutic treatments can be delivered in separate procedures. In those circumstances, the endoscope 13 may also be used to deliver a fiducial to "mark" the location of the target nodule as well. In other instances, diagnostic and therapeutic treatments may be delivered during the same procedure.

The system 10 may also include a movable tower 30, which may be connected via support cables to the cart 11 to provide support for controls, electronics, fluidics, optics, sensors, and/or power to the cart 11. Placing such functionality in the tower 30 allows for a smaller form factor cart 11 that may be more easily adjusted and/or re-positioned by an operating physician and his/her staff. Additionally, the division of functionality between the cart/table and the support tower 30 reduces operating room clutter and facilitates improving clinical workflow. While the cart 11 may be positioned close to the patient, the tower 30 may be stowed in a remote location to stay out of the way during a procedure.

In support of the robotic systems described above, the tower 30 may include component(s) of a computer-based control system that stores computer program instructions, for example, within a non-transitory computer-readable storage medium such as a persistent magnetic storage drive, solid state drive, etc. The execution of those instructions, whether the execution occurs in the tower 30 or the cart 11, may control the entire system or sub-system(s) thereof. For example, when executed by a processor of the computer system, the instructions may cause the components of the robotics system to actuate the relevant carriages and arm mounts, actuate the robotics arms, and control the medical instruments. For example, in response to receiving the control signal, the motors in the joints of the robotics arms may position the arms into a certain posture.

The tower 30 may also include a pump, flow meter, valve control, and/or fluid access in order to provide controlled irrigation and aspiration capabilities to the system that may be deployed through the endoscope 13. These components may also be controlled using the computer system of tower 30. In some embodiments, irrigation and aspiration capabilities may be delivered directly to the endoscope 13 through separate cable(s).

The tower 30 may include a voltage and surge protector designed to provide filtered and protected electrical power to the cart 11, thereby avoiding placement of a power transformer and other auxiliary power components in the cart 11, resulting in a smaller, more moveable cart 11.

The tower 30 may also include support equipment for the sensors deployed throughout the robotic system 10. For example, the tower 30 may include opto-electronics equipment for detecting, receiving, and processing data received from the optical sensors or cameras throughout the robotic system 10. In combination with the control system, such opto-electronics equipment may be used to generate real-time images for display in any number of consoles deployed throughout the system, including in the tower 30. Similarly, the tower 30 may also include an electronic subsystem for receiving and processing signals received from deployed electromagnetic (EM) sensors. The tower 30 may also be used to house and position an EM field generator for detection by EM sensors in or on the medical instrument.

The tower 30 may also include a console 31 in addition to other consoles available in the rest of the system, e.g., console mounted on top of the cart. The console 31 may include a user interface and a display screen, such as a touchscreen, for the physician operator. Consoles in system 10 are generally designed to provide both robotic controls as well as pre-operative and real-time information of the procedure, such as navigational and localization information of the endoscope 13. When the console 31 is not the only console available to the physician, it may be used by a second operator, such as a nurse, to monitor the health or vitals of the patient and the operation of system, as well as provide procedure-specific data, such as navigational and localization information. In other embodiments, the console 30 is housed in a body that is separate from the tower 30.

The tower 30 may be coupled to the cart 11 and endoscope 13 through one or more cables or connections (not shown). In some embodiments, the support functionality from the tower 30 may be provided through a single cable to the cart 11, simplifying and de-cluttering the operating room. In other embodiments, specific functionality may be coupled in separate cabling and connections. For example, while power may be provided through a single power cable to the cart, the support for controls, optics, fluidics, and/or navigation may be provided through a separate cable.

FIG. 2 provides a detailed illustration of an embodiment of the cart from the cart-based robotically-enabled system shown in FIG. 1. The cart 11 generally includes an elongated support structure 14 (often referred to as a "column"), a cart base 15, and a console 16 at the top of the column 14. The column 14 may include one or more carriages, such as a carriage 17 (alternatively "arm support") for supporting the deployment of one or more robotic arms 12 (three shown in FIG. 2). The carriage 17 may include individually configurable arm mounts that rotate along a perpendicular axis to adjust the base of the robotic arms 12 for better positioning relative to the patient. The carriage 17 also includes a carriage interface 19 that allows the carriage 17 to vertically translate along the column 14.

The carriage interface 19 is connected to the column 14 through slots, such as slot 20, that are positioned on opposite sides of the column 14 to guide the vertical translation of the carriage 17. The slot 20 contains a vertical translation interface to position and hold the carriage at various vertical heights relative to the cart base 15. Vertical translation of the carriage 17 allows the cart 11 to adjust the reach of the robotic arms 12 to meet a variety of table heights, patient sizes, and physician preferences. Similarly, the individually configurable arm mounts on the carriage 17 allow the robotic arm base 21 of robotic arms 12 to be angled in a variety of configurations.

In some embodiments, the slot 20 may be supplemented with slot covers that are flush and parallel to the slot surface to prevent dirt and fluid ingress into the internal chambers of the column 14 and the vertical translation interface as the carriage 17 vertically translates. The slot covers may be deployed through pairs of spring spools positioned near the vertical top and bottom of the slot 20. The covers are coiled within the spools until deployed to extend and retract from their coiled state as the carriage 17 vertically translates up and down. The spring-loading of the spools provides force to retract the cover into a spool when carriage 17 translates towards the spool, while also maintaining a tight seal when the carriage 17 translates away from the spool. The covers may be connected to the carriage 17 using, for example, brackets in the carriage interface 19 to ensure proper extension and retraction of the cover as the carriage 17 translates.

The column 14 may internally comprise mechanisms, such as gears and motors, that are designed to use a vertically aligned lead screw to translate the carriage 17 in a mechanized fashion in response to control signals generated in response to user inputs, e.g., inputs from the console 16.

The robotic arms 12 may generally comprise robotic arm bases 21 and end effectors 22, separated by a series of linkages 23 that are connected by a series of joints 24, each joint comprising an independent actuator, each actuator comprising an independently controllable motor. Each independently controllable joint represents an independent degree of freedom available to the robotic arm. Each of the arms 12 have seven joints, and thus provide seven degrees of freedom. A multitude of joints result in a multitude of degrees of freedom, allowing for "redundant" degrees of freedom. Redundant degrees of freedom allow the robotic arms 12 to position their respective end effectors 22 at a specific position, orientation, and trajectory in space using different linkage positions and joint angles. This allows for the system to position and direct a medical instrument from a desired point in space while allowing the physician to move the arm joints into a clinically advantageous position away from the patient to create greater access, while avoiding arm collisions.

The cart base 15 balances the weight of the column 14, carriage 17, and arms 12 over the floor. Accordingly, the cart base 15 houses heavier components, such as electronics, motors, power supply, as well as components that either enable movement and/or immobilize the cart. For example, the cart base 15 includes rollable wheel-shaped casters 25 that allow for the cart to easily move around the room prior to a procedure. After reaching the appropriate position, the casters 25 may be immobilized using wheel locks to hold the cart 11 in place during the procedure.

Positioned at the vertical end of column 14, the console 16 allows for both a user interface for receiving user input and a display screen (or a dual-purpose device such as, for example, a touchscreen 26) to provide the physician user with both pre-operative and intra-operative data. Potential pre-operative data on the touchscreen 26 may include pre-operative plans, navigation and mapping data derived from pre-operative computerized tomography (CT) scans, and/or notes from pre-operative patient interviews. Intra-operative data on display may include optical information provided from the tool, sensor and coordinate information from sensors, as well as vital patient statistics, such as respiration, heart rate, and/or pulse. The console 16 may be positioned and tilted to allow a physician to access the console from the side of the column 14 opposite carriage 17. From this position, the physician may view the console 16, robotic arms 12, and patient while operating the console 16 from behind the cart 11. As shown, the console 16 also includes a handle 27 to assist with maneuvering and stabilizing cart 11.

Figure 3:
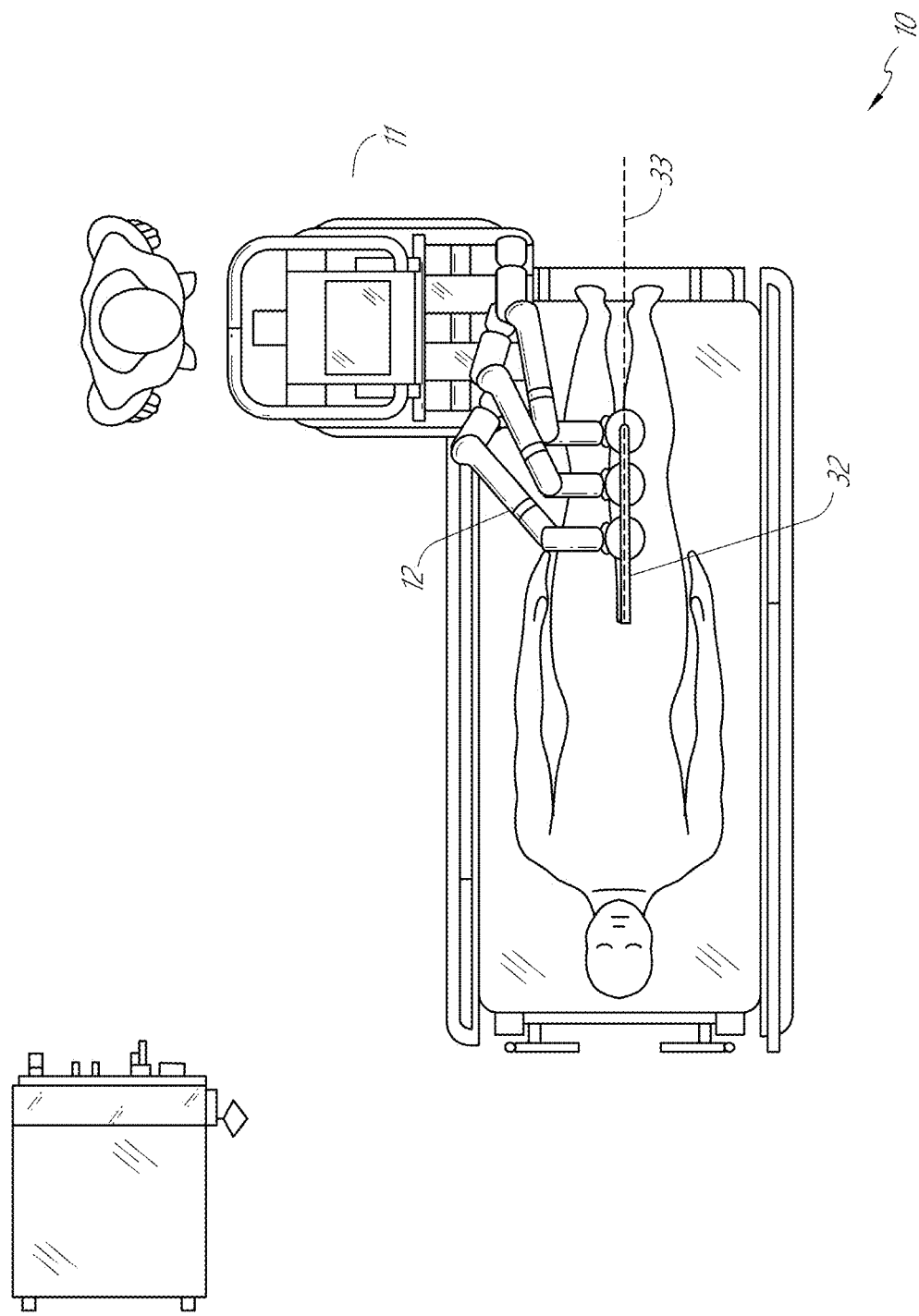
FIG. 3 illustrates an embodiment of the robotic system of FIG. 1 arranged for ureteroscopy.

FIG. 3 illustrates an embodiment of a robotically-enabled system 10 arranged for ureteroscopy. In a ureteroscopic procedure, the cart 11 may be positioned to deliver a ureteroscope 32, a procedure-specific endoscope designed to traverse a patient's urethra and ureter, to the lower abdominal area of the patient. In a ureteroscopy, it may be desirable for the ureteroscope 32 to be directly aligned with the patient's urethra to reduce friction and forces on the sensitive anatomy in the area. As shown, the cart 11 may be aligned at the foot of the table to allow the robotic arms 12 to position the ureteroscope 32 for direct linear access to the patient's urethra. From the foot of the table, the robotic arms 12 may insert the ureteroscope 32 along the virtual rail 33 directly into the patient's lower abdomen through the urethra.

After insertion into the urethra, using similar control techniques as in bronchoscopy, the ureteroscope 32 may be navigated into the bladder, ureters, and/or kidneys for diagnostic and/or therapeutic applications. For example, the ureteroscope 32 may be directed into the ureter and kidneys to break up kidney stone build up using a laser or ultrasonic lithotripsy device deployed down the working channel of the ureteroscope 32. After lithotripsy is complete, the resulting stone fragments may be removed using baskets deployed down the ureteroscope 32.

Figure 4:
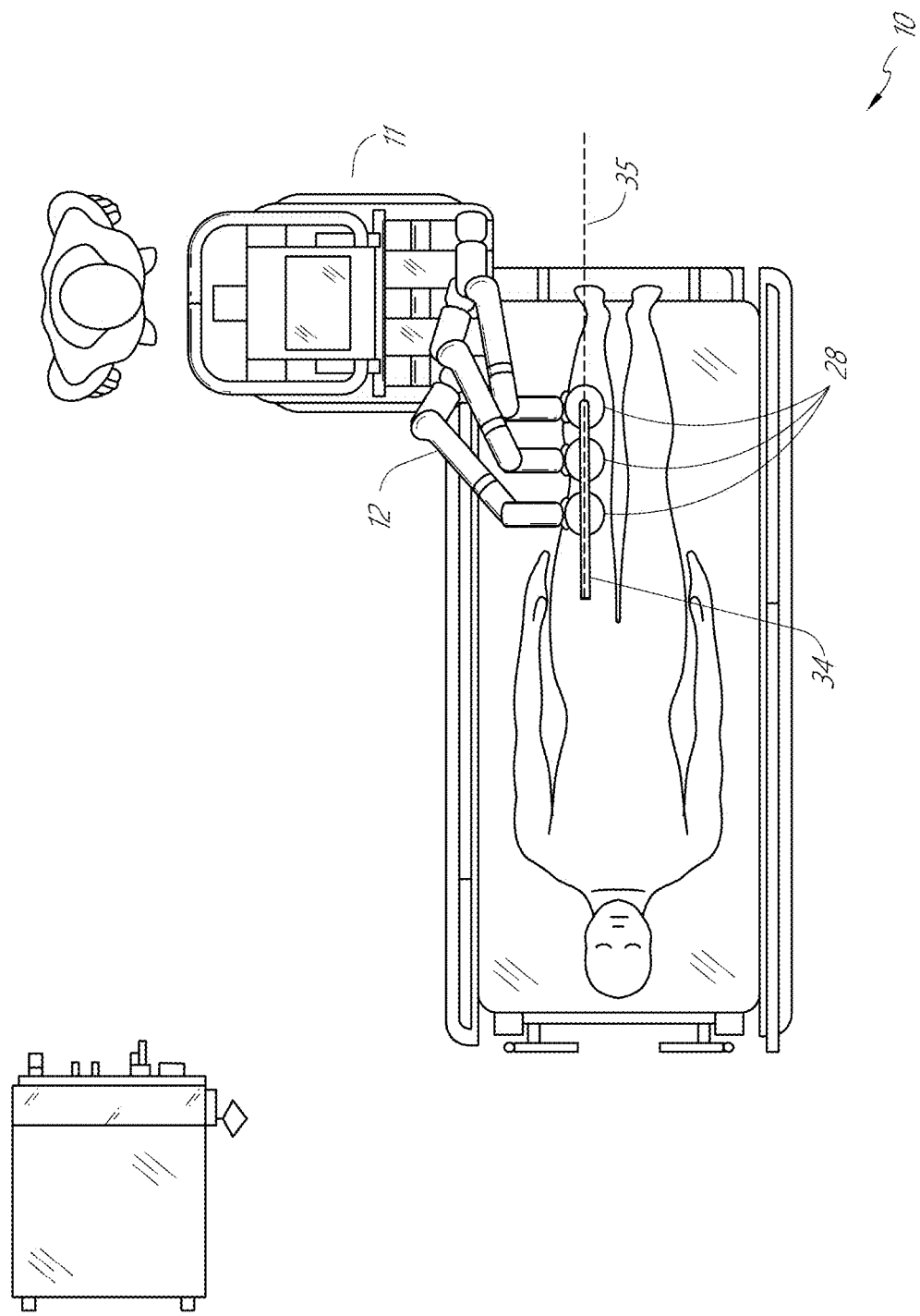
FIG. 4 illustrates an embodiment of the robotic system of FIG. 1 arranged for a vascular procedure.

FIG. 4 illustrates an embodiment of a robotically-enabled system similarly arranged for a vascular procedure. In a vascular procedure, the system 10 may be configured such that the cart 11 may deliver a medical instrument 34, such as a steerable catheter, to an access point in the femoral artery in the patient's leg. The femoral artery presents both a larger diameter for navigation as well as a relatively less circuitous and tortuous path to the patient's heart, which simplifies navigation. As in a ureteroscopic procedure, the cart 11 may be positioned towards the patient's legs and lower abdomen to allow the robotic arms 12 to provide a virtual rail 35 with direct linear access to the femoral artery access point in the patient's thigh/hip region. After insertion into the artery, the medical instrument 34 may be directed and inserted by translating the instrument drivers 28. Alternatively, the cart may be positioned around the patient's upper abdomen in order to reach alternative vascular access points, such as, for example, the carotid and brachial arteries near the shoulder and wrist.

B. Robotic System—Table

Figure 5:
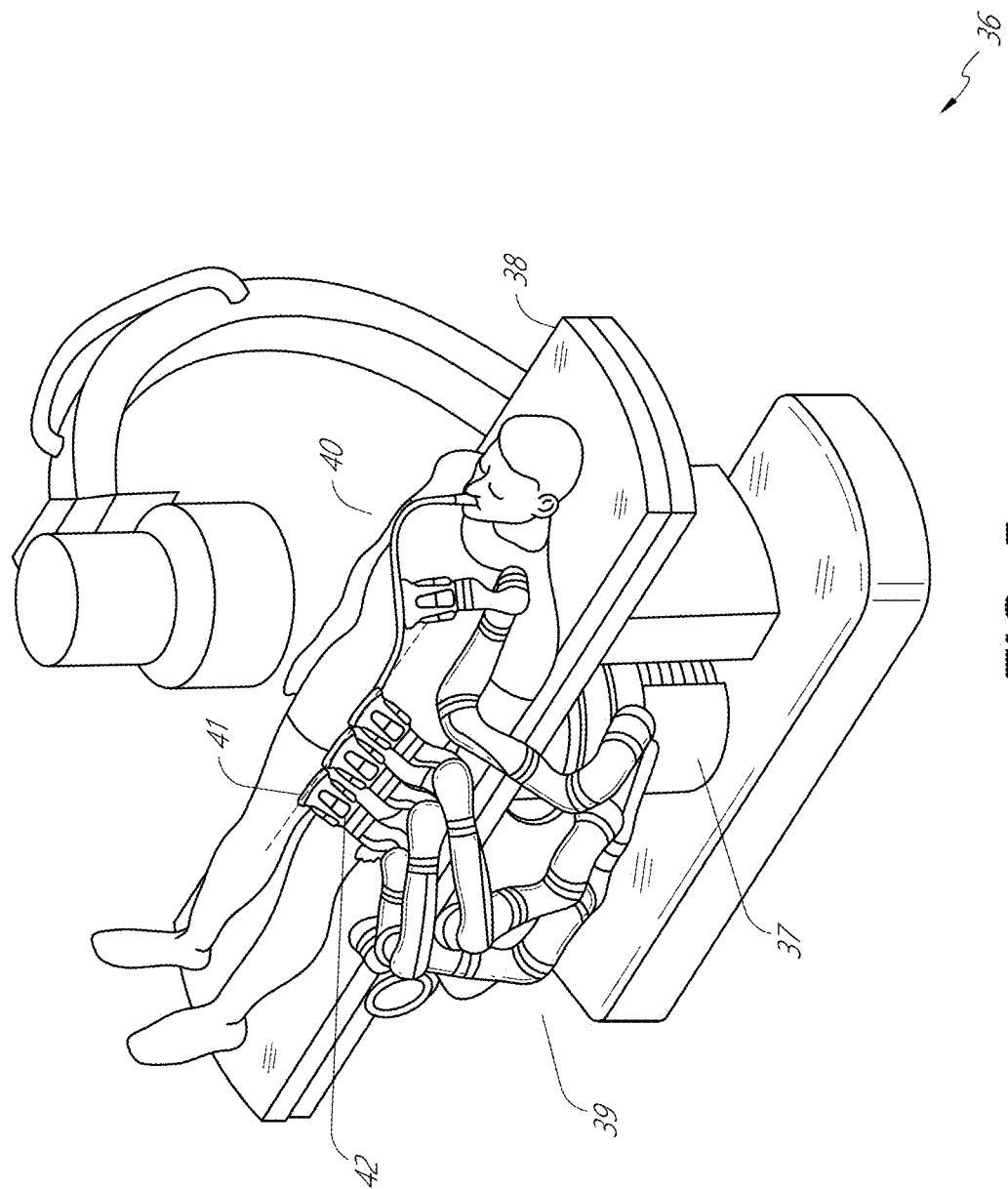
FIG. 5 illustrates an embodiment of a table-based robotic system arranged for a bronchoscopy procedure.

Embodiments of the robotically-enabled medical system may also incorporate the patient's table. Incorporation of the table reduces the amount of capital equipment within the operating room by removing the cart, which allows greater access to the patient. FIG. 5 illustrates an embodiment of such a robotically-enabled system arranged for a bronchoscopy procedure. System 36 includes a support structure or column 37 for supporting platform 38 (shown as a "table" or "bed") over the floor. Much like in the cart-based systems, the end effectors of the robotic arms 39 of the system 36 comprise instrument drivers 42 that are designed to manipulate an elongated medical instrument, such as a bronchoscope 40 in FIG. 5, through or along a virtual rail 41 formed from the linear alignment of the instrument drivers 42. In practice, a C-arm for providing fluoroscopic imaging may be positioned over the patient's upper abdominal area by placing the emitter and detector around table 38.

Figure 6:
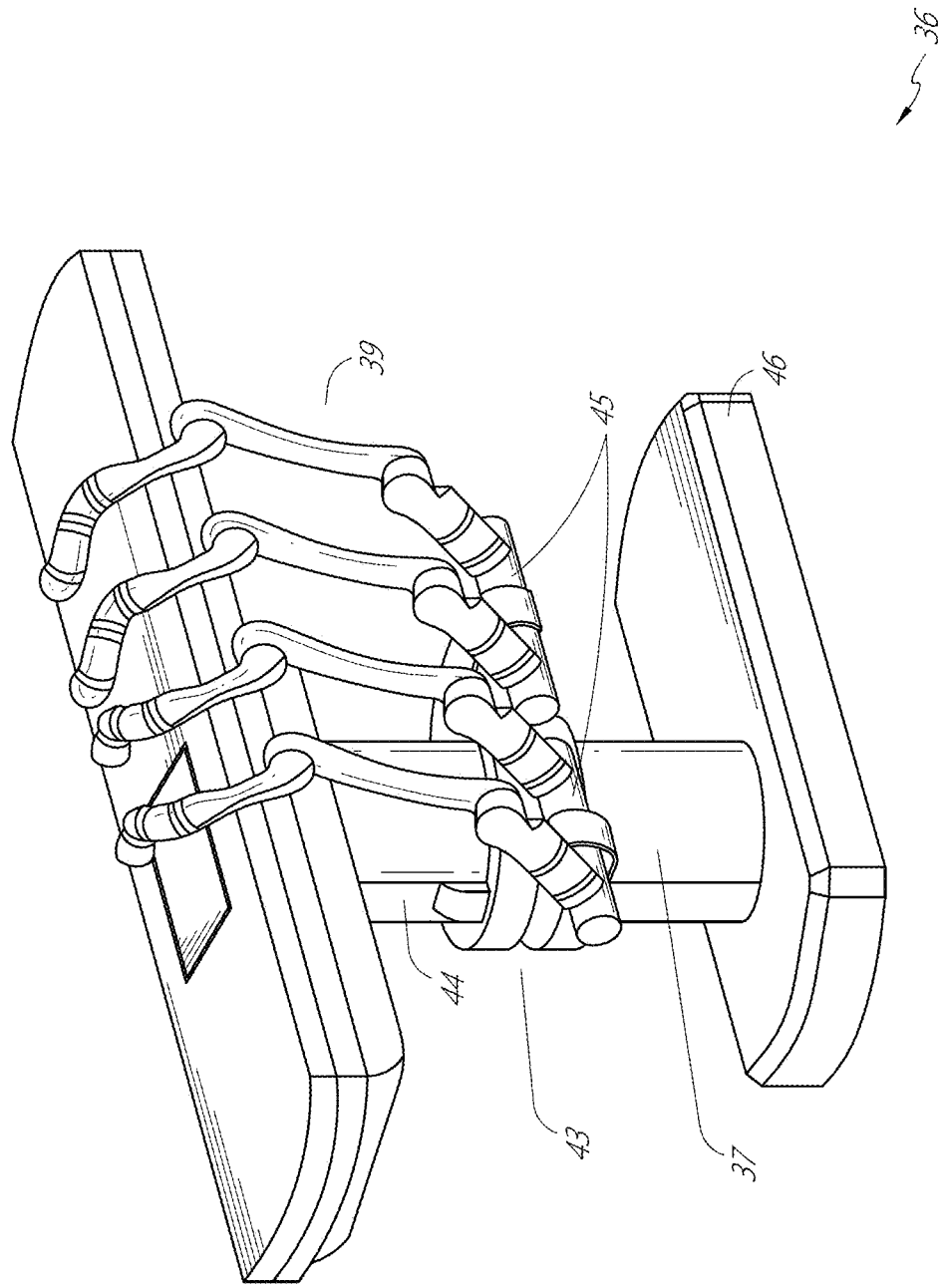
FIG. 6 provides an alternative view of the robotic system of FIG. 5.

FIG. 6 provides an alternative view of the system 36 without the patient and medical instrument for discussion purposes. As shown, the column 37 may include one or more carriages 43 shown as ring-shaped in the system 36, from which the one or more robotic arms 39 may be based. The carriages 43 may translate along a vertical column interface 44 that runs the length of the column 37 to provide different vantage points from which the robotic arms 39 may be positioned to reach the patient. The carriage(s) 43 may rotate around the column 37 using a mechanical motor positioned within the column 37 to allow the robotic arms 39 to have access to multiples sides of the table 38, such as, for example, both sides of the patient. In embodiments with multiple carriages, the carriages may be individually positioned on the column and may translate and/or rotate independent of the other carriages. While carriages 43 need not surround the column 37 or even be circular, the ring-shape as shown facilitates rotation of the carriages 43 around the column 37 while maintaining structural balance. Rotation and translation of the carriages 43 allows the system to align the medical instruments, such as endoscopes and laparoscopes, into different access points on the patient. In other embodiments (not shown), the system 36 can include a patient table or bed with adjustable arm supports in the form of bars or rails extending alongside it. One or more robotic arms 39 (e.g., via a shoulder with an elbow joint) can be attached to the adjustable arm supports, which can be vertically adjusted. By providing vertical adjustment, the robotic arms 39 are advantageously capable of being stowed compactly beneath the patient table or bed, and subsequently raised during a procedure.

Figure 9:
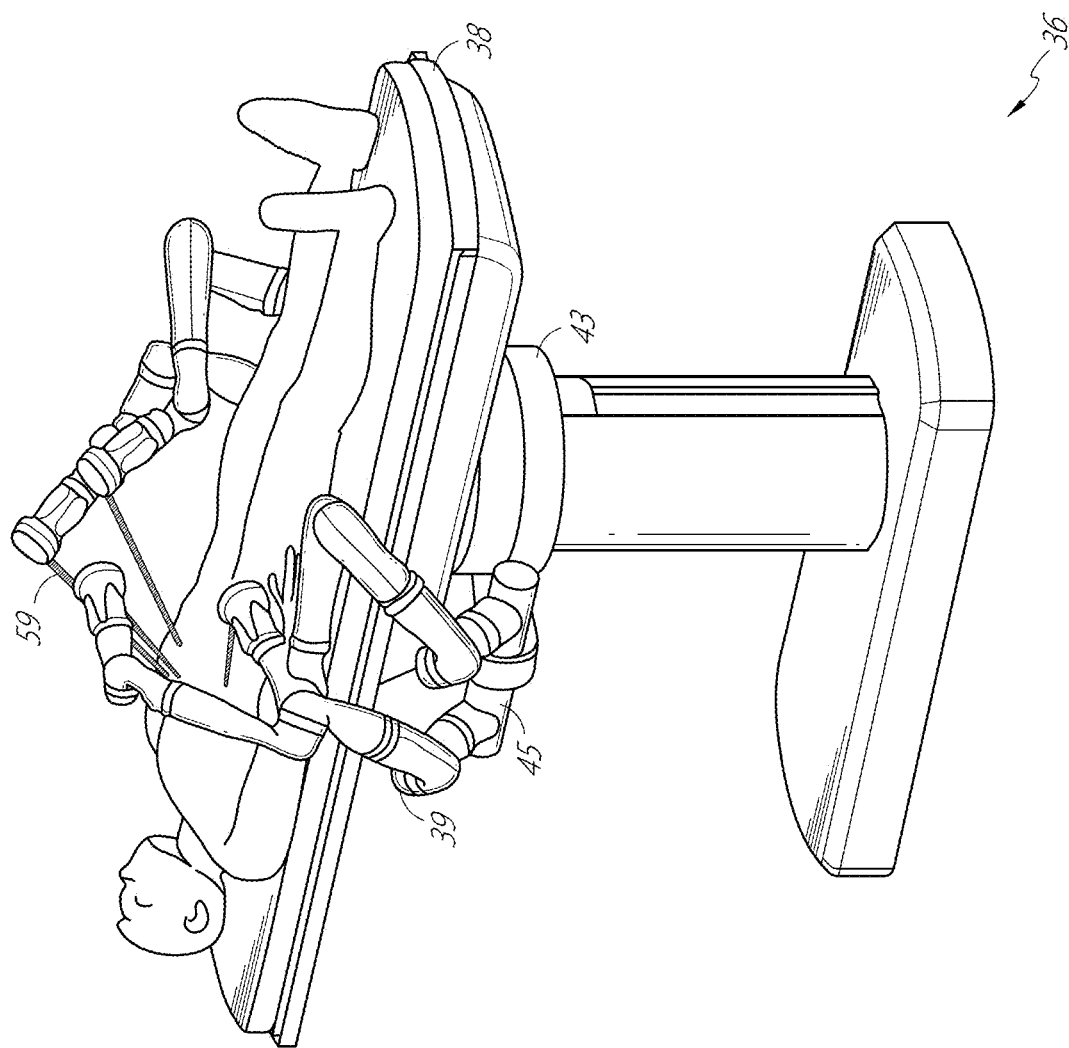
FIG. 9 illustrates an embodiment of a table-based robotic system configured for a laparoscopic procedure.

The arms 39 may be mounted on the carriages through a set of arm mounts 45 comprising a series of joints that may individually rotate and/or telescopically extend to provide additional configurability to the robotic arms 39. Additionally, the arm mounts 45 may be positioned on the carriages 43 such that, when the carriages 43 are appropriately rotated, the arm mounts 45 may be positioned on either the same side of table 38 (as shown in FIG. 6), on opposite sides of table 38 (as shown in FIG. 9), or on adjacent sides of the table 38 (not shown).

The column 37 structurally provides support for the table 38, and a path for vertical translation of the carriages. Internally, the column 37 may be equipped with lead screws for guiding vertical translation of the carriages, and motors to mechanize the translation of said carriages based the lead screws. The column 37 may also convey power and control signals to the carriage 43 and robotic arms 39 mounted thereon.

The table base 46 serves a similar function as the cart base 15 in cart 11 shown in FIG. 2, housing heavier components to balance the table/bed 38, the column 37, the carriages 43, and the robotic arms 39. The table base 46 may also incorporate rigid casters to provide stability during procedures. Deployed from the bottom of the table base 46, the casters may extend in opposite directions on both sides of the base 46 and retract when the system 36 needs to be moved.

Continuing with FIG. 6, the system 36 may also include a tower (not shown) that divides the functionality of system 36 between table and tower to reduce the form factor and bulk of the table. As in earlier disclosed embodiments, the tower may provide a variety of support functionalities to table, such as processing, computing, and control capabilities, power, fluidics, and/or optical and sensor processing. The tower may also be movable to be positioned away from the patient to improve physician access and de-clutter the operating room. Additionally, placing components in the tower allows for more storage space in the table base for potential stowage of the robotic arms. The tower may also include a master controller or console that provides both a user interface for user input, such as keyboard and/or pendant, as well as a display screen (or touchscreen) for pre-operative and intra-operative information, such as real-time imaging, navigation, and tracking information. In some embodiments, the tower may also contain holders for gas tanks to be used for insufflation.

Figure 7:
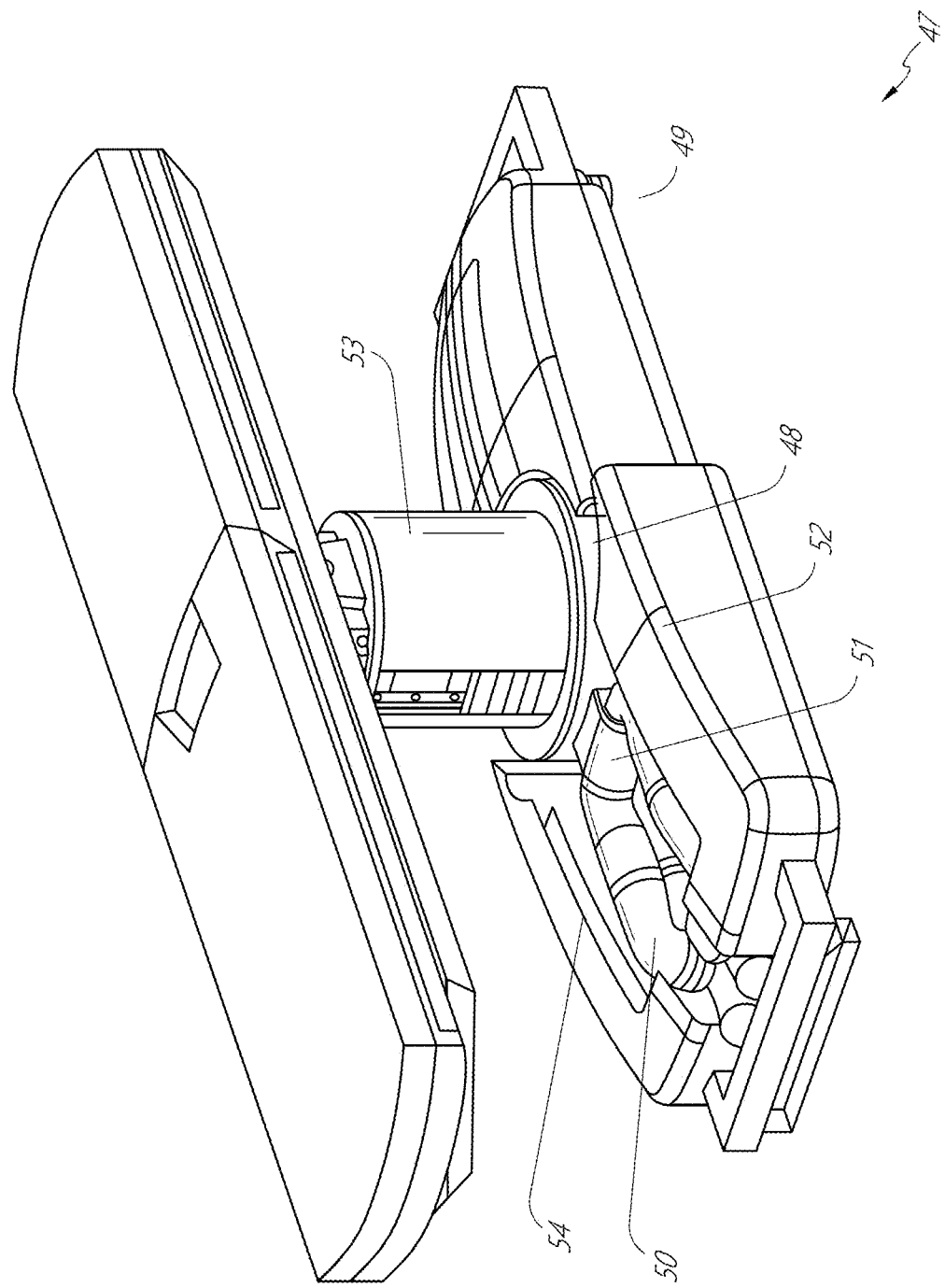
FIG. 7 illustrates an example system configured to stow robotic arm(s).

In some embodiments, a table base may stow and store the robotic arms when not in use. FIG. 7 illustrates a system 47 that stows robotic arms in an embodiment of the table-based system. In system 47, carriages 48 may be vertically translated into base 49 to stow robotic arms 50, arm mounts 51, and the carriages 48 within the base 49. Base covers 52 may be translated and retracted open to deploy the carriages 48, arm mounts 51, and arms 50 around column 53, and closed to stow to protect them when not in use. The base covers 52 may be sealed with a membrane 54 along the edges of its opening to prevent dirt and fluid ingress when closed.

Figure 8:
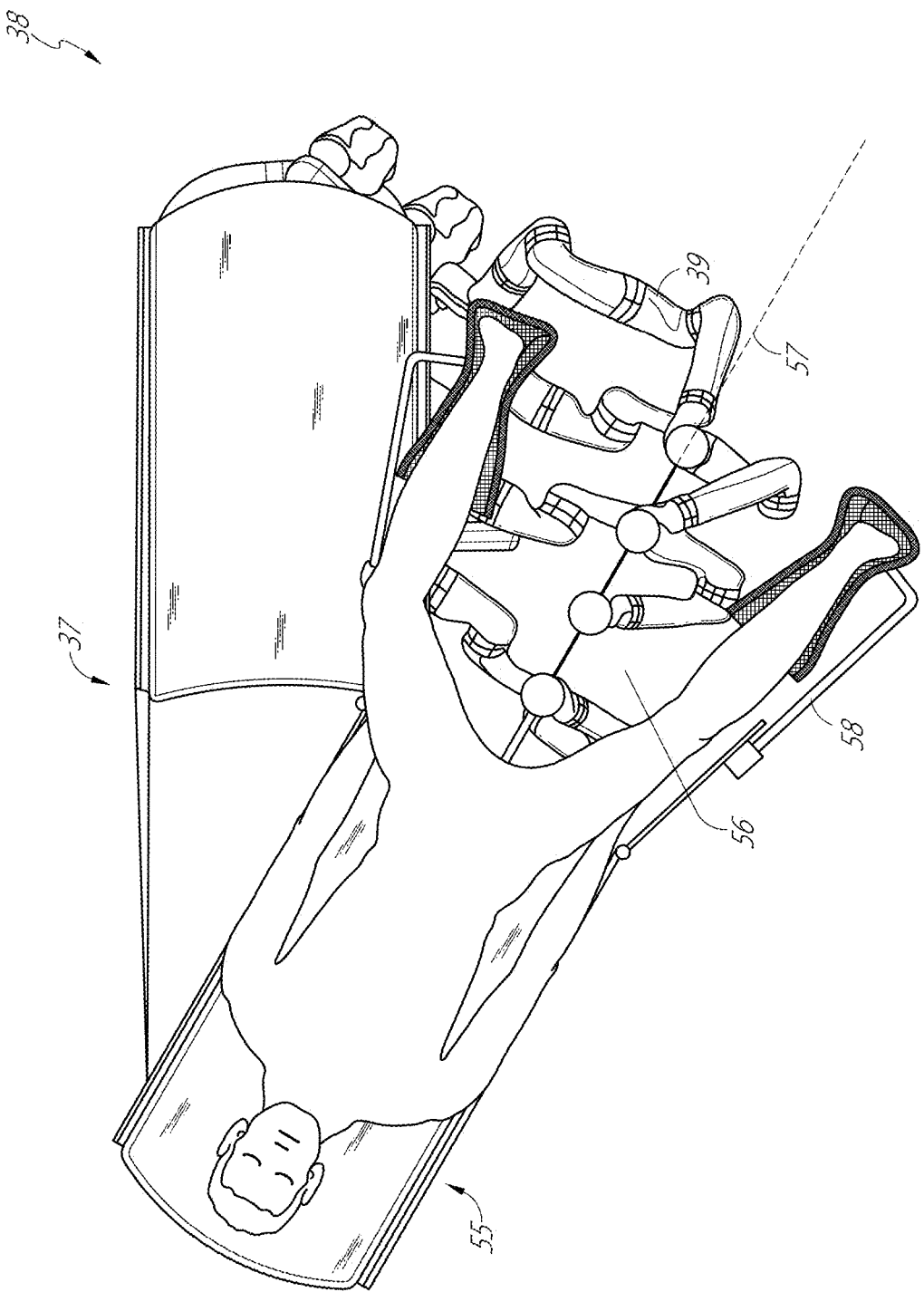
FIG. 8 illustrates an embodiment of a table-based robotic system configured for a ureteroscopy procedure.

FIG. 8 illustrates an embodiment of a robotically-enabled table-based system configured for a ureteroscopy procedure. In a ureteroscopy, the table 38 may include a swivel portion 55 for positioning a patient off-angle from the column 37 and table base 46. The swivel portion 55 may rotate or pivot around a pivot point (e.g., located below the patient's head) in order to position the bottom portion of the swivel portion 55 away from the column 37. For example, the pivoting of the swivel portion 55 allows a C-arm (not shown) to be positioned over the patient's lower abdomen without competing for space with the column (not shown) below table 38. By rotating the carriage 35 (not shown) around the column 37, the robotic arms 39 may directly insert a ureteroscope 56 along a virtual rail 57 into the patient's groin area to reach the urethra. In a ureteroscopy, stirrups 58 may also be fixed to the swivel portion 55 of the table 38 to support the position of the patient's legs during the procedure and allow clear access to the patient's groin area.

In a laparoscopic procedure, through small incision(s) in the patient's abdominal wall, minimally invasive instruments may be inserted into the patient's anatomy. In some embodiments, the minimally invasive instruments comprise an elongated rigid member, such as a shaft, which is used to access anatomy within the patient. After inflation of the patient's abdominal cavity, the instruments may be directed to perform surgical or medical tasks, such as grasping, cutting, ablating, suturing, etc. In some embodiments, the instruments can comprise a scope, such as a laparoscope. FIG. 9 illustrates an embodiment of a robotically-enabled table-based system configured for a laparoscopic procedure. As shown in FIG. 9, the carriages 43 of the system 36 may be rotated and vertically adjusted to position pairs of the robotic arms 39 on opposite sides of the table 38, such that instrument 59 may be positioned using the arm mounts 45 to be passed through minimal incisions on both sides of the patient to reach his/her abdominal cavity.

Figure 10:
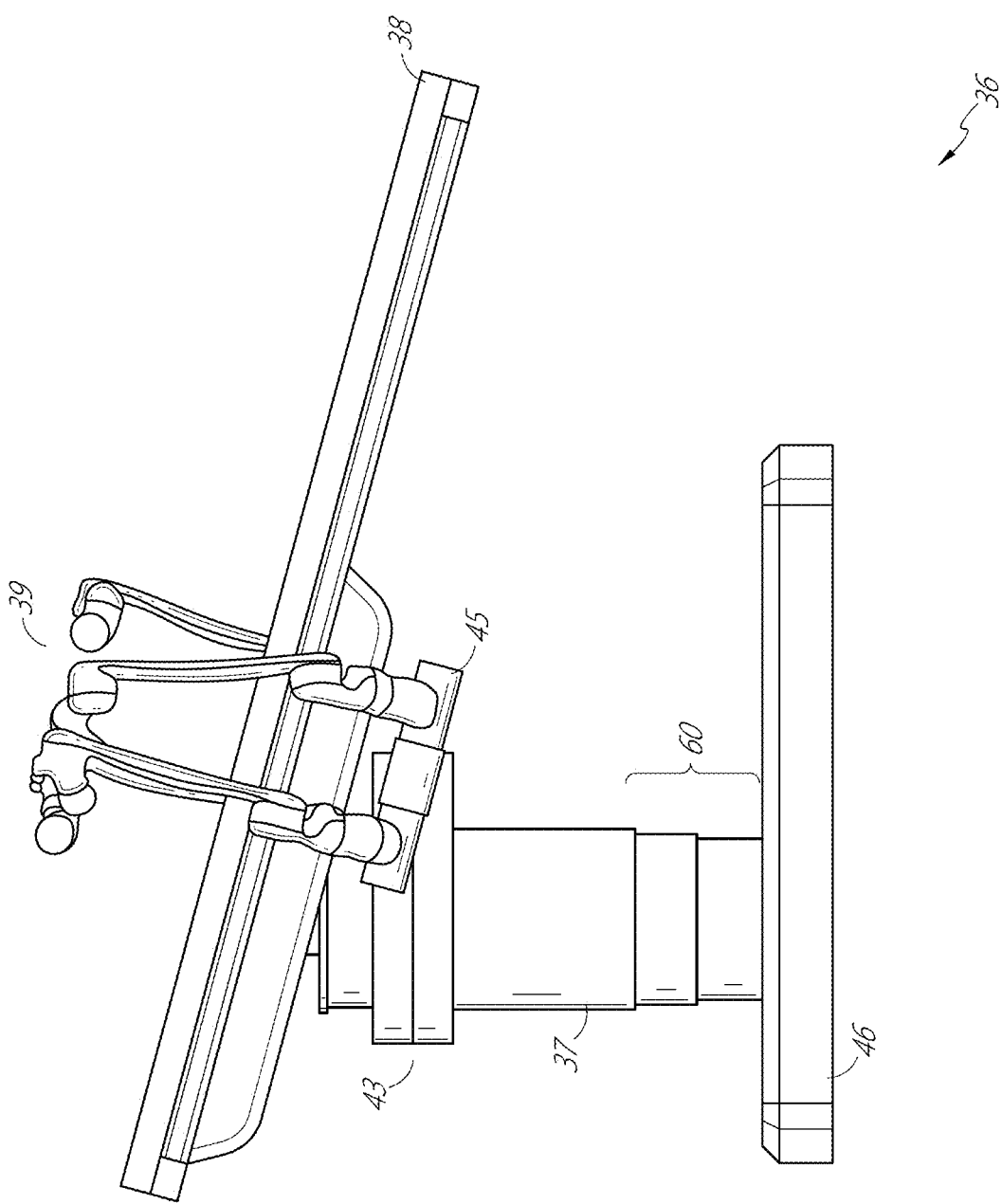
FIG. 10 illustrates an embodiment of the table-based robotic system of FIGS. 5-9 with pitch or tilt adjustment.

To accommodate laparoscopic procedures, the robotically-enabled table system may also tilt the platform to a desired angle. FIG. 10 illustrates an embodiment of the robotically-enabled medical system with pitch or tilt adjustment. As shown in FIG. 10, the system 36 may accommodate tilt of the table 38 to position one portion of the table at a greater distance from the floor than the other. Additionally, the arm mounts 45 may rotate to match the tilt such that the arms 39 maintain the same planar relationship with table 38. To accommodate steeper angles, the column 37 may also include telescoping portions 60 that allow vertical extension of column 37 to keep the table 38 from touching the floor or colliding with base 46.

Figure 11:
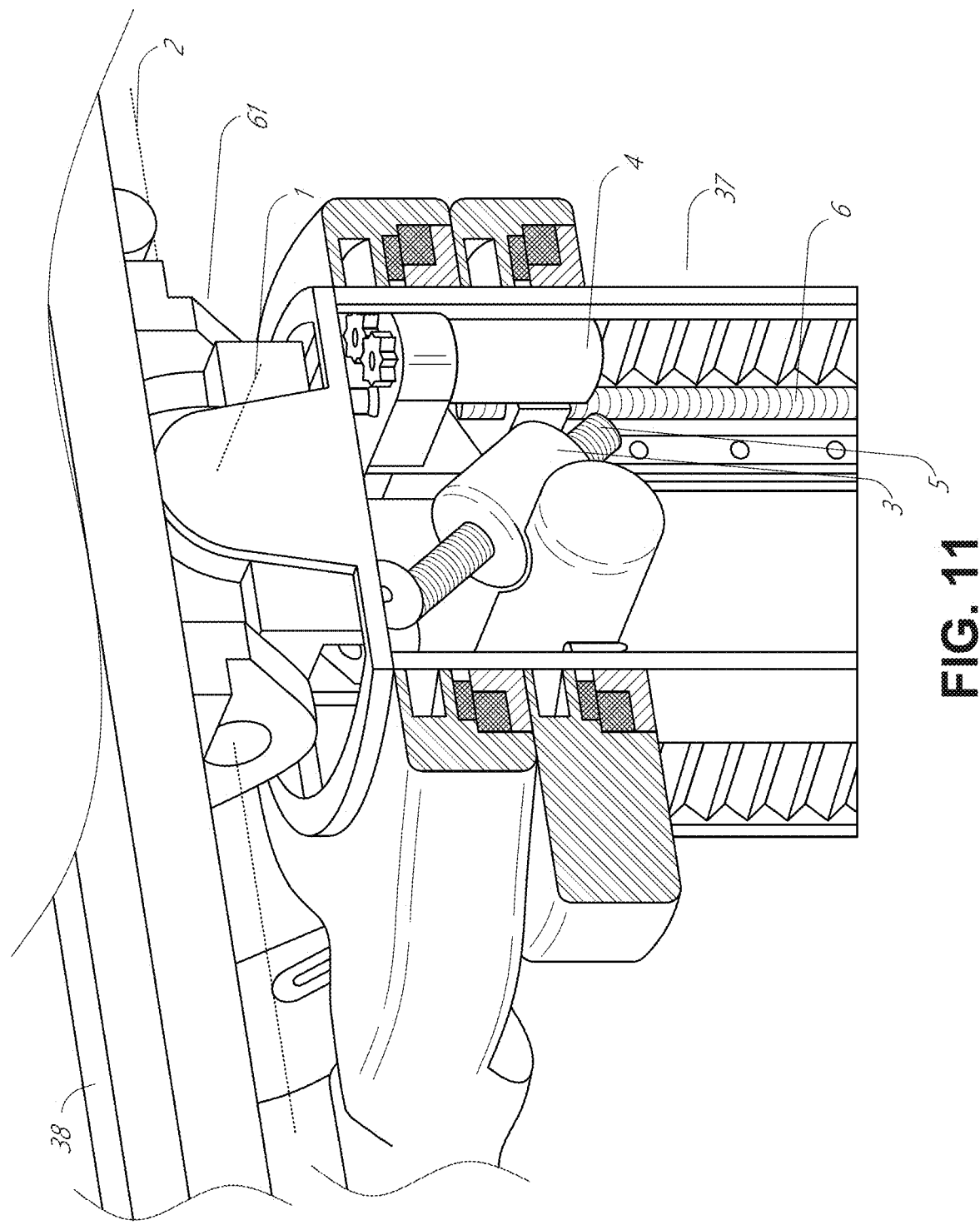
FIG. 11 provides a detailed illustration of the interface between the table and the column of the table-based robotic system of FIGS. 5-10.

FIG. 11 provides a detailed illustration of the interface between the table 38 and the column 37. Pitch rotation mechanism 61 may be configured to alter the pitch angle of the table 38 relative to the column 37 in multiple degrees of freedom. The pitch rotation mechanism 61 may be enabled by the positioning of orthogonal axes 1, 2 at the column-table interface, each axis actuated by a separate motor 3, 4 responsive to an electrical pitch angle command. Rotation along one screw 5 would enable tilt adjustments in one axis 1, while rotation along the other screw 6 would enable tilt adjustments along the other axis 2. In some embodiments, a ball joint can be used to alter the pitch angle of the table 38 relative to the column 37 in multiple degrees of freedom.

For example, pitch adjustments are particularly useful when trying to position the table in a Trendelenburg position, i.e., position the patient's lower abdomen at a higher position from the floor than the patient's lower abdomen, for lower abdominal surgery. The Trendelenburg position causes the patient's internal organs to slide towards his/her upper abdomen through the force of gravity, clearing out the abdominal cavity for minimally invasive tools to enter and perform lower abdominal surgical or medical procedures, such as laparoscopic prostatectomy.

Figure 12:
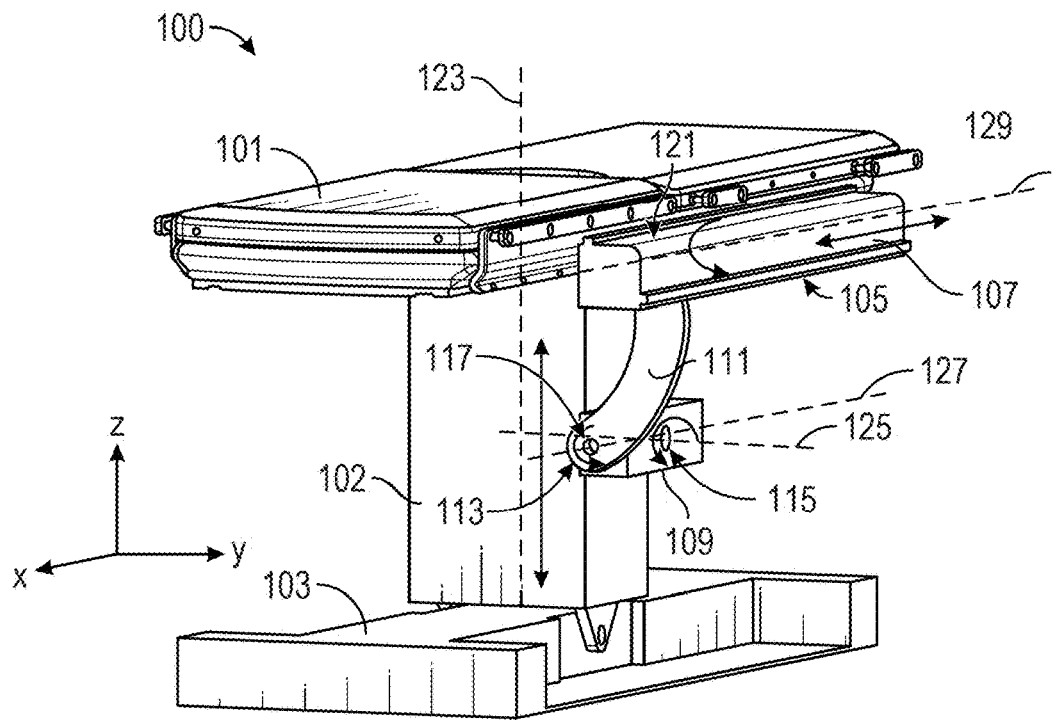
FIG. 12 illustrates an alternative embodiment of a table-based robotic system.
Figure 13:
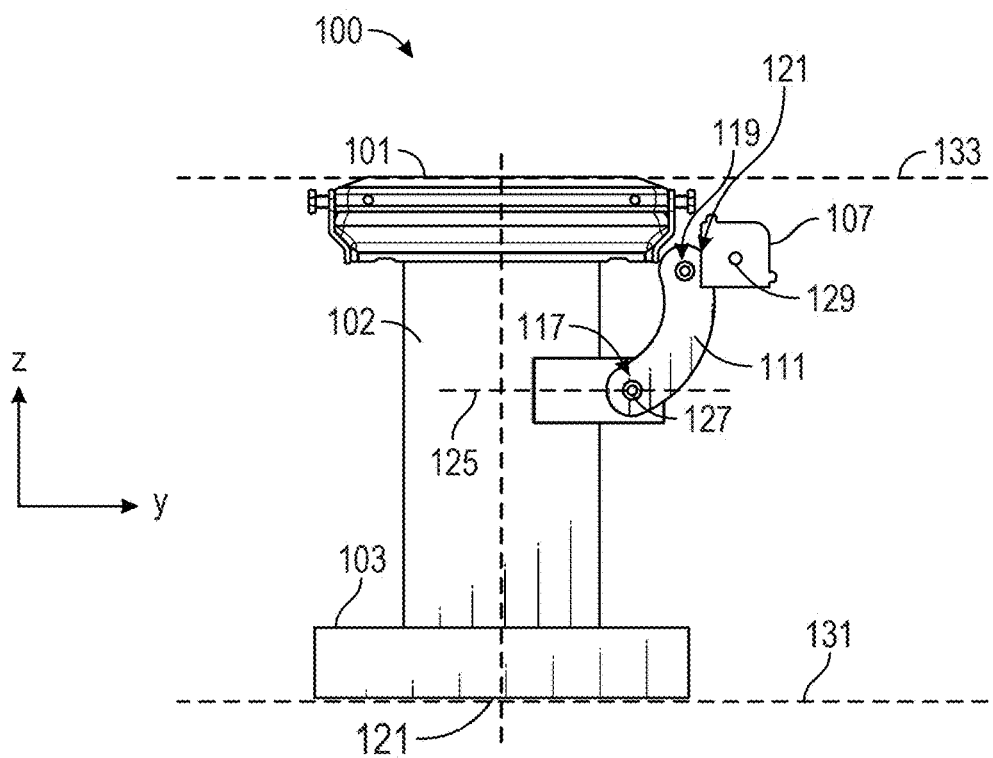
FIG. 13 illustrates an end view of the table-based robotic system of FIG. 12.

FIGS. 12 and 13 illustrate isometric and end views of an alternative embodiment of a table-based surgical robotics system 100. The surgical robotics system 100 includes one or more adjustable arm supports 105 that can be configured to support one or more robotic arms (see, for example, FIG. 14) relative to a table 101. In the illustrated embodiment, a single adjustable arm support 105 is shown, though an additional arm support can be provided on an opposite side of the table 101. The adjustable arm support 105 can be configured so that it can move relative to the table 101 to adjust and/or vary the position of the adjustable arm support 105 and/or any robotic arms mounted thereto relative to the table 101. For example, the adjustable arm support 105 may be adjusted one or more degrees of freedom relative to the table 101. The adjustable arm support 105 provides high versatility to the system 100, including the ability to easily stow the one or more adjustable arm supports 105 and any robotics arms attached thereto beneath the table 101. The adjustable arm support 105 can be elevated from the stowed position to a position below an upper surface of the table 101. In other embodiments, the adjustable arm support 105 can be elevated from the stowed position to a position above an upper surface of the table 101.

The adjustable arm support 105 can provide several degrees of freedom, including lift, lateral translation, tilt, etc. In the illustrated embodiment of FIGS. 12 and 13, the arm support 105 is configured with four degrees of freedom, which are illustrated with arrows in FIG. 12. A first degree of freedom allows for adjustment of the adjustable arm support 105 in the z-direction ("Z-lift"). For example, the adjustable arm support 105 can include a carriage 109 configured to move up or down along or relative to a column 102 supporting the table 101. A second degree of freedom can allow the adjustable arm support 105 to tilt. For example, the adjustable arm support 105 can include a rotary joint, which can allow the adjustable arm support 105 to be aligned with the bed in a Trendelenburg position. A third degree of freedom can allow the adjustable arm support 105 to "pivot up," which can be used to adjust a distance between a side of the table 101 and the adjustable arm support 105. A fourth degree of freedom can permit translation of the adjustable arm support 105 along a longitudinal length of the table.

The surgical robotics system 100 in FIGS. 12 and 13 can comprise a table supported by a column 102 that is mounted to a base 103. The base 103 and the column 102 support the table 101 relative to a support surface. A floor axis 131 and a support axis 133 are shown in FIG. 13.

The adjustable arm support 105 can be mounted to the column 102. In other embodiments, the arm support 105 can be mounted to the table 101 or base 103. The adjustable arm support 105 can include a carriage 109, a bar or rail connector 111 and a bar or rail 107. In some embodiments, one or more robotic arms mounted to the rail 107 can translate and move relative to one another.

The carriage 109 can be attached to the column 102 by a first joint 113, which allows the carriage 109 to move relative to the column 102 (e.g., such as up and down a first or vertical axis 123). The first joint 113 can provide the first degree of freedom ("Z-lift") to the adjustable arm support 105. The adjustable arm support 105 can include a second joint 115, which provides the second degree of freedom (tilt) for the adjustable arm support 105. The adjustable arm support 105 can include a third joint 117, which can provide the third degree of freedom ("pivot up") for the adjustable arm support 105. An additional joint 119 (shown in FIG. 13) can be provided that mechanically constrains the third joint 117 to maintain an orientation of the rail 107 as the rail connector 111 is rotated about a third axis 127. The adjustable arm support 105 can include a fourth joint 121, which can provide a fourth degree of freedom (translation) for the adjustable arm support 105 along a fourth axis 129.

Figure 14:
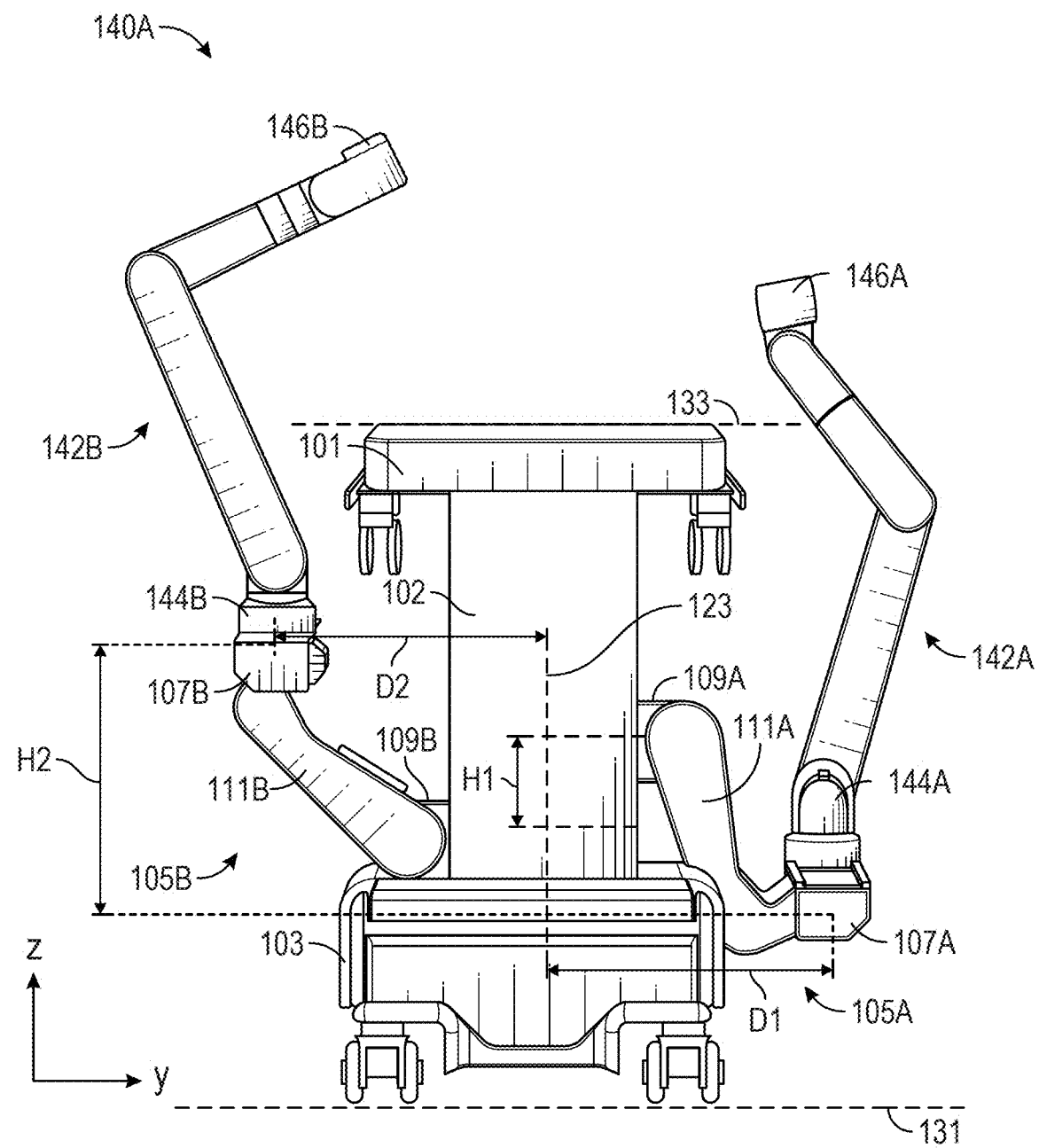
FIG. 14 illustrates an end view of a table-based robotic system with robotic arms attached thereto.

FIG. 14 illustrates an end view of the surgical robotics system 140A with two adjustable arm supports 105A, 105B mounted on opposite sides of a table 101. A first robotic arm 142A is attached to the bar or rail 107A of the first adjustable arm support 105B. The first robotic arm 142A includes a base 144A attached to the rail 107A. The distal end of the first robotic arm 142A includes an instrument drive mechanism 146A that can attach to one or more robotic medical instruments or tools. Similarly, the second robotic arm 142B includes a base 144B attached to the rail 107B. The distal end of the second robotic arm 142B includes an instrument drive mechanism 146B. The instrument drive mechanism 146B can be configured to attach to one or more robotic medical instruments or tools.

In some embodiments, one or more of the robotic arms 142A, 142B comprises an arm with seven or more degrees of freedom. In some embodiments, one or more of the robotic arms 142A, 142B can include eight degrees of freedom, including an insertion axis (1-degree of freedom including insertion), a wrist (3-degrees of freedom including wrist pitch, yaw and roll), an elbow (1-degree of freedom including elbow pitch), a shoulder (2-degrees of freedom including shoulder pitch and yaw), and base 144A, 144B (1-degree of freedom including translation). In some embodiments, the insertion degree of freedom can be provided by the robotic arm 142A, 142B, while in other embodiments, the instrument itself provides insertion via an instrument-based insertion architecture.

C. Instrument Driver & Interface

The end effectors of the system's robotic arms comprise (i) an instrument driver (alternatively referred to as "instrument drive mechanism" or "instrument device manipulator") that incorporate electro-mechanical means for actuating the medical instrument and (ii) a removable or detachable medical instrument, which may be devoid of any electro-mechanical components, such as motors. This dichotomy may be driven by the need to sterilize medical instruments used in medical procedures, and the inability to adequately sterilize expensive capital equipment due to their intricate mechanical assemblies and sensitive electronics. Accordingly, the medical instruments may be designed to be detached, removed, and interchanged from the instrument driver (and thus the system) for individual sterilization or disposal by the physician or the physician's staff. In contrast, the instrument drivers need not be changed or sterilized, and may be draped for protection.

Figure 15:
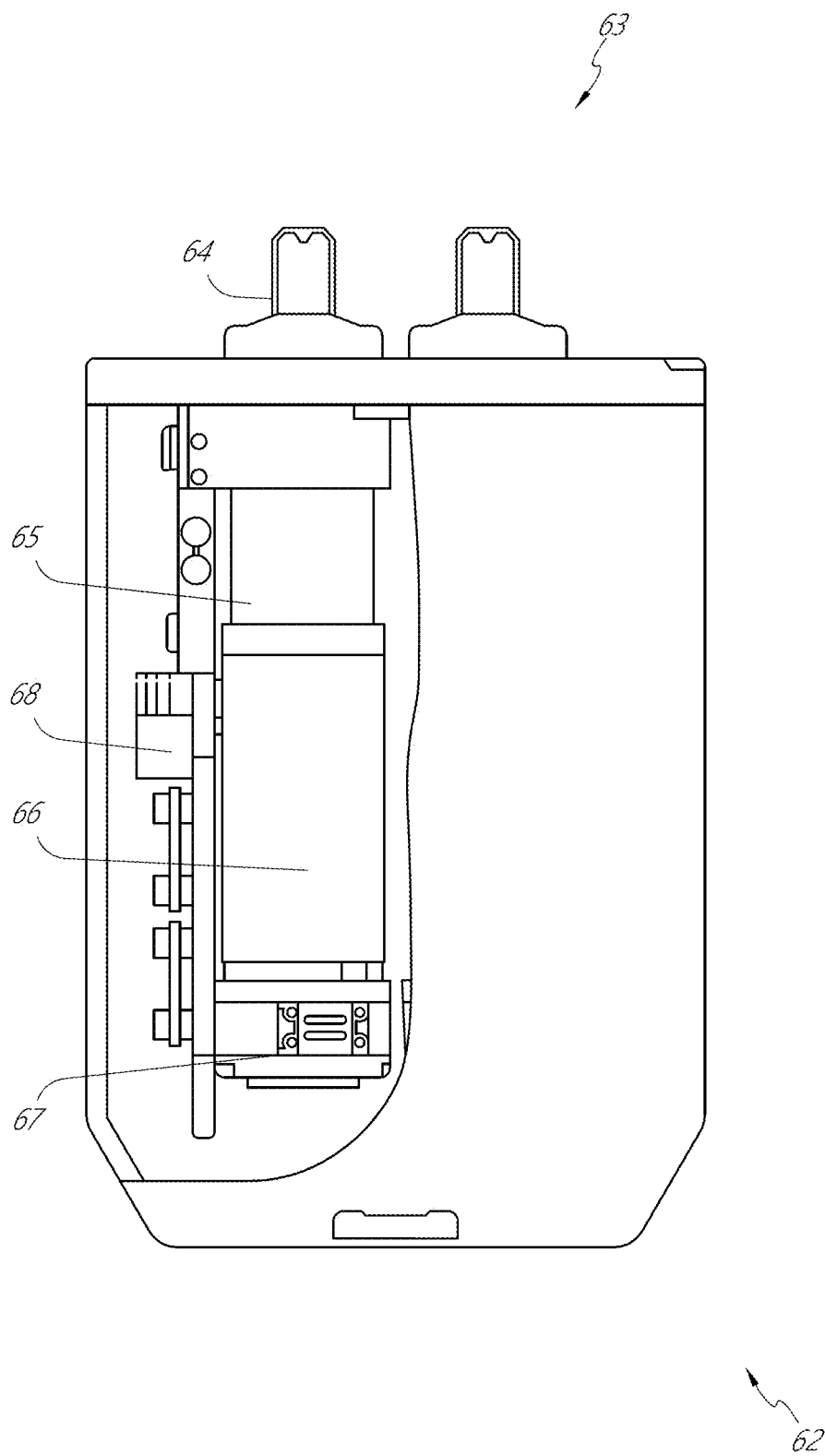
FIG. 15 illustrates an exemplary instrument driver.

FIG. 15 illustrates an example instrument driver. Positioned at the distal end of a robotic arm, instrument driver 62 comprises of one or more drive units 63 arranged with parallel axes to provide controlled torque to a medical instrument via drive shafts 64. Each drive unit 63 comprises an individual drive shaft 64 for interacting with the instrument, a gear head 65 for converting the motor shaft rotation to a desired torque, a motor 66 for generating the drive torque, an encoder 67 to measure the speed of the motor shaft and provide feedback to the control circuitry, and control circuity 68 for receiving control signals and actuating the drive unit. Each drive unit 63 being independent controlled and motorized, the instrument driver 62 may provide multiple (e.g., four as shown in FIG. 15) independent drive outputs to the medical instrument. In operation, the control circuitry 68 would receive a control signal, transmit a motor signal to the motor 66, compare the resulting motor speed as measured by the encoder 67 with the desired speed, and modulate the motor signal to generate the desired torque.

For procedures that require a sterile environment, the robotic system may incorporate a drive interface, such as a sterile adapter connected to a sterile drape, that sits between the instrument driver and the medical instrument. The chief purpose of the sterile adapter is to transfer angular motion from the drive shafts of the instrument driver to the drive inputs of the instrument while maintaining physical separation, and thus sterility, between the drive shafts and drive inputs. Accordingly, an example sterile adapter may comprise of a series of rotational inputs and outputs intended to be mated with the drive shafts of the instrument driver and drive inputs on the instrument. Connected to the sterile adapter, the sterile drape, comprised of a thin, flexible material such as transparent or translucent plastic, is designed to cover the capital equipment, such as the instrument driver, robotic arm, and cart (in a cart-based system) or table (in a table-based system). Use of the drape would allow the capital equipment to be positioned proximate to the patient while still being located in an area not requiring sterilization (i.e., non-sterile field). On the other side of the sterile drape, the medical instrument may interface with the patient in an area requiring sterilization (i.e., sterile field).

D. Medical Instrument

Figure 16:
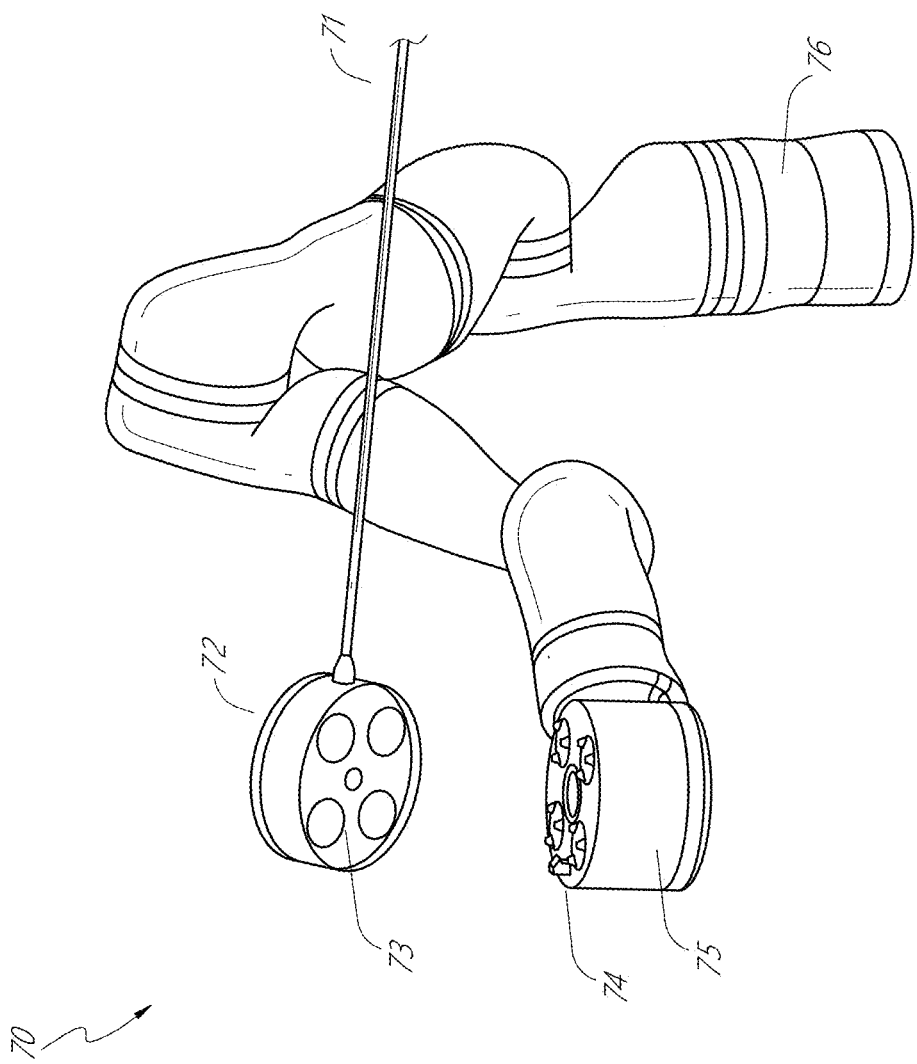
FIG. 16 illustrates an exemplary medical instrument with a paired instrument driver.

FIG. 16 illustrates an example medical instrument with a paired instrument driver. Like other instruments designed for use with a robotic system, medical instrument 70 comprises an elongated shaft 71 (or elongate body) and an instrument base 72. The instrument base 72, also referred to as an "instrument handle" due to its intended design for manual interaction by the physician, may generally comprise rotatable drive inputs 73, e.g., receptacles, pulleys or spools, that are designed to be mated with drive outputs 74 that extend through a drive interface on instrument driver 75 at the distal end of robotic arm 76. When physically connected, latched, and/or coupled, the mated drive inputs 73 of instrument base 72 may share axes of rotation with the drive outputs 74 in the instrument driver 75 to allow the transfer of torque from drive outputs 74 to drive inputs 73. In some embodiments, the drive outputs 74 may comprise splines that are designed to mate with receptacles on the drive inputs 73.

The elongated shaft 71 is designed to be delivered through either an anatomical opening or lumen, e.g., as in endoscopy, or a minimally invasive incision, e.g., as in laparoscopy. The elongated shaft 71 may be either flexible (e.g., having properties similar to an endoscope) or rigid (e.g., having properties similar to a laparoscope) or contain a customized combination of both flexible and rigid portions. When designed for laparoscopy, the distal end of a rigid elongated shaft may be connected to an end effector extending from a jointed wrist formed from a clevis with at least one degree of freedom and a surgical tool or medical instrument, such as, for example, a grasper or scissors, that may be actuated based on force from the tendons as the drive inputs rotate in response to torque received from the drive outputs 74 of the instrument driver 75. When designed for endoscopy, the distal end of a flexible elongated shaft may include a steerable or controllable bending section that may be articulated and bent based on torque received from the drive outputs 74 of the instrument driver 75.

Torque from the instrument driver 75 is transmitted down the elongated shaft 71 using tendons along the shaft 71. These individual tendons, such as pull wires, may be individually anchored to individual drive inputs 73 within the instrument handle 72. From the handle 72, the tendons are directed down one or more pull lumens along the elongated shaft 71 and anchored at the distal portion of the elongated shaft 71, or in the wrist at the distal portion of the elongated shaft. During a surgical procedure, such as a laparoscopic, endoscopic or hybrid procedure, these tendons may be coupled to a distally mounted end effector, such as a wrist, grasper, or scissor. Under such an arrangement, torque exerted on drive inputs 73 would transfer tension to the tendon, thereby causing the end effector to actuate in some way. In some embodiments, during a surgical procedure, the tendon may cause a joint to rotate about an axis, thereby causing the end effector to move in one direction or another. Alternatively, the tendon may be connected to one or more jaws of a grasper at distal end of the elongated shaft 71, where tension from the tendon cause the grasper to close.

In endoscopy, the tendons may be coupled to a bending or articulating section positioned along the elongated shaft 71 (e.g., at the distal end) via adhesive, control ring, or other mechanical fixation. When fixedly attached to the distal end of a bending section, torque exerted on drive inputs 73 would be transmitted down the tendons, causing the softer, bending section (sometimes referred to as the articulable section or region) to bend or articulate. Along the non-bending sections, it may be advantageous to spiral or helix the individual pull lumens that direct the individual tendons along (or inside) the walls of the endoscope shaft to balance the radial forces that result from tension in the pull wires. The angle of the spiraling and/or spacing there between may be altered or engineered for specific purposes, wherein tighter spiraling exhibits lesser shaft compression under load forces, while lower amounts of spiraling results in greater shaft compression under load forces, but also exhibits limits bending. On the other end of the spectrum, the pull lumens may be directed parallel to the longitudinal axis of the elongated shaft 71 to allow for controlled articulation in the desired bending or articulable sections.

In endoscopy, the elongated shaft 71 houses a number of components to assist with the robotic procedure. The shaft may comprise of a working channel for deploying surgical tools (or medical instruments), irrigation, and/or aspiration to the operative region at the distal end of the shaft 71. The shaft 71 may also accommodate wires and/or optical fibers to transfer signals to/from an optical assembly at the distal tip, which may include of an optical camera. The shaft 71 may also accommodate optical fibers to carry light from proximally-located light sources, such as light emitting diodes, to the distal end of the shaft.

At the distal end of the instrument 70, the distal tip may also comprise the opening of a working channel for delivering tools for diagnostic and/or therapy, irrigation, and aspiration to an operative site. The distal tip may also include a port for a camera, such as a fiberscope or a digital camera, to capture images of an internal anatomical space. Relatedly, the distal tip may also include ports for light sources for illuminating the anatomical space when using the camera.

In the example of FIG. 16, the drive shaft axes, and thus the drive input axes, are orthogonal to the axis of the elongated shaft. This arrangement, however, complicates roll capabilities for the elongated shaft 71. Rolling the elongated shaft 71 along its axis while keeping the drive inputs 73 static results in undesirable tangling of the tendons as they extend off the drive inputs 73 and enter pull lumens within the elongated shaft 71. The resulting entanglement of such tendons may disrupt any control algorithms intended to predict movement of the flexible elongated shaft during an endoscopic procedure.

Figure 17:
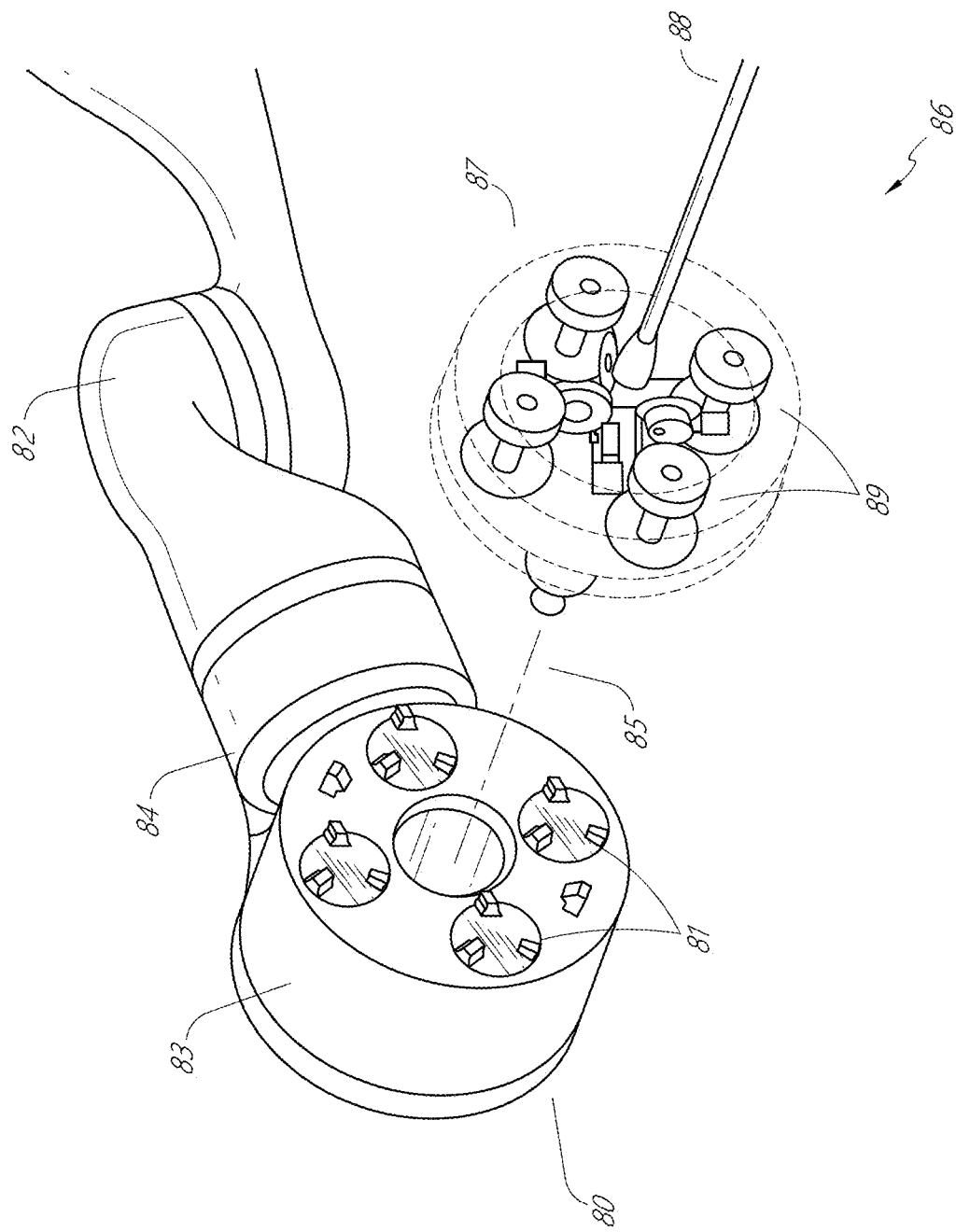
FIG. 17 illustrates an alternative design for an instrument driver and instrument where the axes of the drive units are parallel to the axis of the elongated shaft of the instrument.

FIG. 17 illustrates an alternative design for an instrument driver and instrument where the axes of the drive units are parallel to the axis of the elongated shaft of the instrument. As shown, a circular instrument driver 80 comprises four drive units with their drive outputs 81 aligned in parallel at the end of a robotic arm 82. The drive units, and their respective drive outputs 81, are housed in a rotational assembly 83 of the instrument driver 80 that is driven by one of the drive units within the assembly 83. In response to torque provided by the rotational drive unit, the rotational assembly 83 rotates along a circular bearing that connects the rotational assembly 83 to the non-rotational portion 84 of the instrument driver. Power and controls signals may be communicated from the non-rotational portion 84 of the instrument driver 80 to the rotational assembly 83 through electrical contacts may be maintained through rotation by a brushed slip ring connection (not shown). In other embodiments, the rotational assembly 83 may be responsive to a separate drive unit that is integrated into the non-rotatable portion 84, and thus not in parallel to the other drive units.

The rotational mechanism 83 allows the instrument driver 80 to rotate the drive units, and their respective drive outputs 81, as a single unit around an instrument driver axis 85.

Like earlier disclosed embodiments, an instrument 86 may comprise an elongated shaft portion 88 and an instrument base 87 (shown with a transparent external skin for discussion purposes) comprising a plurality of drive inputs 89 (such as receptacles, pulleys, and spools) that are configured to receive the drive outputs 81 in the instrument driver 80. Unlike prior disclosed embodiments, instrument shaft 88 extends from the center of instrument base 87 with an axis substantially parallel to the axes of the drive inputs 89, rather than orthogonal as in the design of FIG. 16.

When coupled to the rotational assembly 83 of the instrument driver 80, the medical instrument 86, comprising instrument base 87 and instrument shaft 88, rotates in combination with the rotational assembly 83 about the instrument driver axis 85. Since the instrument shaft 88 is positioned at the center of instrument base 87, the instrument shaft 88 is coaxial with instrument driver axis 85 when attached. Thus, rotation of the rotational assembly 83 causes the instrument shaft 88 to rotate about its own longitudinal axis. Moreover, as the instrument base 87 rotates with the instrument shaft 88, any tendons connected to the drive inputs 89 in the instrument base 87 are not tangled during rotation. Accordingly, the parallelism of the axes of the drive outputs 81, drive inputs 89, and instrument shaft 88 allows for the shaft rotation without tangling any control tendons.

Figure 18:
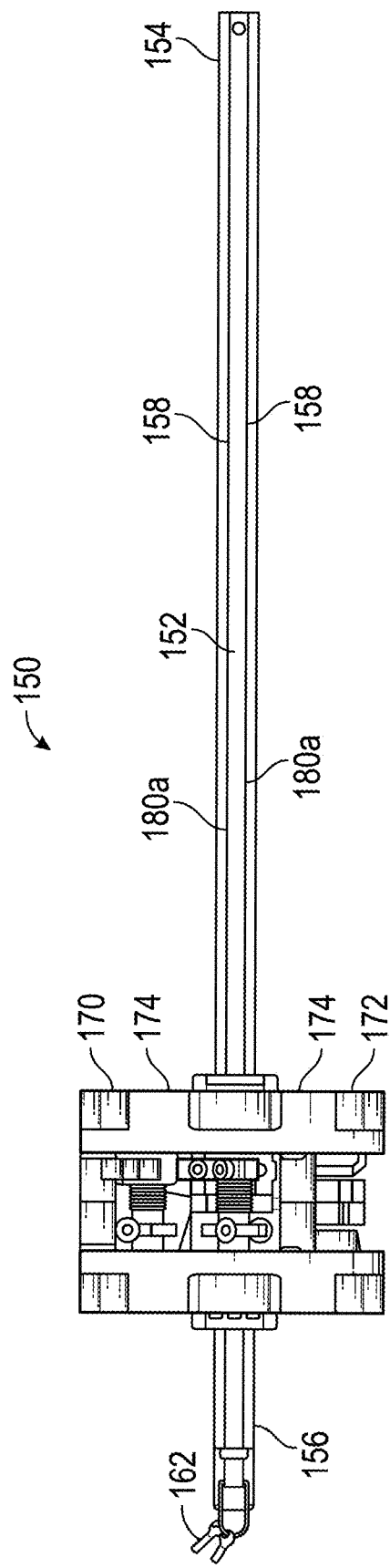
FIG. 18 illustrates an instrument having an instrument-based insertion architecture.

FIG. 18 illustrates an instrument having an instrument based insertion architecture in accordance with some embodiments. The instrument 150 can be coupled to any of the instrument drivers discussed above. The instrument 150 comprises an elongated shaft 152, an end effector 162 connected to the shaft 152, and a handle 170 coupled to the shaft 152. The elongated shaft 152 comprises a tubular member having a proximal portion 154 and a distal portion 156. The elongated shaft 152 comprises one or more channels or grooves 158 along its outer surface. The grooves 158 are configured to receive one or more wires or cables 180 therethrough. One or more cables 180 thus run along an outer surface of the elongated shaft 152. In other embodiments, cables 180 can also run through the elongated shaft 152. Manipulation of the one or more cables 180 (e.g., via an instrument driver) results in actuation of the end effector 162.

The instrument handle 170, which may also be referred to as an instrument base, may generally comprise an attachment interface 172 having one or more mechanical inputs 174, e.g., receptacles, pulleys or spools, that are designed to be reciprocally mated with one or more torque couplers on an attachment surface of an instrument driver. In some embodiments, the instrument 150 comprises a series of pulleys or cables that enable the elongated shaft 152 to translate relative to the handle 170. In other words, the instrument 150 itself comprises an instrument-based insertion architecture that accommodates insertion of the instrument, thereby minimizing the reliance on a robot arm to provide insertion of the instrument 150. In other embodiments, a robotic arm can be largely responsible for instrument insertion.

E. Controller

Any of the robotic systems described herein can include an input device or controller for manipulating an instrument attached to a robotic arm. In some embodiments, the controller can be coupled (e.g., communicatively, electronically, electrically, wirelessly and/or mechanically) with an instrument such that manipulation of the controller causes a corresponding manipulation of the instrument e.g., via master slave control.

Figure 19:
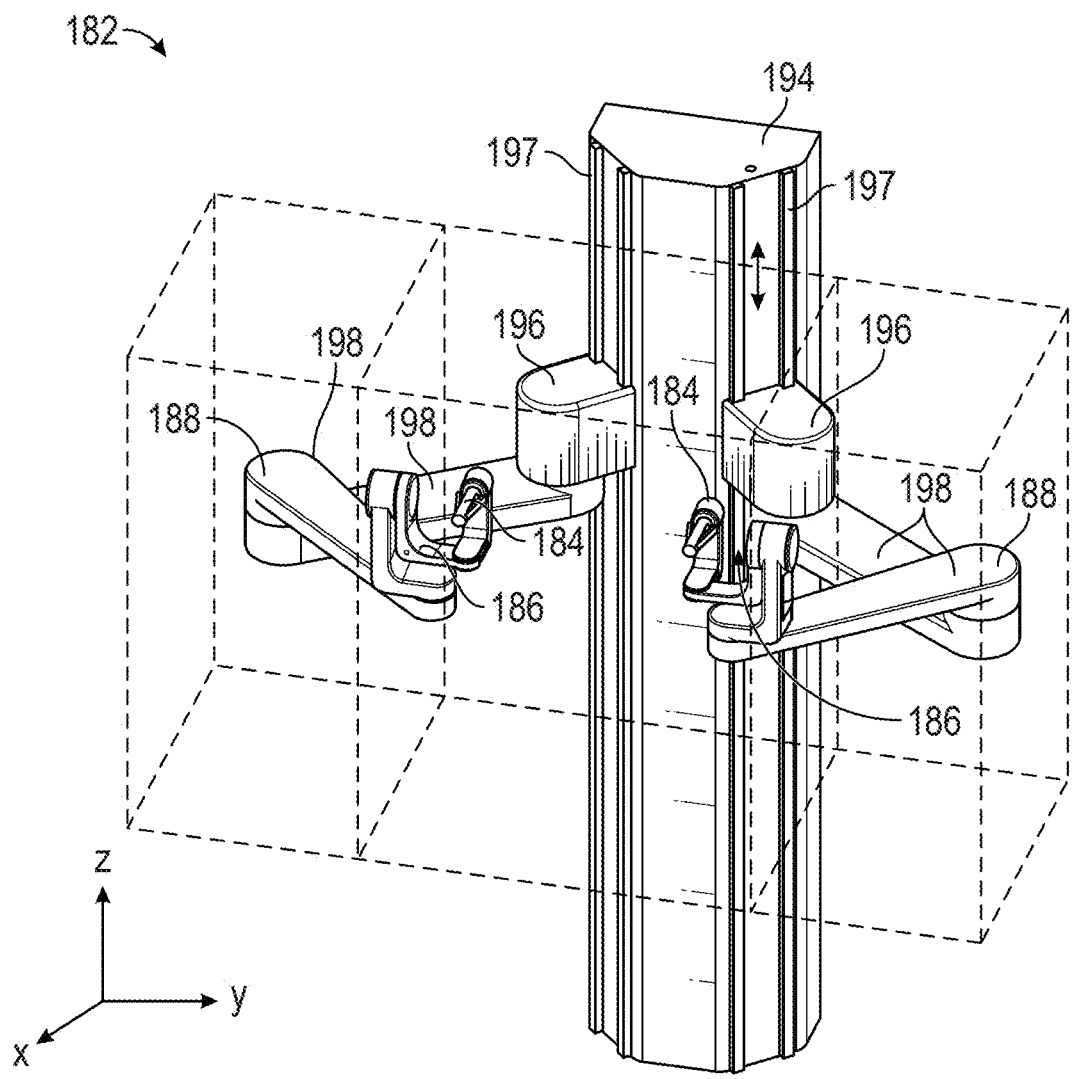
FIG. 19 illustrates an exemplary controller.

FIG. 19 is a perspective view of an embodiment of a controller 182. In the present embodiment, the controller 182 comprises a hybrid controller that can have both impedance and admittance control. In other embodiments, the controller 182 can utilize just impedance or passive control. In other embodiments, the controller 182 can utilize just admittance control. By being a hybrid controller, the controller 182 advantageously can have a lower perceived inertia while in use.

In the illustrated embodiment, the controller 182 is configured to allow manipulation of two medical instruments, and includes two handles 184. Each of the handles 184 is connected to a gimbal 186. Each gimbal 186 is connected to a positioning platform 188.

As shown in FIG. 19, each positioning platform 188 includes a SCARA arm (selective compliance assembly robot arm) 198 coupled to a column 194 by a prismatic joint 196. The prismatic joints 196 are configured to translate along the column 194 (e.g., along rails 197) to allow each of the handles 184 to be translated in the z-direction, providing a first degree of freedom. The SCARA arm 198 is configured to allow motion of the handle 184 in an x-y plane, providing two additional degrees of freedom.

In some embodiments, one or more load cells are positioned in the controller. For example, in some embodiments, a load cell (not shown) is positioned in the body of each of the gimbals 186. By providing a load cell, portions of the controller 182 are capable of operating under admittance control, thereby advantageously reducing the perceived inertia of the controller while in use. In some embodiments, the positioning platform 188 is configured for admittance control, while the gimbal 186 is configured for impedance control. In other embodiments, the gimbal 186 is configured for admittance control, while the positioning platform 188 is configured for impedance control. Accordingly, for some embodiments, the translational or positional degrees of freedom of the positioning platform 188 can rely on admittance control, while the rotational degrees of freedom of the gimbal 186 rely on impedance control.

F. Navigation and Control

Traditional endoscopy may involve the use of fluoroscopy (e.g., as may be delivered through a C-arm) and other forms of radiation-based imaging modalities to provide endoluminal guidance to an operator physician. In contrast, the robotic systems contemplated by this disclosure can provide for non-radiation-based navigational and localization means to reduce physician exposure to radiation and reduce the amount of equipment within the operating room. As used herein, the term "localization" may refer to determining and/or monitoring the position of objects in a reference coordinate system. Technologies such as pre-operative mapping, computer vision, real-time EM tracking, and robot command data may be used individually or in combination to achieve a radiation-free operating environment. In other cases, where radiation-based imaging modalities are still used, the pre-operative mapping, computer vision, real-time EM tracking, and robot command data may be used individually or in combination to improve upon the information obtained solely through radiation-based imaging modalities.

Figure 20:
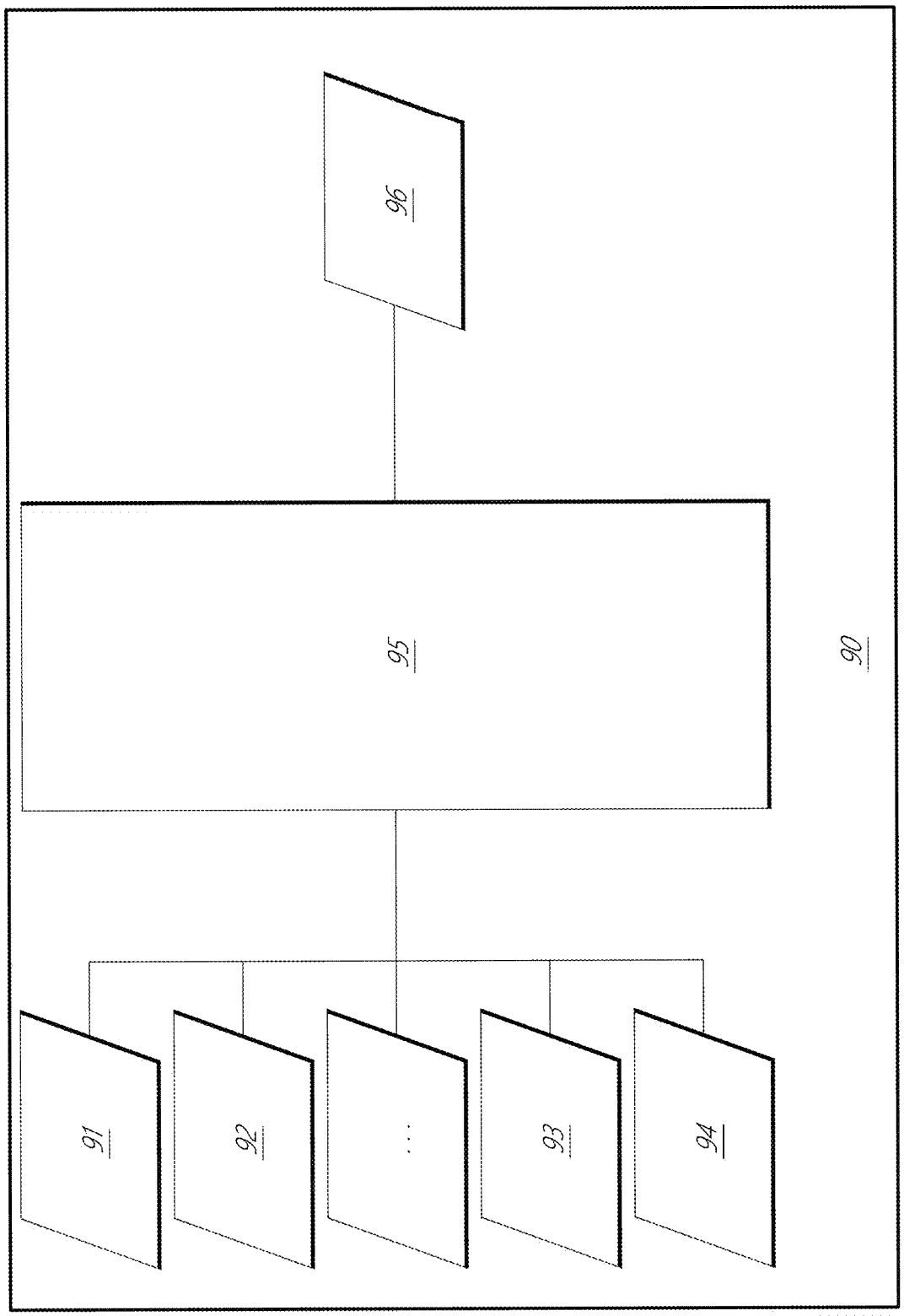
FIG. 20 depicts a block diagram illustrating a localization system that estimates a location of one or more elements of the robotic systems of FIGS. 1-10, such as the location of the instrument of FIGS. 16-18, in accordance to an example embodiment.

FIG. 20 is a block diagram illustrating a localization system 90 that estimates a location of one or more elements of the robotic system, such as the location of the instrument, in accordance to an example embodiment. The localization system 90 may be a set of one or more computer devices configured to execute one or more instructions. The computer devices may be embodied by a processor (or processors) and computer-readable memory in one or more components discussed above. By way of example and not limitation, the computer devices may be in the tower 30 shown in FIG. 1, the cart shown in FIGS. 1-4, the beds shown in FIGS. 5-14, etc.

As shown in FIG. 20, the localization system 90 may include a localization module 95 that processes input data 91-94 to generate location data 96 for the distal tip of a medical instrument. The location data 96 may be data or logic that represents a location and/or orientation of the distal end of the instrument relative to a frame of reference. The frame of reference can be a frame of reference relative to the anatomy of the patient or to a known object, such as an EM field generator (see discussion below for the EM field generator).

The various input data 91-94 are now described in greater detail. Pre-operative mapping may be accomplished through the use of the collection of low dose CT scans. Pre-operative CT scans are reconstructed into three-dimensional images, which are visualized, e.g. as "slices" of a cutaway view of the patient's internal anatomy. When analyzed in the aggregate, image-based models for anatomical cavities, spaces and structures of the patient's anatomy, such as a patient lung network, may be generated. Techniques such as center-line geometry may be determined and approximated from the CT images to develop a three-dimensional volume of the patient's anatomy, referred to as model data 91 (also referred to as "preoperative model data" when generated using only preoperative CT scans). The use of center-line geometry is discussed in U.S. patent application Ser. No. 14/523,760, the contents of which are herein incorporated in its entirety. Network topological models may also be derived from the CT-images, and are particularly appropriate for bronchoscopy.

In some embodiments, the instrument may be equipped with a camera to provide vision data 92. The localization module 95 may process the vision data to enable one or more vision-based location tracking. For example, the preoperative model data may be used in conjunction with the vision data 92 to enable computer vision-based tracking of the medical instrument (e.g., an endoscope or an instrument advance through a working channel of the endoscope). For example, using the preoperative model data 91, the robotic system may generate a library of expected endoscopic images from the model based on the expected path of travel of the endoscope, each image linked to a location within the model. Intra-operatively, this library may be referenced by the robotic system in order to compare real-time images captured at the camera (e.g., a camera at a distal end of the endoscope) to those in the image library to assist localization.

Other computer vision-based tracking techniques use feature tracking to determine motion of the camera, and thus the endoscope. Some features of the localization module 95 may identify circular geometries in the preoperative model data 91 that correspond to anatomical lumens and track the change of those geometries to determine which anatomical lumen was selected, as well as the relative rotational and/or translational motion of the camera. Use of a topological map may further enhance vision-based algorithms or techniques.

Optical flow, another computer vision-based technique, may analyze the displacement and translation of image pixels in a video sequence in the vision data 92 to infer camera movement. Examples of optical flow techniques may include motion detection, object segmentation calculations, luminance, motion compensated encoding, stereo disparity measurement, etc. Through the comparison of multiple frames over multiple iterations, movement and location of the camera (and thus the endoscope) may be determined.

The localization module 95 may use real-time EM tracking to generate a real-time location of the endoscope in a global coordinate system that may be registered to the patient's anatomy, represented by the preoperative model. In EM tracking, an EM sensor (or tracker) comprising of one or more sensor coils embedded in one or more locations and orientations in a medical instrument (e.g., an endoscopic tool) measures the variation in the EM field created by one or more static EM field generators positioned at a known location. The location information detected by the EM sensors is stored as EM data 93. The EM field generator (or transmitter), may be placed close to the patient to create a low intensity magnetic field that the embedded sensor may detect. The magnetic field induces small currents in the sensor coils of the EM sensor, which may be analyzed to determine the distance and angle between the EM sensor and the EM field generator. These distances and orientations may be intra-operatively "registered" to the patient anatomy (e.g., the preoperative model) in order to determine the geometric transformation that aligns a single location in the coordinate system with a position in the pre-operative model of the patient's anatomy. Once registered, an embedded EM tracker in one or more positions of the medical instrument (e.g., the distal tip of an endoscope) may provide real-time indications of the progression of the medical instrument through the patient's anatomy.

Robotic command and kinematics data 94 may also be used by the localization module 95 to provide localization data 96 for the robotic system. Device pitch and yaw resulting from articulation commands may be determined during pre-operative calibration. Intra-operatively, these calibration measurements may be used in combination with known insertion depth information to estimate the position of the instrument. Alternatively, these calculations may be analyzed in combination with EM, vision, and/or topological modeling to estimate the position of the medical instrument within the network.

As FIG. 20 shows, a number of other input data can be used by the localization module 95. For example, although not shown in FIG. 20, an instrument utilizing shape-sensing fiber can provide shape data that the localization module 95 can use to determine the location and shape of the instrument.

The localization module 95 may use the input data 91-94 in combination(s). In some cases, such a combination may use a probabilistic approach where the localization module 95 assigns a confidence weight to the location determined from each of the input data 91-94. Thus, where the EM data may not be reliable (as may be the case where there is EM interference) the confidence of the location determined by the EM data 93 can be decrease and the localization module 95 may rely more heavily on the vision data 92 and/or the robotic command and kinematics data 94.

As discussed above, the robotic systems discussed herein may be designed to incorporate a combination of one or more of the technologies above. The robotic system's computer-based control system, based in the tower, bed and/or cart, may store computer program instructions, for example, within a non-transitory computer-readable storage medium such as a persistent magnetic storage drive, solid state drive, or the like, that, upon execution, cause the system to receive and analyze sensor data and user commands, generate control signals throughout the system, and display the navigational and localization data, such as the position of the instrument within the global coordinate system, anatomical map, etc.

2. Driving Medical Instruments

Embodiments of the disclosure relate to devices, systems, and techniques for manually and robotically driving medical instruments of robotic medical systems. As will be discussed below, in some instances, certain aspects of medical procedures may beneficially be performed manually, while other aspects of the procedures may beneficially be performed robotically. The devices, systems, and techniques described herein allow for both manual and robotic control in a manner that facilitates these procedures and provides several notable advantages as discussed below.

Figure 21A:
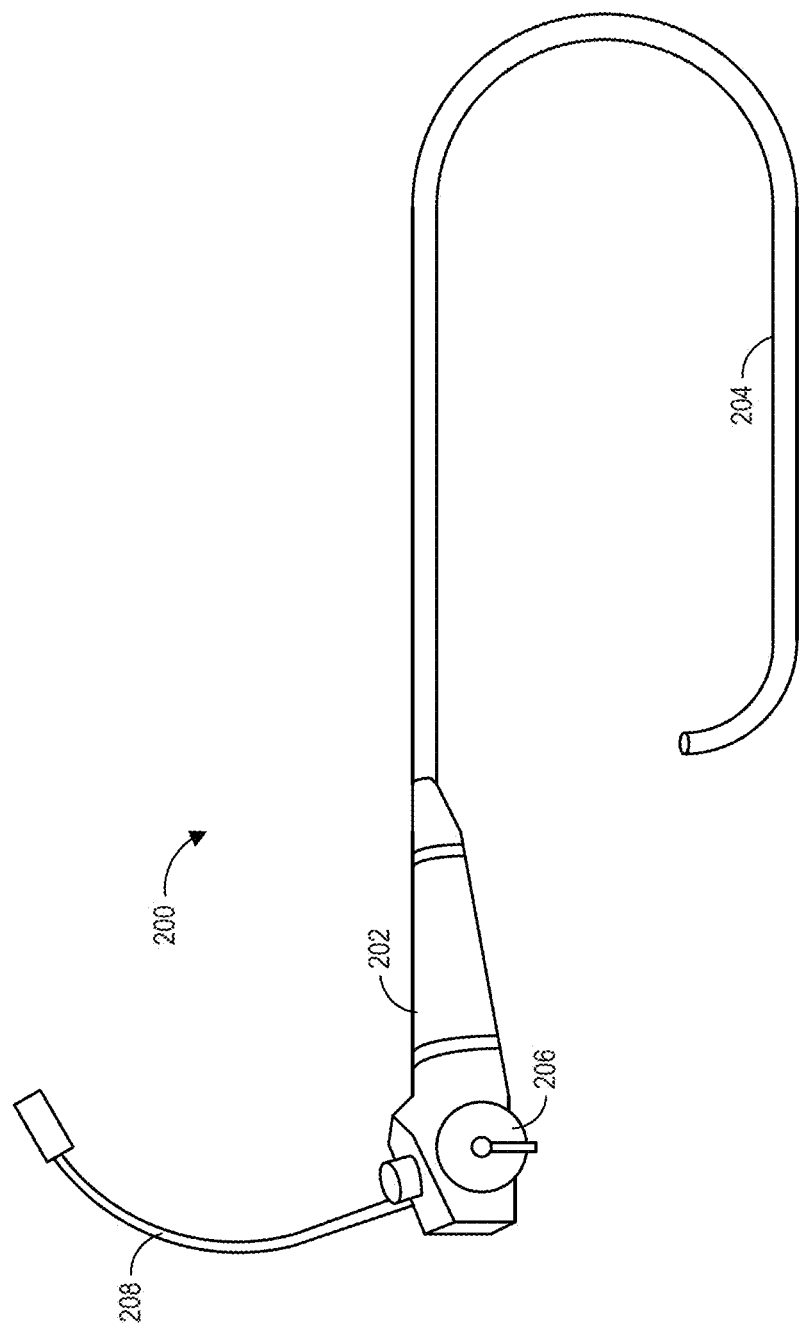
FIG. 21A illustrates an embodiment of a manually controllable endoscope.

FIG. 21A illustrates an embodiment of a manually controllable medical instrument 200. In the illustrated embodiment, the medical instrument 200 is a manually controllable endoscope. As shown, the medical instrument 200 includes a handle 202, an elongated shaft 204, an articulation input 206, and vision and light connections 208. The elongated shaft 204 extends from the handle 202 and may be configured for insertion into a patient. For example, the elongated shaft 204 may be configured to be flexible and articulable so that it is navigable through a patient's anatomy.

In some embodiments, articulation (e.g., bending or deflection) of the elongated shaft 204 is accomplished with one or more pull wires that extend between the articulation input 206, which can be positioned on the handle 202, and the distal end of the elongated shaft 204. In the illustrated embodiment, the articulation input 206 is a thumbwheel. A physician or other medical personnel can operate (e.g., rotate) the thumbwheel while holding the handle 202 to adjust a tension of the pull wire to cause articulation of the elongated shaft 204. In some embodiments, the medical instrument 200 is configured for two-way deflection of the elongated shaft 204 (e.g., deflection within a single plane). For example, rotating the articulation input 206 in a first direction can articulate the elongated shaft 204 up, and rotating the articulation input 206 in a second direction (e.g., the opposite direction) can articulate the elongated shaft 204 down. In other embodiments, the medical instrument 200 can be configured for other degrees of deflection, such as four-way deflection.

In some embodiments, roll control for the medical instrument 200 (i.e., rolling the elongated shaft 204 about its longitudinal axis) can be accomplished by physically rolling the handle 202. For example, the elongated shaft 204 can be fixed to the handle 202 such that rolling the handle 202 causes a corresponding roll of the elongated shaft 204. Insertion of the elongated shaft 204 into a patient is generally accomplished by gripping the elongated shaft 204 and manually advancing the elongated shaft 204 into or retracting the elongated shaft 204 from the patient.

Figure 21B:
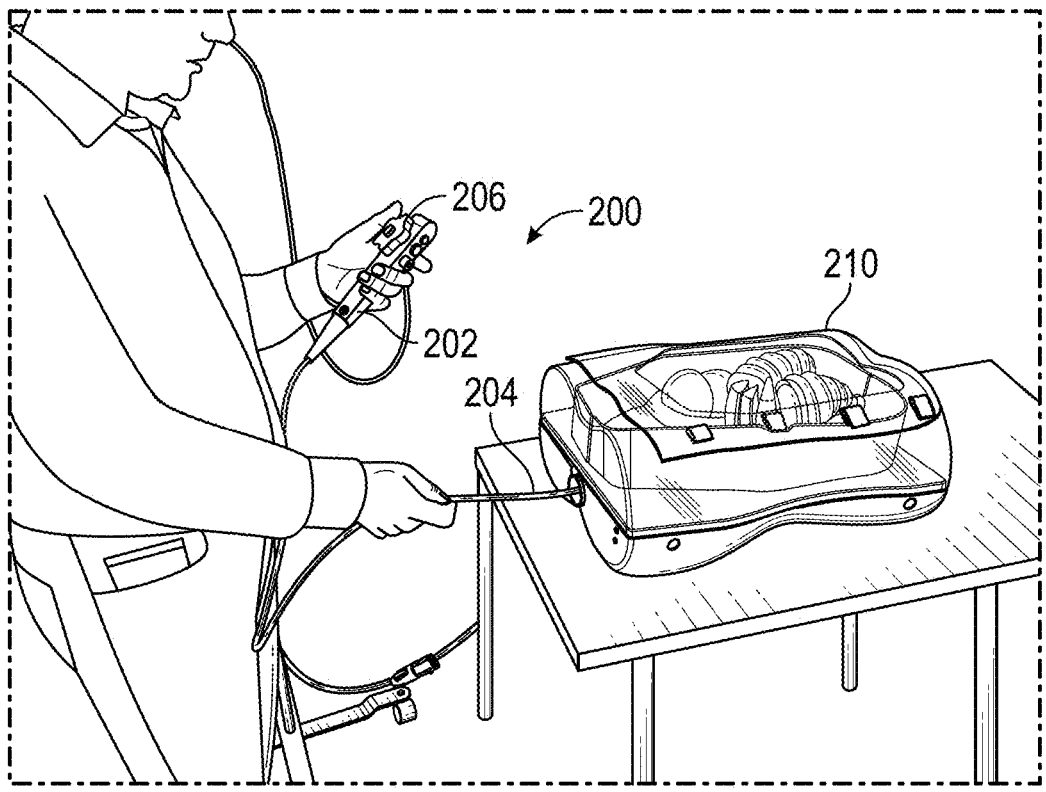
FIGS. 21B and 21C depict the manually controllable endoscope of FIG. 21A during use.
Figure 21C:
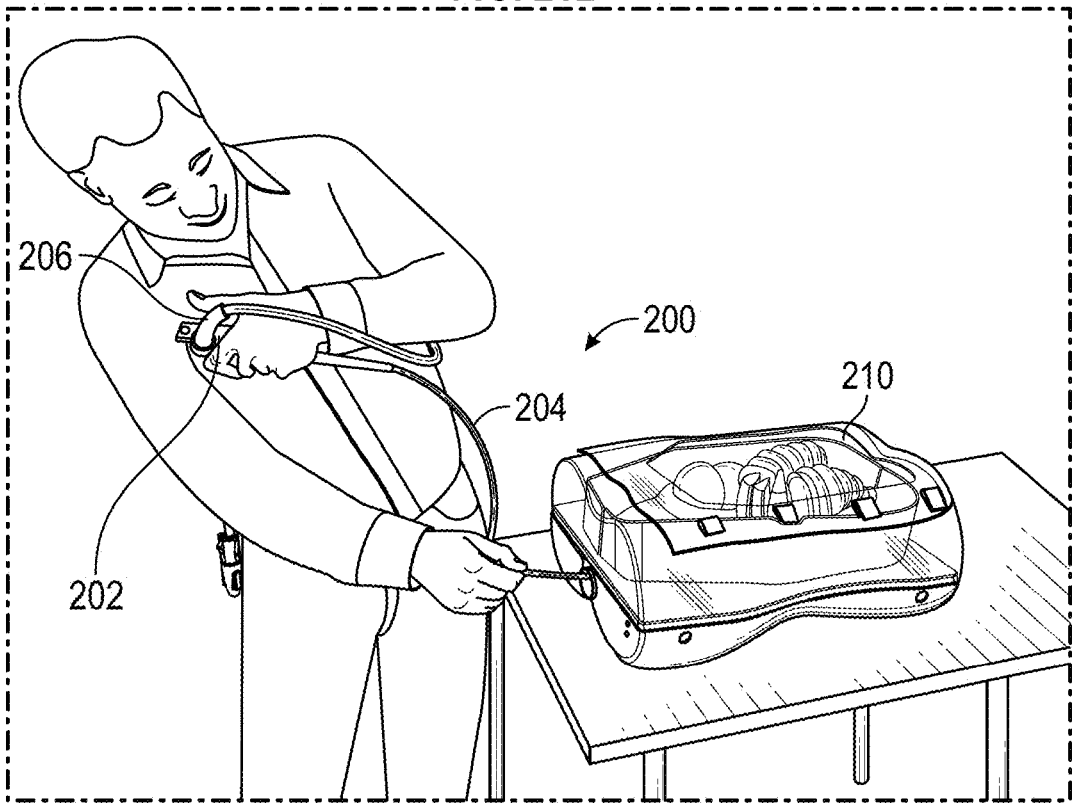

A physician can use the medical instrument 200 to perform medical procedures, such as endoscopic procedures. During the procedures, the physician can guide the elongated shaft 204 into the patient using the articulation input 206 to control articulation of the elongated shaft 204 and the physician can roll the handle 202 to roll the elongated shaft 204 to navigate through the patient's anatomy. FIGS. 21B and 21C depict examples of the manually controllable medical instrument 200 of FIG. 21A during use.

As shown in FIG. 21B, during use of the medical instrument 200, the physician may hold or grip the elongated shaft 204 with a first hand, e.g., the hand near the location at which the elongated shaft 204 enters the patient 210. In this position, the physician can manually advance or retract the elongated shaft 204 by advancing or retracting his or her hand. By repositioning his or her hand along the elongated shaft 204 the physician can feed the elongated shaft 204 into the patient. Further, by maintaining the hand close to the location at which the elongated shaft 204 enters the patient 210, the physician can manage and prevent buckling of the elongated shaft 204 in a relatively intuitive manner.

While inserting the elongated shaft 204, the physician may hold the handle 202 with a second hand as shown. In this position, the physician can operate the articulation input 206 (e.g., the thumbwheel) with the second hand to control articulation of the elongated shaft 204. Thus, use of the medical instrument 200 generally requires both of the physician's hands. The physician can control the roll of the elongated shaft 204 by rolling the handle 202. However, as illustrated in FIG. 21C, manually operating the medical instrument 200 can lead to difficult and/or unnatural positions for the physician, which can complicate the procedure. This can occur, for example, because the physician must physically roll the handle 202 to roll the elongated shaft 204 and because the articulation input 206 is located on the handle 202 which is positioned far from the location at which the elongated shaft 204 is inserted into the patient 210. Thus, a need exists for a medical instrument that can be manually inserted into the patient 210 in a more convenient, comfortable, and ergonomic manner, e.g., prior to performing a robot-assisted procedure with the medical instrument or component(s) thereof.

In some instances, performing medical procedures using the medical instrument 200 can involve, as a first step, navigating the elongated shaft 204 through the patient's anatomy to a treatment site, and then, as a second step, performing some operation at the treatment site. Notwithstanding the difficult or unnatural body positions sometimes required of physicians during use of the manually controllable medical instrument 200, today, physicians are able to perform the first step relatively quickly and easily. That is, in many cases, physicians have little trouble manually guiding the elongated shaft 204 through the patient's anatomy to the treatment site. This can be because, for example, super precise control during the initial rough insertion step may not be necessary, and manually inserting the elongated shaft 204 allows the physician to take advantage of tactile feedback felt during insertion. In some embodiments, physicians can even perform the rough insertion step more quickly than a robotic medical system can perform the insertion.

Further, in some medical procures, such as those that involve navigating the elongated shaft 204 through the patients gastrointestinal tract, the physician can implement surging, whipping, or other body English techniques, combined with immediate tip steering to create bunching, draping, etc., of the gastrointestinal tract, which can facilitate navigation through the anatomy. Such techniques are commonly performed by physicians when manually inserting the medical instrument 200, but may be very difficult or impossible to perform with today's robotic medical systems. Thus, in some embodiments, it may be advantageous to perform the initial rough positioning step manually, rather than robotically.

Once at the treatment site, however, medical procedures performed with the medical instrument 200 may require fine and precise control, which can be very difficult for physicians to perform manually. This is especially true considering the difficult and unnatural body positions manually operating the medical instrument 200 may require (e.g., as shown in FIG. 21C). The fine and precise control required at the treatment site may be better performed using a robotic medical system, such as those described above with reference to FIGS. 1-20 or those described below.

Thus, in some instances, it may be advantageous to perform the initial rough insertion step manually, and then, once at the treatment site, perform the medical procedure using a robotic medical system that provides a high degree of precision and control. FIGS. 22A-30, described below, relate to robotic systems, methods, and devices that can advantageously allow for both manual control and robotic control of medical instruments. These systems, methods, and devices can allow manual control to be used when most advantageous, for example, during the initial positioning step, and for robotic control to be used when most advantageous, for example, during the portions of the procedures that require very fine and precise control.

Figure 22A:
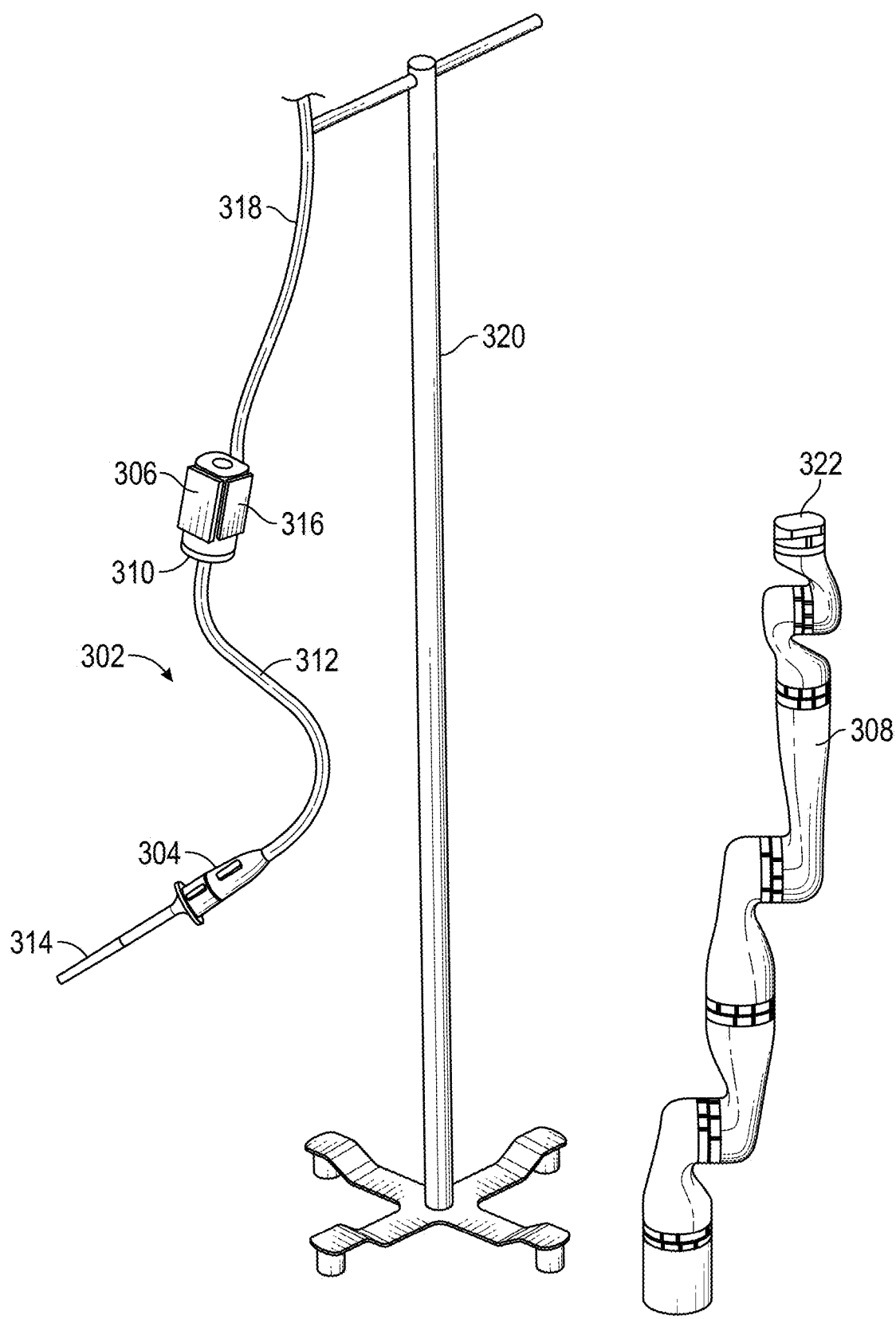
FIG. 22A illustrates an embodiment of a robotic medical system in a manual insertion configuration.
Figure 22B:
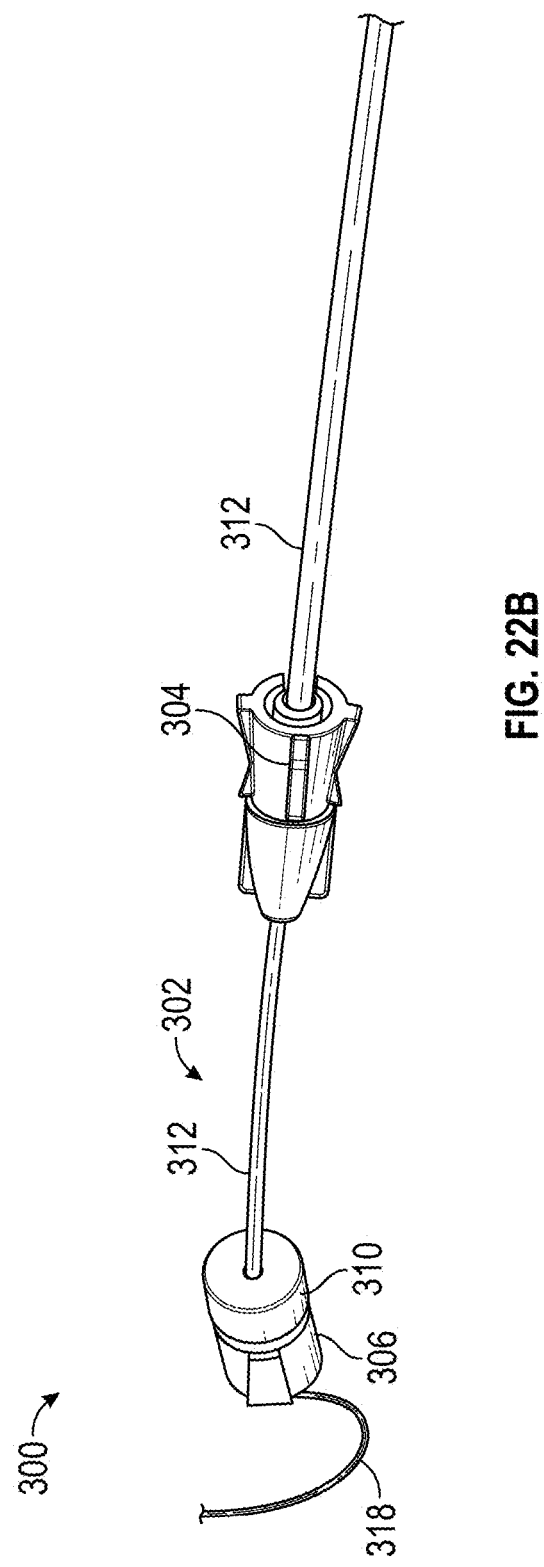
FIG. 22B illustrates another view of the robotic medical system of FIG. 22A in the manual insertion configuration.
Figure 22C:
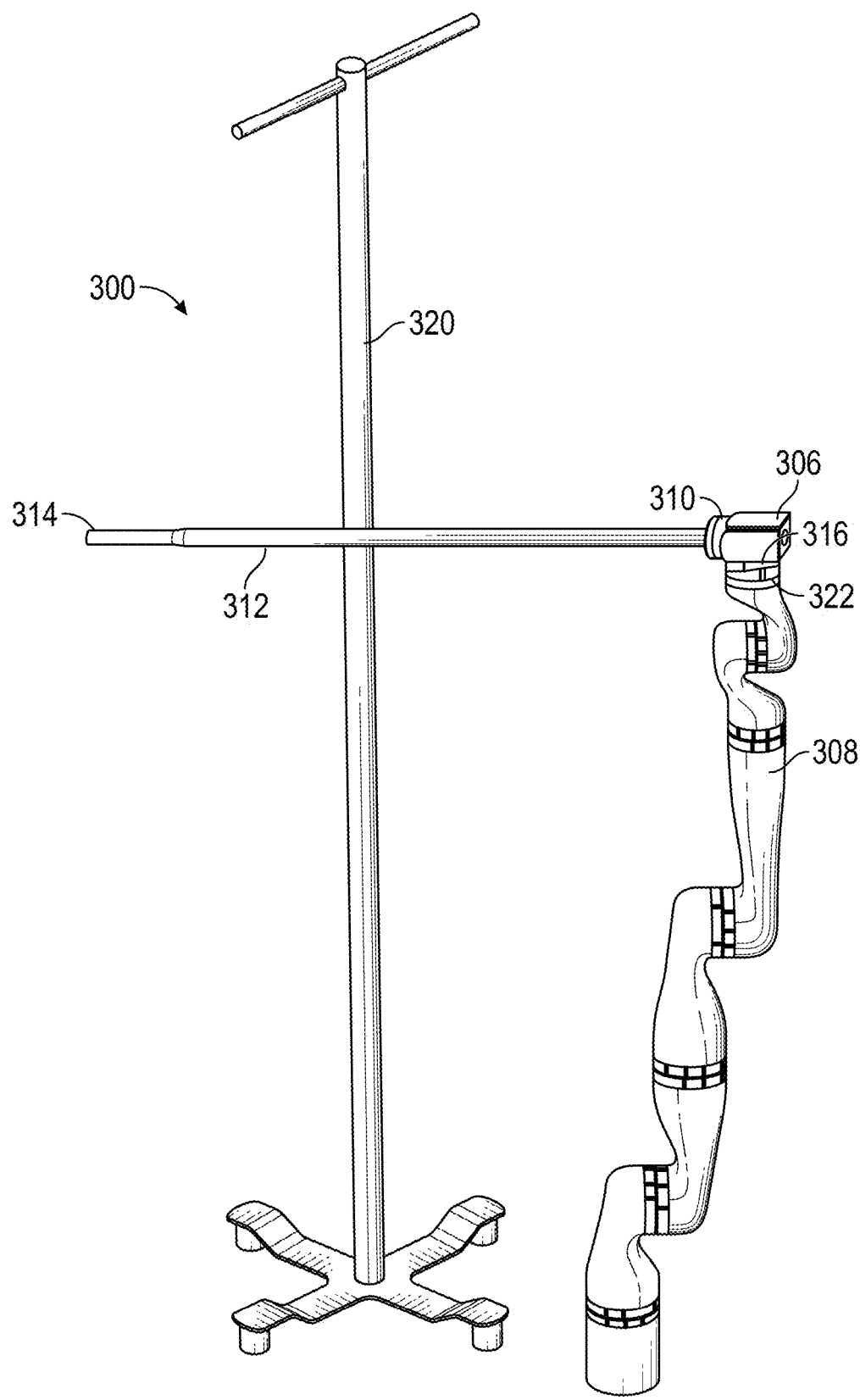
FIG. 22C illustrates the embodiment of the robotic medical system of FIG. 22B in a robotic control configuration.

FIGS. 22A-22C illustrate components of a robotic medical system 300 that can be configured for both manual control and robotic control. FIGS. 22A and 22B illustrate the robotic medical system 300 in a manual control configuration, and FIG. 22C illustrates the robotic medical system 300 in a robotic control configuration.

As shown in FIG. 22A, the robotic medical system 300 can include a medical instrument 302, a drive device 304, an instrument drive mechanism 306, and an instrument positioning device 308, among other things. In FIG. 22A, the instrument positioning device 308 is illustrated as a robotic arm, although other types of instrument positioning devices may also be used. The medical instrument 302 may be similar, for example, to the medical instruments discussed above with reference to FIGS. 1, 3-5, 8, and 16-18, among others. For example, in some embodiments, the medical instrument 302 is similar to the medical instrument 70 shown in FIG. 16.

As shown in FIG. 22A, the medical instrument 302 can include an instrument handle or base 310 and an elongated shaft 312. The elongated shaft 312 can extend from the base 310 to a distal end 314. During use, the distal end 314 of the elongated shaft 312 can be inserted into the patient. In some embodiments, the elongated shaft 312 can be inserted into the patient through a natural orifice or other surgical port (such as a surgical incision). The elongated shaft 312 can be flexible and articulable such that it can be navigated through the patient's anatomy. For example, the elongated shaft 312 can include one or more tendons or pull wires that can be actuated to articulate the elongated shaft 312 as described above with reference to FIG. 16. The pull wires can be associated with drive inputs (see, for example, the drive inputs 73 of FIG. 16) that can be positioned on the instrument base 310. The drive inputs can be driven, for example, rotated, to actuate the pull wires to articulate the elongated shaft 312.

The base 310 can be configured to engage, attach, or couple to the instrument drive mechanism 306. When coupled to the instrument drive mechanism 306, drive outputs on the instrument drive mechanism 306 can engage with the drive inputs of the base 310. The drive outputs may be similar, for example, to the drive outputs 74 described above with reference to FIG. 16. The drive outputs of the instrument drive mechanism 306 can thus drive the drive inputs on the base 310 of the medical instrument 302 in order to articulate the elongated shaft 312.

In the medical system embodiments described above with reference to FIGS. 1-20, the instrument drive mechanisms are positioned on the distal ends of instrument positioning devices, such as robotic arms (see, for example, FIGS. 14, 16, and 17). As shown in FIG. 22A, however, which illustrates the system 300 in a configuration for manual control, in the system 300, the instrument drive mechanism 306 can be detached from the instrument positioning device 308 in some configurations. To this end, in some embodiments, the instrument drive mechanism can include an attachment mechanism, such as a connector 316, that is configured to selectively engage a corresponding attachment mechanism, such as a connector 322, on the instrument positioning device 308. The connectors 316, 322 can comprise any structure that selectively and securely allows for the instrument drive mechanism 306 to be coupled to the instrument positioning device 308.

In some embodiments, because the instrument drive mechanism 306 can be selectively coupled to the instrument positioning device 308, the instrument drive mechanism 306 can be considered a dockable instrument drive mechanism. For example, FIG. 22A illustrates an example configuration for the system 300, wherein the instrument drive mechanism 306 is undocked from the instrument positioning device 308. That is, in FIG. 22A, the connector 316 of the instrument drive mechanism 306 is not connected to the connector 322 of the instrument positioning device 308. In contrast, FIG. 22C (described further below) illustrates an example configuration for the system 300, wherein the instrument drive mechanism 306 is docked to the instrument positioning device 308. That is, in FIG. 22C, the connector 316 of the instrument drive mechanism 306 is connected to the connector 322 of the instrument positioning device 308 such that the instrument drive mechanism 306 is positioned on the instrument positioning device 308.

As mentioned above, FIG. 22A illustrates the system 300 in a configuration for manual control. In some embodiments, in this configuration, the instrument drive mechanism 306 is undocked from the instrument positioning device 308 as shown. In the illustrated embodiment, the instrument drive mechanism 306 is suspended from a stand 320 or other support structure. In some embodiments, no stand 320 or support structure is used. In the illustrated example, the instrument drive mechanism 306 is suspended from the stand 320 by power and vision cables 318. In some embodiments, the power and vision cables 318 supply power to the instrument drive mechanism 306 and allow the instrument drive mechanism 306 to connect to a vision or camera system in the medical instrument 302. Undocking the instrument drive mechanism 306 from the instrument positioning device 308 allows the medical instrument 302 to be moved freely. This can allow a physician to manually manipulate the medical instrument 302 as discussed in more detail below, for example, with reference to FIGS. 23A-24.

Figure 27A:
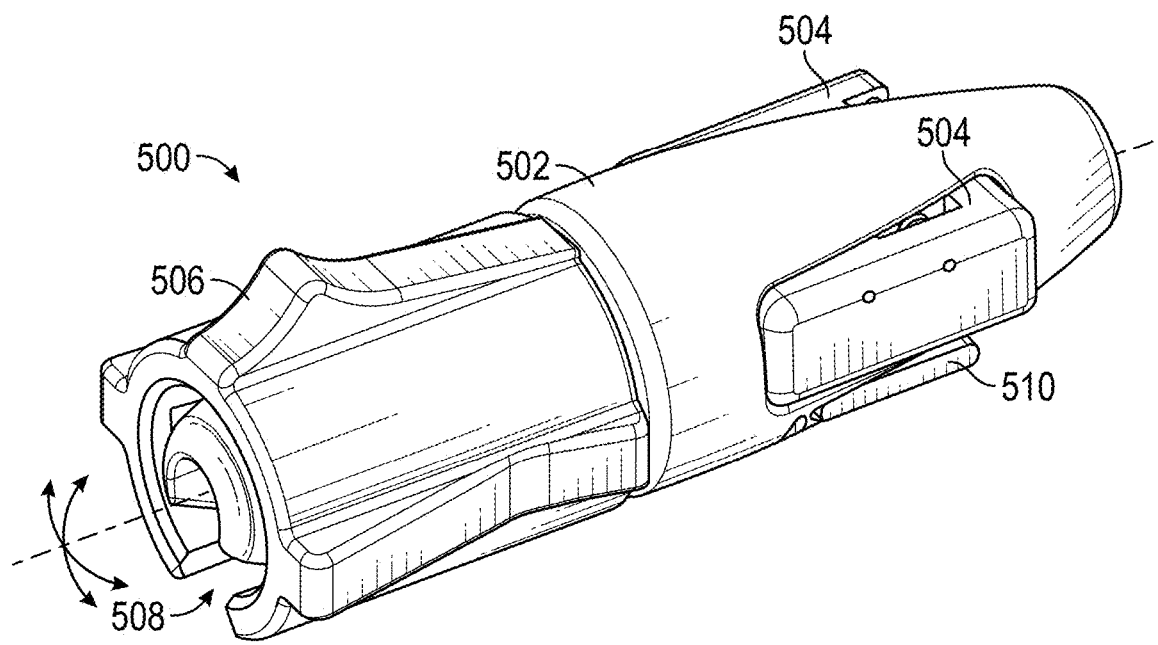
FIGS. 27A and 27B are top and bottom isometric views, respectively, of an embodiment of a drive device for use with robotic medical systems as described herein.

FIG. 22A illustrates that the system 300 can also include the drive device 304. In the illustrated embodiment, the drive device 304 comprises a handle that can be selectively attached to the elongated shaft 312. In some embodiments, the physician holds the drive device 304 while manually controlling the medical instrument 302 (as described below with reference to FIGS. 23A and 23B). As will be discussed in more detail below, the drive device 304 can include a gripping mechanism and an articulation input. The gripping mechanism can be configured to selectively engage with the elongated shaft 312. In some embodiments, the gripping mechanism can allow the drive device 304 to be positioned on the elongated shaft 312 of the medical instrument 302 at any location between the base 310 and the distal end 314. The physician can release the gripping mechanism to allow the drive device 304 to slide along the elongated shaft 312 and then reengage the gripping mechanism to reposition the drive device along the elongated shaft 312 as desired. An example gripping mechanism is shown in FIGS. 27D and 27E below.

As mentioned previously, the drive device 304 can also include an articulation input. The articulation input may be configured to allow the physician to provide user inputs of commanded articulation for the medical instrument 302. For example, the articulation input may allow the physician to provide a user input of commanded articulation that the elongated shaft 312 should be articulated in up, down, left, and/or right directions, for example. As will be described in more detail below, the articulation input can take many forms, including a joystick or buttons, that allow the physician to provide the user input.

The drive device 304 can include communications circuitry or module(s) that transmits the user input received from the physician using the articulation input to the instrument drive mechanism 306 such that the instrument drive mechanism 306 can drive the articulation using the drive outputs. The communications circuitry can be, for example, wireless or wired, and can also be direct between the drive device 304 and the instrument drive mechanism 306 or indirect, passing through one or more additional components, such as the towers or carts shown in FIGS. 1-4 above.

Thus, with the system 300 in the configuration for manual control, for example as illustrated in FIG. 22A, the physician may manually control the medical instrument 302. Manual control is enabled because, for example, the base 310 of the medical instrument 302 is attached to the instrument drive mechanism 306, allowing the instrument drive mechanism 306 to drive articulation of the shaft based on the user input of commanded articulation received from the physician using the articulation input on the drive device 304, and the instrument drive mechanism 306 is undocked from the instrument positioning device 308 allowing the medical instrument to be moved freely by the physician. Further, because the instrument drive mechanism 306 may include power and vision connections 318, the medical instrument 302 can be used even though it is not attached to the instrument positioning device 308. Also, the drive device 304 positioned on the elongated shaft 312 allows the user to grip the medical instrument 302 to insert the elongated shaft 306 into the patient. Example use of the medical system 300 in the manual control configuration is shown, for example, in FIGS. 23A-24, described below.

The system 300 can be used in the manual configuration to allow the physician to manually perform the initial positioning of the medical instrument 302. As discussed above, many physicians can initially guide the medical instrument 302 to the treatment site relatively quickly and easily manually, possibly faster than could be performed robotically. In some embodiments, after this initial rough manual positioning step, the system 300 can be transitioned to the robotic configuration shown in FIG. 22C, to allow the remainder of the procedure to be performed robotically.

FIG. 22B also illustrates the system 300 in a manual control configuration. As shown, the base 310 of the medical instrument 302 is coupled to the instrument drive mechanism 306 and the drive device 304 is coupled to the elongated shaft 312 of the medical instrument 302. The instrument drive mechanism 306 is undocked from the instrument positioning device (which is not illustrated in FIG. 22B). Power and vision cables 318 allow the instrument drive device 304 and medical instrument 302 to be used even while undocked from the instrument positioning device 306.

FIG. 22C illustrates an embodiment of the medical system 300 in a configuration for robotic control. As shown, when configured for robotic control, the instrument drive mechanism 306 is docked to the instrument positioning device 308. That is, the connector 316 of the instrument drive mechanism 306 is attached to the connector 322 of the instrument positioning device 308 as shown. Also, as illustrated, the drive device 304 (not shown in FIG. 22C) may be removed or detached from the elongated shaft 312 of the medical instrument 302. In this configuration, the medical system 300 may be similar to the robotic medical systems described above with reference to FIGS. 1-20. For example, the instrument drive mechanism 306 can drive articulation of the elongated shaft 306, while the instrument positioning device 308 (illustrated as a robotic arm) moves to insert and retract the elongated shaft 312 of the medical instrument 302 relative to the patient. As noted above, certain aspects of medical procedures can be better performed robotically to take advantage of the fine level of control provided by a robotic system. The system 300 can be used in the robotic configuration during these portions of the procedure.

Figure 23A:
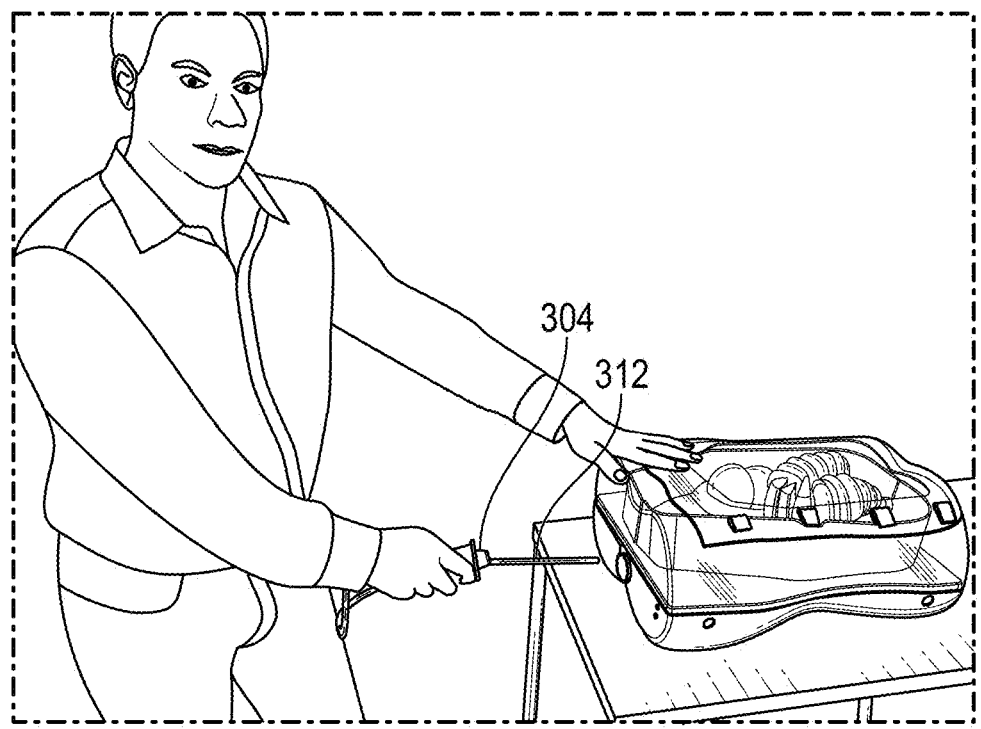
FIGS. 23A and 23B illustrate the robotic medical system of FIG. 22A in use while in the manual insertion configuration according to one embodiment.
Figure 23B:
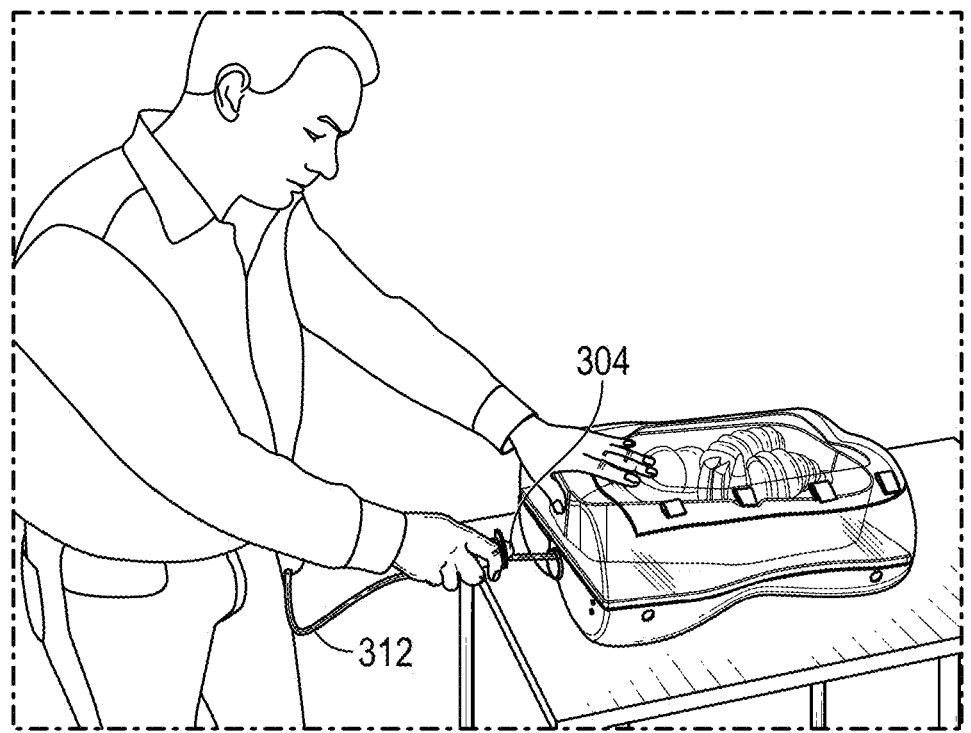

FIGS. 23A and 23B illustrate the robotic medical system 300 of FIG. 22A in use while in the manual control configuration according to one embodiment. As shown in FIG. 22A, the drive device 304 can be positioned on the elongated shaft 312 of the medical instrument. The physician may hold the drive device 304 in a first hand. The physician can then insert the elongated shaft 312 into the patient by advancing the hand that is holding the drive device 304 as shown in FIG. 23B. To further insert the elongated shaft 312 into the patient, the physician can release the gripping mechanism of the drive device 304 to allow him or her to slide the drive device 304 backwards along the elongated shaft 312. The physician can then reengage the gripping mechanism and use the drive device 304 to further insert the elongated shaft 312. Similar steps can be taken in reverse to retract the elongated shaft 312.

At the same time, the physician can control or command articulation of the elongated shaft 312 using the articulation input on the drive device 304. The commanded articulations can be transmitted from the drive device 304 to the instrument drive mechanism which drives the articulation. Although not visible in FIGS. 23A and 23B, the base of the medical instrument can be attached to the instrument drive mechanism, which can be undocked from the instrument positioning device as illustrated in FIGS. 22A and 22B.

As illustrated in FIGS. 23A and 23B, in some embodiments, the system 300 can allow for manual control of the medical instrument using only a single hand. For example, the physician, holding the drive device 304 in a single hand, can manually control insertion, retraction, and articulation of the medical instrument all using the hand which is holding the drive device 304. This can free up the physician's second hand for stabilizing the patient as shown.

Figure 24:
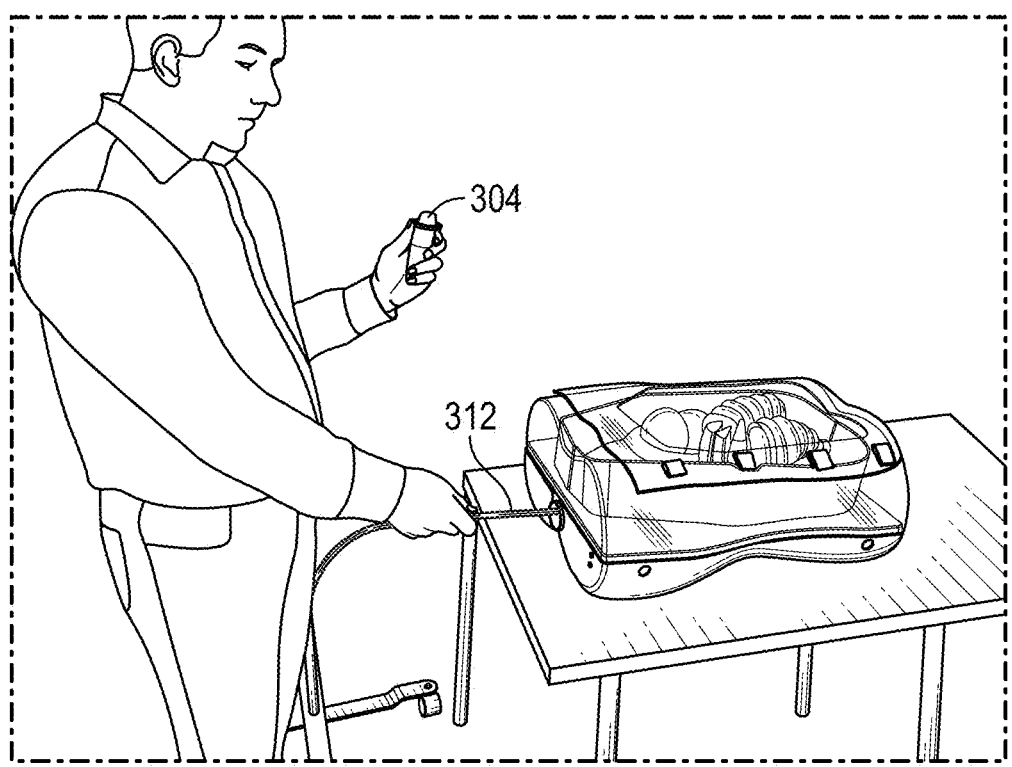
FIG. 24 illustrates the robotic medical system of FIG. 22A in use while in the manual insertion configuration according to another embodiment.

FIG. 24 illustrates the robotic medical system 300 of FIG. 22A in use while in the manual control configuration according to another embodiment. In this embodiment, the physician grips the elongated shaft 312 directly with a first hand to control insertion or retraction. The physician holds the drive device 304 in a second hand and uses the articulation input on the drive device 304 to control articulation. As before, the commanded articulations can be transmitted from the drive device 304 to the instrument drive mechanism which drives the articulation. Although not visible in FIG. 24, the base of the medical instrument can be attached to the instrument drive mechanism, which can be undocked from the instrument positioning device as illustrated in FIGS. 22A and 22B. This may allow two-handed manual control that is similar to that used for manually controllable medical instruments (compare, for example, FIG. 21B and FIG. 24).

A. Example Systems and Devices for Driving Medical Instruments

Figure 25:
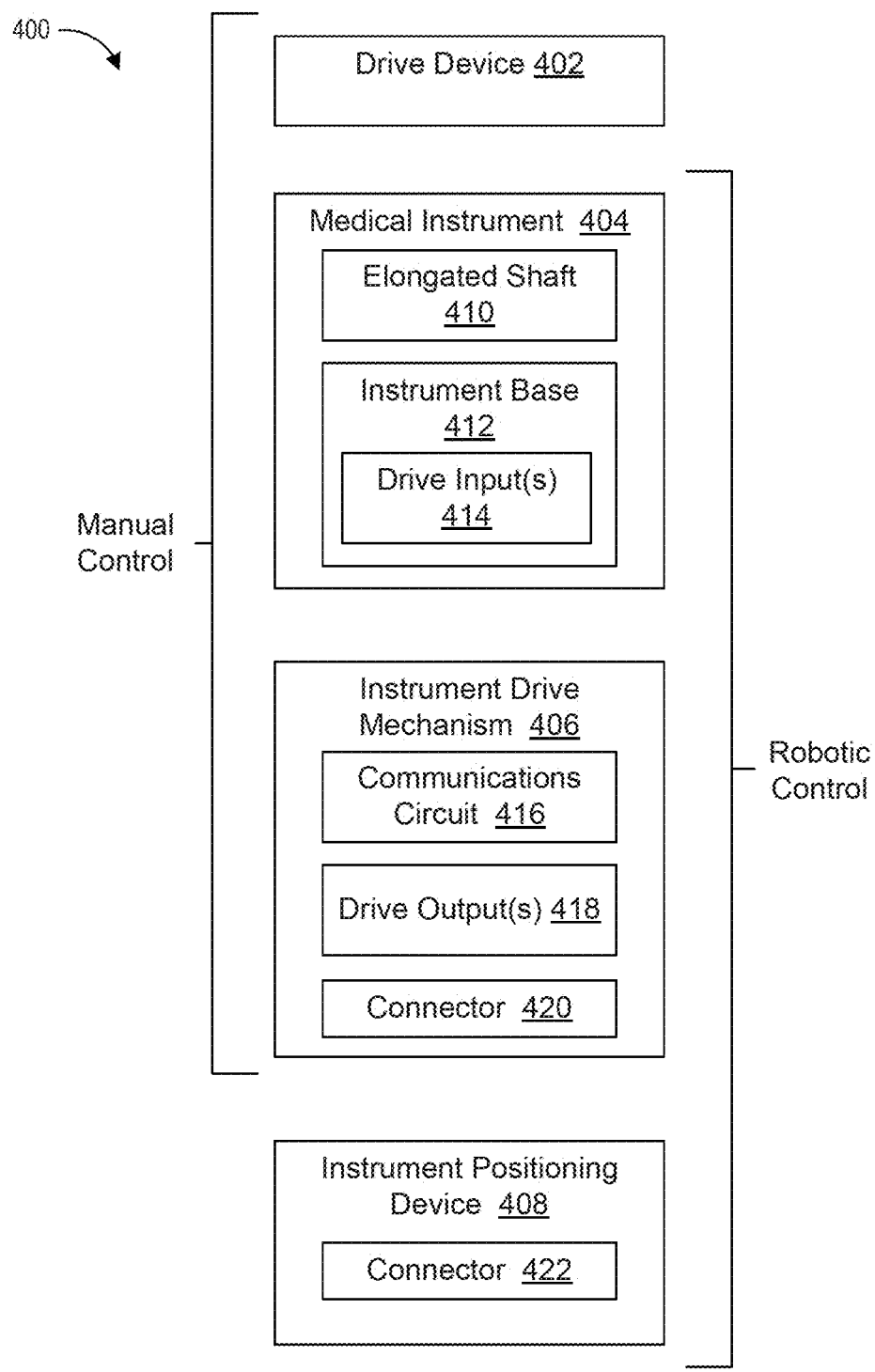
FIG. 25 is a block diagram illustrating an embodiment of a robotic medical system configured for manual and robotic control.

FIG. 25 is a block diagram showing components of an embodiment of a robotic medical system 400 configured for manual and robotic control. The robotic medical system 400 may be similar, for example, to the robotic medical system 300 shown in FIGS. 22A-23B. The system 400 can advantageously allow for either manual control or robotic control to be used as desired by the physician. This may allow the physician to use manual control for portions of the procedure that are better suited for manual control and to use robotic control for portions of the procedure that are better suited for robotic control. The system 400 may be transitioned quickly and simply between the manual control configuration and the robotic control configuration.

In the illustrated embodiment, the system 400 includes a drive device 402, a medical instrument 404, and instrument drive mechanism 406, and an instrument positioning device 406. As illustrated, in some embodiments, the drive device 402, the medical instrument 404, and the instrument drive mechanism 406 may be used for manual control, while the medical instrument 404, the instrument drive mechanism 406, and the instrument positioning device 408 may be used for robotic control. That is, in some embodiments, the drive device 402 may not be used for robotic control, and the instrument positioning device 408 may not be used for manual control.

Figure 26A:
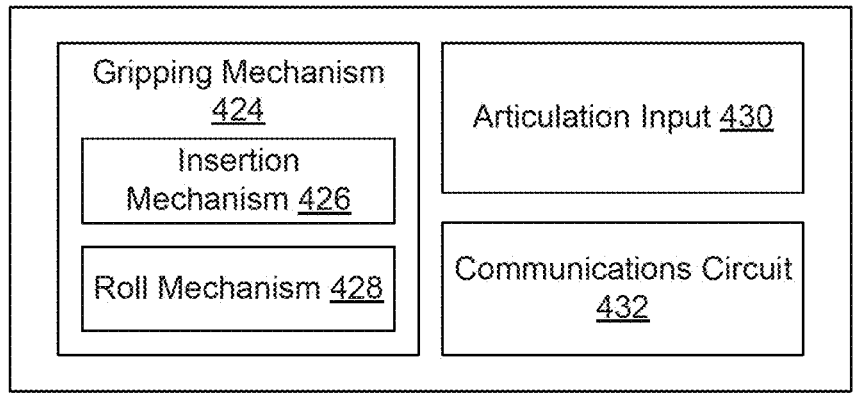
FIGS. 26A, 26B, and 26C illustrate block diagrams of three embodiments of drive devices that can be used with the robotic medical systems as described herein.
Figure 26B:
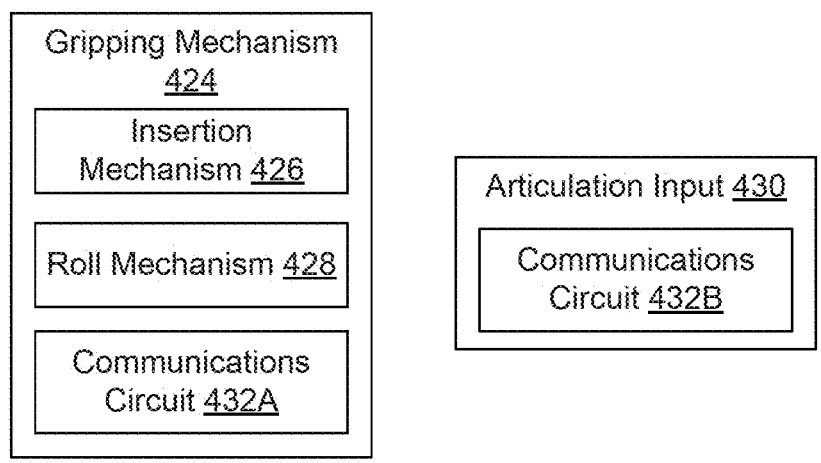
Figure 26C:
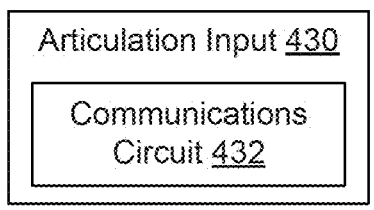

The system 400 can include the drive device 402. In some embodiments, the drive device 402 can be configured to allow for manual insertion or retraction of an elongated shaft 410 of the medical instrument 404 as described above (see FIGS. 23A and 23B). In some embodiments, the drive device 402 can be configured with an articulation input that allows a user to provide user input of commanded articulation for the elongated shaft 410 using the drive device 402. The drive device 402 may be similar to the drive device 304 described above with reference to FIGS. 22A-23B. FIGS. 26A-26C also show block diagrams of several embodiments of drive devices 402 that can be used with the system 400 in greater detail. Additionally, FIGS. 27A-28 illustrate a further embodiment of a drive device 500. FIGS. 26A-28 are described in more detail below.

The system 400 can include the medical instrument 404. As discussed above, the medical instrument 404 can include an elongated shaft 410 and an instrument base 412. The elongated shaft 410 can extend from the instrument base 412. The instrument base 412 can be configured to couple or attach to the instrument drive mechanism 406. When coupled to the instrument drive mechanism 406, one or more drive inputs 414 on the instrument base 412 engage one or more drive outputs 418 on the instrument drive mechanism 406 as described above. The drive outputs 418 can drive the drive inputs 414 to control articulation of the elongated shaft 410. In some embodiments, the medical instrument 404 comprises an endoscope.

The system 400 can include the instrument drive mechanism 406. As illustrated in FIG. 25, the instrument drive mechanism 406 can include a communications circuit 416, the drive outputs 418, and a connector 420. The instrument drive mechanism 406 can be dockable as described above. That is, in some embodiments the instrument drive mechanism 406 can be selectively docked, coupled, or attached to the instrument positioning device 408. To dock the instrument drive mechanism 406 to the instrument positioning device 408, the connector 420 of the instrument drive mechanism 406 can be engaged with a connector 422 of the instrument positioning device 408.

In some embodiments, the instrument drive mechanism 406 can be used undocked from the instrument positioning device 408 when the system 400 is configured for manual control (see FIGS. 22A and 22B). In some embodiments, the instrument drive mechanism 406 can be used docked to instrument positioning device 408 when the system 400 is configured for robotic control (see FIG. 22C).

The communications circuit 416 of the instrument drive mechanism 406 can be configured to receive signals indicative of user inputs of commanded articulation provided by the articulation input on the drive device 402. In some embodiments, the communications circuit 416 can be configured for wireless communication. For example, the communications circuit 416 can comprise one or more wireless wide area network (WWAN) radio circuits/chips (e.g., configured for communication via one or more cellular networks, such as 3G, 4G, 5G, etc.), one or more wireless local area network (WLAN) radio circuits/chips (e.g., configured for one or more standards, such as IEEE 802.11 (Wi-Fi)), and/or one or more personal area network (PAN) radio circuits/chips (e.g., configured for one or more standards, such as Bluetooth), or any other type of wireless circuit. In other embodiments, the communications circuit 416 can be configured for wired communication. As mentioned previously, communication between the instrument drive mechanism 406 and the drive device 402 through the communications circuit 416 can be direct or indirect. Indirect communication may pass through one or more additional components of the medical system and/or one or more computer or communications networks.

In some embodiments, the communications circuit 416 receives signals indicative of user inputs of commanded articulation provided by the articulation input on the drive device 402. These signals are then used by the instrument drive mechanism 406 to control the drive outputs 418. For example, in some embodiments, these signals are used by the instrument drive mechanism 406 to activate one or more motors associated with the drive outputs 418 (see FIG. 15) to cause the drive outputs 418 to rotate. As mentioned above, the drive outputs 418 can be engaged with drive inputs 414 of the medical instrument 404. Thus, the user inputs of commanded articulation provided by the articulation input on the drive device 402 can be transmitted to the instrument drive mechanism 406 through the communications circuit and used to drive the drive outputs 418 to cause articulation of the elongated shaft 410 of the medical instrument 404.

The connector 420 of the instrument drive mechanism 406 can be configured to selectively engage the connector 422 of the instrument positioning device 408 so that the instrument drive mechanism 406 can be docked and undocked from the instrument positioning device 408 as desired. The connectors 420, 422 can comprise any structure suitable for securing the instrument positioning device 406 to the instrument positioning device 408. For example, in some embodiments, the connectors 420, 422 comprise corresponding mechanical fasteners, such as screw type fasteners, rail and groove fasteners, or clamping fasteners, among others.

In some embodiments, the instrument drive mechanism 406 is configured so as to be sterilizable. For example, the instrument drive mechanism 406 can be configured to autoclavable. This can be advantageous because, since the instrument drive mechanism 406 is not permanently attached to the instrument positioning device 408, the instrument drive mechanism 406 can easily be removed and sterilized. This may allow the instrument drive mechanism 406 to be used during a procedures without being draped. For example, the instrument positioning device 408 can be draped, and then the undraped instrument drive mechanism 406 can be attached to the instrument positioning device 408. In some embodiments, this may simplify sterilization requirements and facilitate the procedures for which the system 400 can be used.

The system 400 can include the instrument positioning device 408. In some embodiments, the instrument positioning device 408 can comprise a robotic arm as shown above. In other embodiments, other types of instrument positioning devices 408, such as linear drives, may also be used. In general, the instrument positioning device 408 is used during robotic control of the system 400 as described above. For example, the instrument positioning device 408 can move the medical instrument 404, which is attached to the instrument positioning device 408 via the instrument drive mechanism 406, to perform the procedure. In some embodiments, the connector 422 is positioned on a distal end of the instrument positioning device 408. For example, the connector 422 can be on a distal end of a robotic arm.

FIGS. 26A, 26B, and 26C illustrate block diagrams of three embodiments of drive devices 402A, 402B, 402C, respectively, that can be used with the robotic medical system 400 of FIG. 25.

FIG. 26A, illustrates a block diagram of a first embodiment of the drive device 402A. As illustrated, the drive device 402A comprises a single unit, device, or handle, which includes a gripping mechanism 424, an articulation input 430, and communications circuitry 432. The gripping mechanism 424 can be configured to selectively engage with the elongated shaft 410 of the medical instrument 404. As described above with reference to FIG. 22A, the gripping mechanism 424 can, in some embodiments, be configured to position the drive device 402A at any or at various locations along the elongated shaft 410 between the instrument base 412 and a distal end of the elongated shaft 410. In some embodiments, when engaged with the elongated shaft 410, the gripping mechanism 424 fixedly attaches the drive device 402A to the elongated shaft 410. The gripping mechanism 424 can be released from the elongated shaft 410 to allow the drive device 402A to be repositioned. For example, in some embodiments, the gripping mechanism 424 can be released to allow the drive device 402A to slide along the elongated shaft 410 to a new position, at which the gripping mechanism 424 can be reengaged.

In some embodiments, the gripping mechanism 424 comprises a clamping device as shown, for example, in FIGS. 27D and 27E below. The gripping mechanism 424 can include an actuator for actuating the gripping mechanism 424. The actuator can comprise, for example, one or more buttons or compressible handles. In some embodiments, the gripping mechanism 424 defaults to the engaged position, such that, when the actuator is not pressed, the gripping mechanism 424 engages the elongated shaft 410, and when the actuator is pressed, the gripping mechanism 424 releases the elongated shaft 410. In other embodiments, the reverse may be true. For example, in some embodiments, the gripping mechanism 424 defaults to the disengaged position, such that, when the actuator is not pressed, the gripping mechanism 424 is not engaged with the elongated shaft 410, and when the actuator is pressed, the gripping mechanism 424 engages the elongated shaft 410.

When the gripping mechanism 424 is engaged with the elongated shaft 410, the physician, holding the drive device 402A, can manually manipulate the elongated shaft 410. For example, in some embodiments, the physician can insert the elongated shaft 410 by pushing the drive device 402A forward. Similarly, in some embodiments, the physician can retract the elongated shaft 410 by pulling the drive device 402A backwards. In some embodiments, the physician can also roll the elongated shaft 410 by rolling the drive device 402A. Such manual manipulation of the elongated shaft 410 using the drive device 402A is shown, for example, in FIGS. 23A and 23B.

In some embodiments, the gripping mechanism 424 can include an insertion mechanism 424 and/or a roll mechanism 428, although these features need not be included in all embodiments. In some embodiments, the insertion mechanism 424 is configured to drive insertion and/or retraction of the elongated shaft 410 relative to the drive device 402A. For example, the insertion mechanism 424 can be used to drive insertion and/or retraction of the elongated shaft 410 while the drive device 402A remains relatively stationary. For example, in some embodiments, the insertion mechanism 424 comprises one or more motor driven wheels that engage the elongated shaft 410 in a direction aligned with the longitudinal axis of the elongated shaft 410. The wheels can be rotated to drive elongated shaft 410 forward or backward. In other embodiments, the insertion mechanism 424 can comprise other structures for driving insertion.

The roll mechanism 428 can be configured to drive roll of the elongated shaft 410 about its longitudinal axis and relative to the drive device 402A. For example, the roll mechanism 428 can be used to drive roll of the elongated shaft 410 while the drive device 402A remains relatively stationary. In some embodiments, the roll mechanism 428 comprises one or more motor driven wheels that engage the elongated shaft 410 in a circumferential direction of the elongated shaft 410. The wheels can be rotated to roll elongated shaft 410 about its longitudinal axis in clockwise and/or counterclockwise directions. In other embodiments, the roll mechanism 428 can comprise other structures for driving roll.

In the illustrated embodiment of FIG. 26A, the drive device 402A includes an articulation input 430. As noted previously, the articulation input 430 is configured to receive user inputs of commanded articulation for the physician. The articulation input 430 may also be configured to receive user inputs of commanded insertion and/or roll to be performed by the insertion mechanism 424 and/or the roll mechanism 424, if either of these mechanisms is present. In some embodiments, the articulation input 430 can comprise a joystick, such as in the illustrated example of FIGS. 27A-27C. In other embodiments, the articulation input 430 can take other forms, such as buttons, dials, thumbwheels, touch interfaces, etc. In some embodiments, the articulation input 430 is configured to receive user input of commanded articulation for two-way deflection control (e.g., up and down). In some embodiments, the articulation input 430 is configured to receive user input of commanded articulation for four-way deflection control (e.g., up, down, left, and right). The articulation inputs can be provided with respect to various control schemes, such as the instrument-based control scheme described in FIG. 29A, the gravity-based control scheme described in FIG. 29B, or others.

The drive device 402A may also include communications circuit 432. The communications circuit 432 can be configured to transmit signals indicative of user inputs of commanded articulation provided by the articulation input 430 to the communications circuit 416 of the instrument drive mechanism 406 as described above. In some embodiments, the communications circuit 432 can be configured for wireless communication. For example, the communications circuit 432 can be a WLAN circuit, a PAN circuit, a WWAN circuit, or any other type of wireless circuit. In other embodiments, the communications circuit 432 can be configured for wired communication. Communication between the instrument drive mechanism 406 and the drive device 402A through the communications circuit 432 can be direct or indirect. Indirect communication may pass through one or more additional components of the medical system and/or one or more computer or communications networks.

In some embodiments, the drive device 402A is configured for single-handed use as shown in FIGS. 23A and 23B because the components are included in a single unit or handle as illustrated.

FIG. 26B, illustrates a block diagram of a second embodiment of the drive device 402B. In contrast with the drive device 402A, the components of the drive device 402B are divided into two separate units. For example, as illustrated, the gripping mechanism 424 can be formed as a first unit or handle, and the articulation input 430 can be formed as a second unit or pendant. Each of these components may perform functions similar to those described above with reference to the drive device 402A, except that the drive device 402B will generally require two hands to operate. For example, the gripping mechanism 424 can be operated with a first hand and the articulation input 430 can be operated with a second hand. This may be similar to example depicted in FIG. 24, except that FIG. 24 does not show the gripping mechanism 424 (rather, the physician holds the elongated shaft of the medical instrument directly in FIG. 22C).

Because the gripping mechanism 424 and the articulation input 430 are embodied in separated devices, each may include a communications circuit 432A, 432B to allow for communications with each other and other components of the medical system 400. In some embodiments, if the gripping mechanism 424 does not include the insertion mechanism 426 and the roll mechanism 428, communications circuit 432A may be omitted.

FIG. 26C, illustrates a block diagram of a third embodiment of the drive device 402C. In this embodiment, the drive device 402C includes a single unit or pendant that includes the articulation input 430. As before, the articulation input can include a communications circuit 432 for transmitting received user inputs of commanded articulation to the instrument drive mechanism 406. Example use of the drive device 402C is shown in FIG. 24. As shown, the user provides articulation input 430 with one hand while holding the elongated shaft of the medical instrument directly with another hand.

In another embodiment, the articulation input could be integrated into the instrument drive mechanism 406.

Figure 27B:
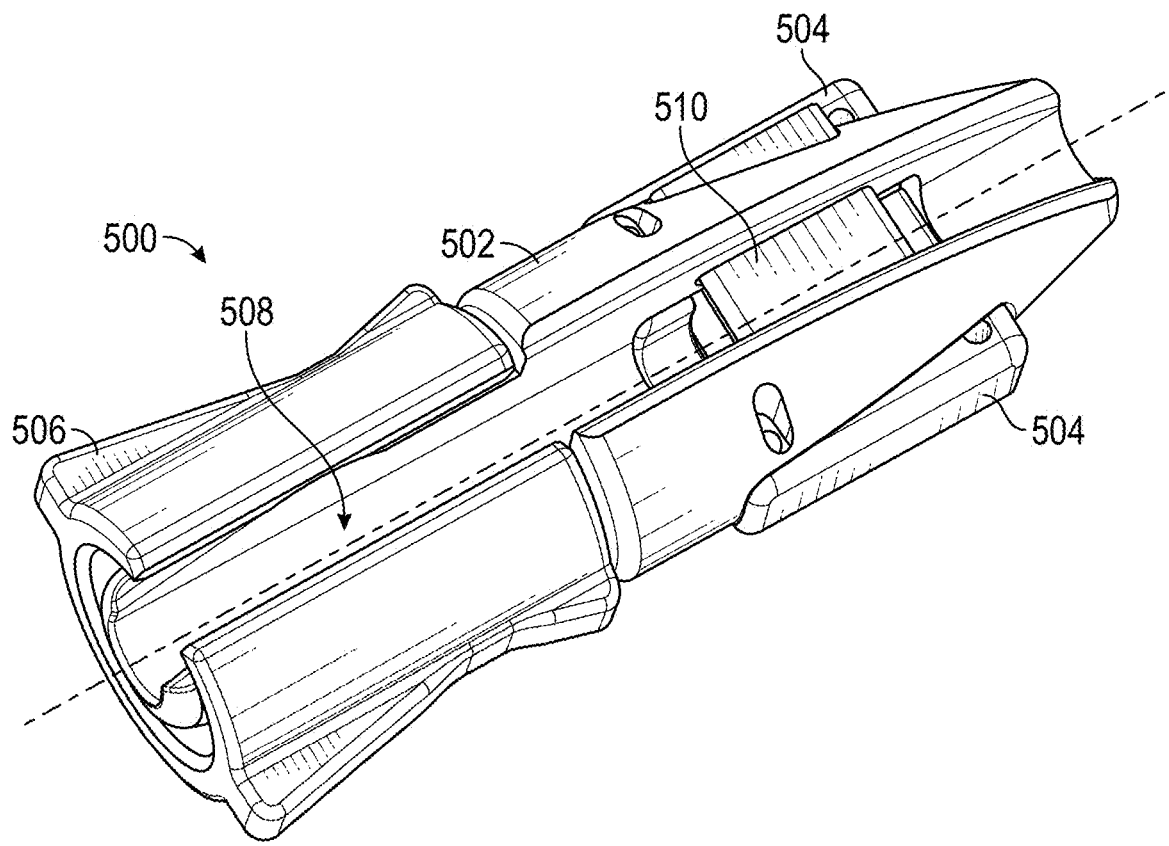
Figure 27D:
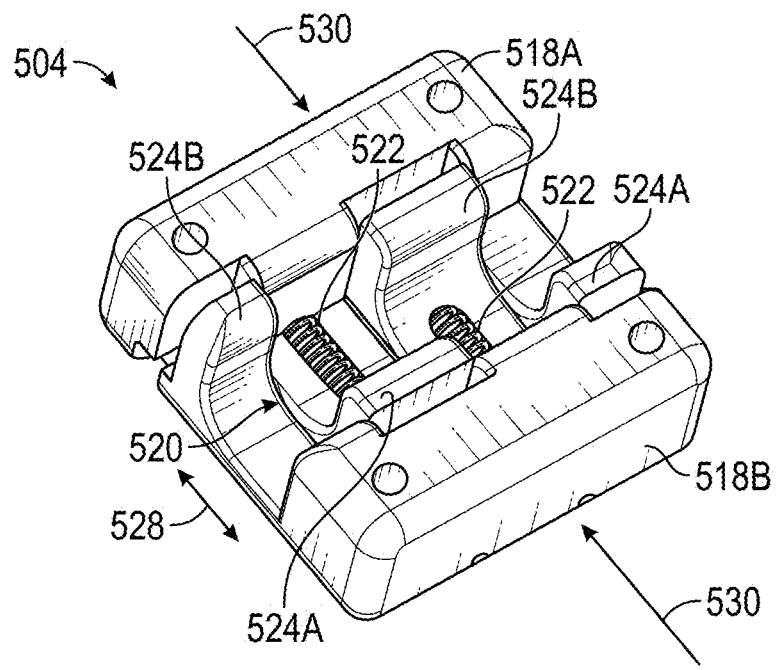
FIGS. 27D and 27E are top and bottom isometric views, respectively, of an embodiment of a gripping mechanism of the drive device of FIG. 27A.
Figure 27E:
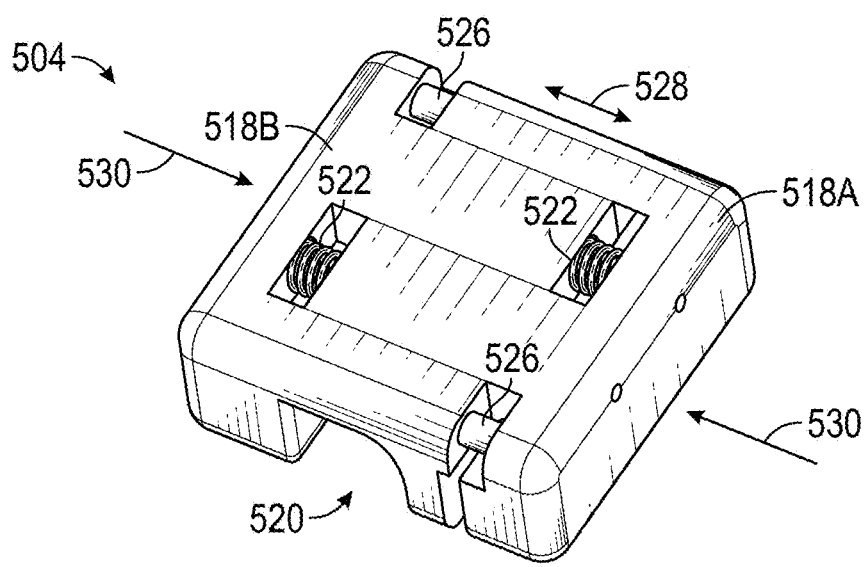
Figure 28:
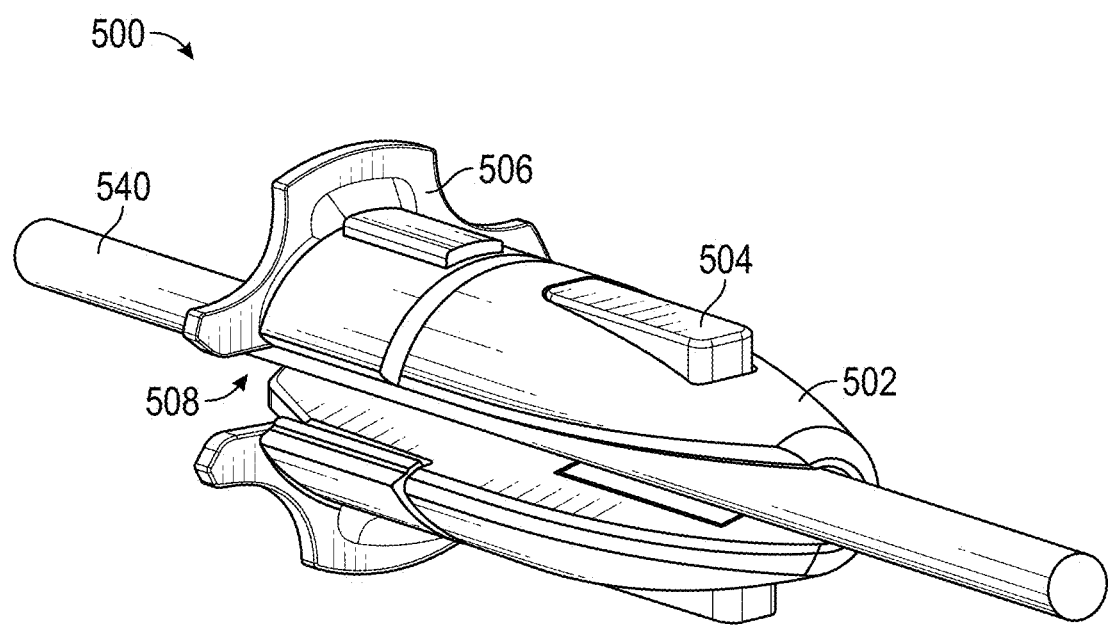
FIG. 28 illustrates the drive device of FIG. 27A positioned on an elongated shaft of a medical instrument, according to one embodiment.

FIGS. 27A and 27B are top and bottom isometric views, respectively, of an embodiment of a drive device 500 for use with robotic medical systems as described herein. The drive device 500 may be, for example, the drive device(s) 402 or the drive device 304 previously described. As illustrated in FIG. 27A, the drive device 500 may include handle 502. The handle 502 may extend along a longitudinal axis as shown. The drive device 500 may include a gripping mechanism 504 positioned on or in the handle 502. As described before, the gripping mechanism 504 can be configured to selectively engage the elongated shaft of a medical instrument. In the illustrated embodiment, the gripping mechanism 504 extends through the handle 502 such that the gripping mechanism 504 can be actuated by pressing the on the exposed portions, which can serve as buttons. The gripping mechanism 504 is shown alone in FIGS. 27D and 27E, which are described below.

In the illustrated embodiment, the drive device 500 also includes an articulation input 506. In the illustrated embodiment, the articulation input 506 comprises a joystick that is positioned on the front of the handle 502. The joystick can be moved relative to the handle 502 in the directions indicated with arrows to provide user input indicative or articulation.

As best seen in FIG. 27B, the drive device 500 can include a channel 506 formed into a side thereof as shown. The channel 506 can extend along the longitudinal axis. The channel 506 can be configured to receive the elongated shaft of a medical instrument as shown in FIG. 28. A portion of the gripping mechanism 504 can be positioned within the channel 508 and configured to selectively engage with the elongated shaft.

In some embodiments, the drive device 500 also includes a channel cover or lock 510 that is configured to retain the elongated shaft within the channel, but that does not prevent the drive device 500 from sliding along the elongated shaft. In some embodiments, the channel lock can be opened to allow the drive device 500 to be positioned on the elongated shaft and then closed around the elongated shaft to retain the elongated shaft in the channel 506. In the illustrated embodiment, the channel lock 510 is shown in the closed position.

Figure 27C:
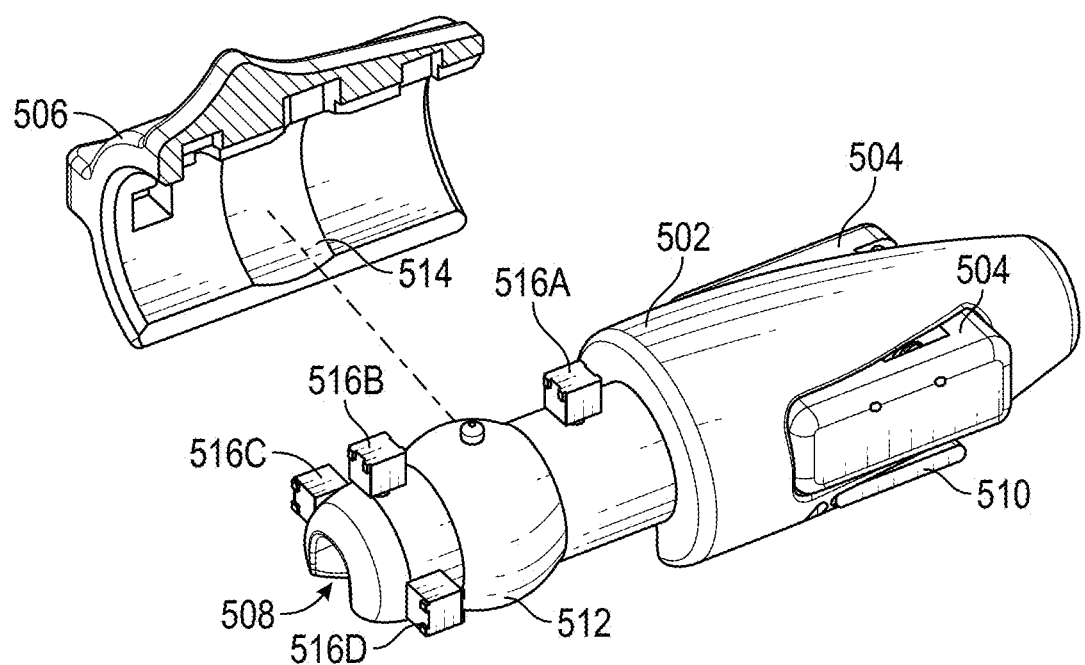
FIG. 27C illustrates a partially exploded perspective view of the drive device of FIG. 27A. A cross-sectional view of an articulation input handle of the drive device is shown to visualize internal features of the articulation input handle.

FIG. 27C illustrates a partially exploded perspective view of the drive device 500. The articulation input 506 of the drive device 500 is shown with a cross-sectional view to visualize internal features thereof. As illustrated, the articulation input 506 and handle 502 are configured to form a ball joint that permits motion of the articulation input 506 relative to the handle 502. For example, a proximal portion of the handle 502 forms a ball portion 512 that is configured to contact a corresponding socket portion 514 of the articulation input 506.

Also illustrated in FIG. 27C, the drive device 500 can include load cells 516 positioned between the handle 502 and the articulation input 506. The load cells 516 can be configured to detect relative motion between the articulation input 506 and the handle 502 that is indicative of the commanded user inputs. In the illustrated example, the load cell 516A is used to detect up, the load cell 516B is used to detect down, the load cell 516C is used to detect right, and the load cell 516D is used to detect left. Other arrangements are possible.

FIGS. 27D and 27E are top and bottom isometric views, respectively, of an embodiment of the gripping mechanism 504 of the drive device of 500. In the illustrated embodiment, the gripping mechanism 504 includes first and second bodies 518A, 518B. Each of the bodies 518A, 518B include distal flanges 524A, 524B to form a clamping groove 520 therebetween. Springs 522 provide a force that biases the bodies 518A, 518B away from each other in the direction of the arrows 528, which creates a clamping force between the distal flanges 524A4, 524B. To release the clamping force, the bodies 518A, 518B can be pressed towards each other in the direction of the arrows 530. As best seen in FIG. 27E, the first and second bodies 518A, 518B can be mounted on rails 526 to maintain alignment therebetween.

FIG. 28 illustrates the drive device 500 of FIG. 27 positioned on an elongated shaft 540 of a medical instrument. As shown, the elongated shaft 540 is positioned within the groove 508. In some embodiments, a physician can hold the handle 502 with a single hand and actuate both the gripping mechanism 504 and the articulation input 506 to provide manual control for the medical instrument as described above.

B. Example Control Schemes for Driving Medical Instruments

FIG. 29A illustrates a first example control scheme 600A for a robotic medical system in which articulation inputs for causing articulation of the elongated shaft 602 of a medical instrument are provided in an instrument-based orientation. In some embodiments, the articulation inputs can be those provided with the articulation input 430 of the drive device 402 during manual control of the medical instrument. The control scheme 600A can also be used during robotic control of the medical instrument.

In this example, the elongated shaft 602 is configured for four-way deflection in up, down, left, and right directions. In the control scheme 600A, the four-way deflection directions are locked with respect to the orientation of the elongated shaft. For example, point 604 in FIG. 29A represents a point on the "top" of the elongated shaft 602. As the elongated shaft 602 is navigated through the body, the point 604 may end up facing in many different directions. For example, the top of point 604 may not be aligned with the direction of gravity. Regardless, in the control scheme 600A, the four-way deflection directions are locked with respect to the orientation of the elongated shaft. That is, deflection in the up direction is aligned with the point 604 as shown, irrespective of the direction of gravity. The other articulation directions (left, right, and down) can be orthogonally positioned with respect to the point 604 as shown. Thus, the control scheme 600A is considered an instrument-based orientation. As the elongated shaft 602 rolls, the deflection directions roll with it.

Another way for visualizing the control scheme 600A is with respect to the vision of the medical instrument. The medical instrument may include a vision or camera system that is positioned on the distal end of the elongated shaft 602. The camera system can be rotationally fixed with respect to the elongated shaft such that when the elongated shaft 602 rolls, the camera system rolls with it. In the control scheme 600A, the deflection directions can be aligned with the output 606 of the camera system. For example, deflection in the up direction causes deflection in an up direction relative to the output 606 of the camera system regardless of the roll orientation of the elongated shaft 602 or the direction of gravity.

FIG. 29B illustrates a second example control scheme 600B for a robotic medical system in which articulation inputs for causing articulation of the elongated shaft of a medical instrument are provided in a gravity-based orientation. In some embodiments, the articulation inputs can be those provided with the articulation input 430 of the drive device 402 during manual control of the medical instrument. The control scheme 600B can also be used during robotic control of the medical instrument.

Again, in this example, the elongated shaft 602 is configured for four-way deflection in up, down, left, and right directions. In the control scheme 600B, however, the four-way deflection directions are locked with respect to the orientation of gravity. That is deflection in the down direction causes deflection in the direction of gravity. The remaining deflection directions are orthogonally oriented with respect to the down direction (and the gravity direction) as illustrated.

In some embodiments, the system may be configured automatically roll the elongated shaft 602 such that the point 604 on the top of the elongated shaft 602 is always positioned in the up direction. Thus, the control scheme 600A is considered a gravity-based orientation. The elongated shaft 602 automatically rolls such that the deflection directions are always oriented with respect to gravity. Another way for visualizing the control scheme 600B is with respect to the vision of the medical instrument. As shown, the output 606 of the camera system of the medical instruments are aligned with respect to gravity.

C. Example Methods for Driving Medical Instruments

Figure 30:
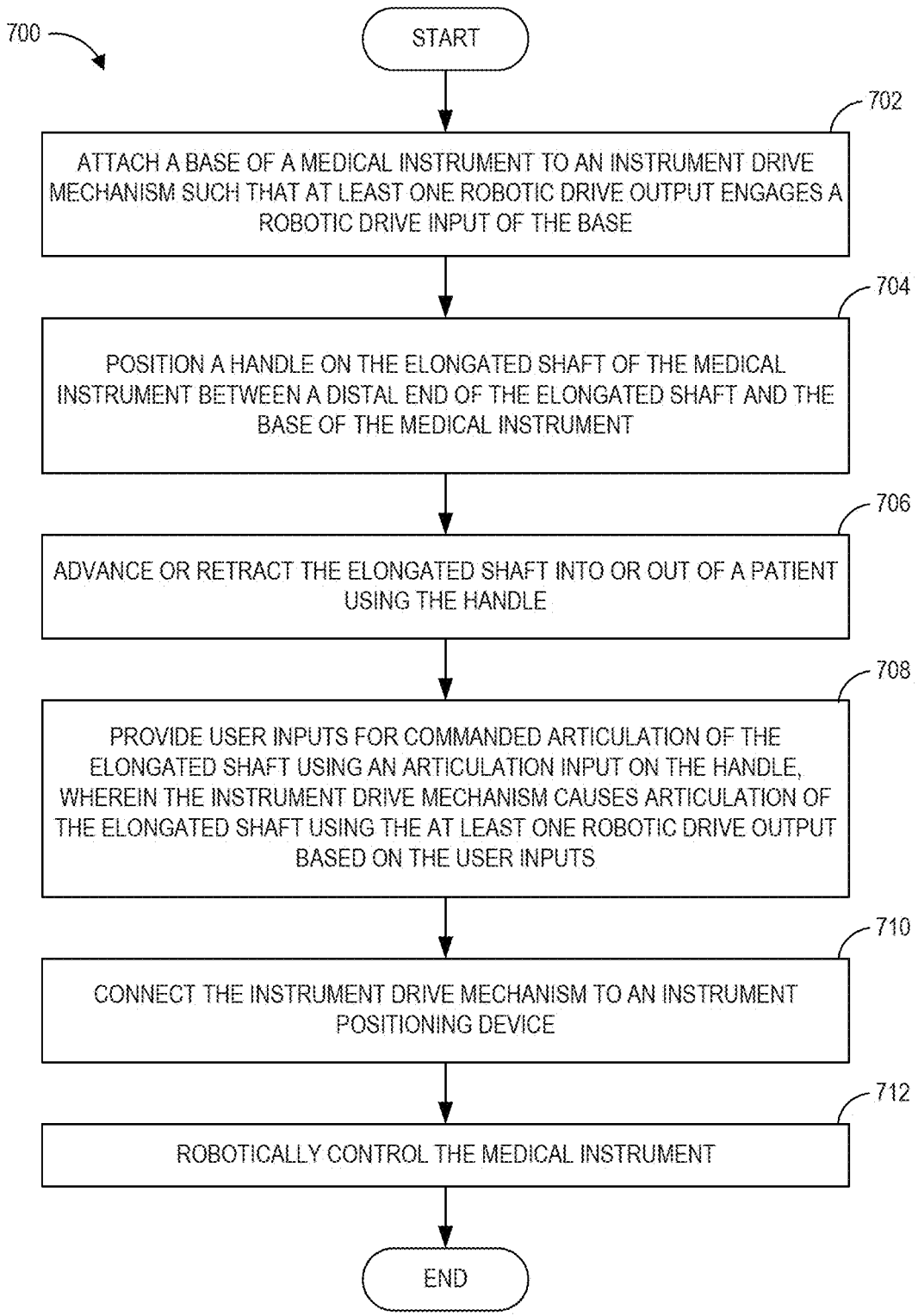
FIG. 30 is a flowchart depicting an example method for manually and robotically driving a medical instrument.

FIG. 30 is a flowchart depicting an example method 700 for manually and robotically controlling and/or driving a medical instrument. The method 700 can be implemented, for example, with the robotic medical systems 300, 400 described above, or others. In some embodiments, the method 700 advantageously provides for both manual and robotic control of the medical instrument during a procedures, such that either manual or robotic control can be used for various portions of the procedures as best suited for those particular portions.

The method 700 begins at block 702, at which a base of a medical instrument is attached to an instrument drive mechanism such that at least one robotic drive output engages a robotic drive input of the base. In some embodiments, the medical instrument is an endoscope. In some embodiments, the medical instrument is robotically controllable though one or more drive inputs in the base of the medical instruments. In some embodiments, drive outputs of the instrument drive mechanism engage the drive inputs to actuate the medical instrument.

In some embodiments, the instrument drive mechanism comprises a dockable instrument drive mechanism. In some embodiments, at block 702 the instrument drive mechanism is undocked, as shown, for example, in FIG. 22A.

At block 704, the method 700 may involve positioning a handle on the elongated shaft of the medical instrument between a distal end of the elongated shaft and the base of the medical instrument. The handle may comprise, for example, a drive device as described above. In some embodiments, positioning the handle on the elongated shaft may comprise engaging a gripping mechanism of the handle to the elongated shaft to fixedly attach the handle to the elongated shaft. In some embodiments, the handle may be omitted, and block 704 may involve gripping the elongated shaft directly by hand.

The method 700 can then move to block 706, at which the elongated shaft is advanced or retracted into or out of a patient using the handle, or, if the handle is omitted, by hand. In some embodiments, advancing or retracting the elongated shaft into or out of the patient using the handle comprises moving the handle toward or away from the patient while the gripping mechanism is engaged.

In some embodiments, advancing or retracting the elongated shaft comprises activing an insertion mechanism of the handle. In some embodiments, activating the insertion mechanism of the handle can comprise providing a user input indicative of insertion using an articulation input of the handle.

In some embodiments, advancing or retracing the elongated shaft using the handle can further involve repositioning the handle on the elongated shaft. Repositioning the handle on the elongated shaft can involve disengaging the gripping mechanism, sliding the handle along the elongated shaft, and reengaging the gripping mechanism to fixedly attach the handle to the elongated shaft.

In some embodiments, the method 700 may additionally involve rolling the elongated shaft using the handle, or, if the handle is omitted, by hand. In some embodiments, rolling the elongated shaft using the handle can comprise rolling the handle. In some embodiments, rolling the elongated shaft using the handle can comprise activing a roll mechanism of the handle. In some embodiments, activating the roll mechanism of the handle can comprise providing a user input indicative of roll using an articulation input of the handle.

At block 708, the method 700 involves providing user inputs for commanded articulation of the elongated shaft using an articulation input of the handle. The user inputs for commanded articulation can be transmitted to the instrument drive mechanism to articulation of the elongated shaft using the at least one robotic drive output based on the user inputs. In some embodiments, blocks 706 and 708 are performed using a single hand. In some embodiments, blocks 706 and 708 are performed using two hands. In some embodiments, blocks 706 and 708 are performed simultaneously.

Next, at block 710, the method 700 involves connecting the instrument drive mechanism to an instrument positioning device. The instrument positioning device may comprise a robotic arm, linear drive mechanism, or other instrument positioning device. Connecting the instrument drive mechanism to the instrument positioning device can comprise attaching a connector of the instrument drive mechanism to a corresponding connector of the instrument positioning device.

Finally, at block 712, the method 700 involves robotically controlling the medical instrument. Robotically controlling the medical instrument can involve advancing or retracting the elongated shaft with the robotic arm.

The method 700 can be configured for performing various medical procedures, such as colonoscopy, uroscopy, ureteroscopy, gastroscopy, bronchoscopy, etc. In some embodiments, the method 700 can be performed for other medical procedures, such as other endoscopic, laparoscopic, or open procedures.

D. Advantages

In some embodiments, the robotic systems, devices, and methods discussed above can provide one or more notable advantages over other systems. For example, in some embodiments, they can offer intuitive and increased tactile torque and insertion feedback over traditional insertion methods. This can be because, as discussed above, the systems, devices, and methods can permit a more ergonomic body positioning for the user during use. In some embodiments, the systems, devices, and methods can offer one to one torqueing of elongated shaft of the medical instrument. In some embodiments, the systems, devices and methods can offer a two handed tactile feedback loop (e.g., with one hand on elongated shaft and one hand on patient at point of insertion). In some embodiments, they can offer a reduced range of motion for the instrument positioning devices. For example, they can allow the instrument to be inserted manually and then transitioned to robotic control, which may use the instrument positioning devices (e.g., robotic arms). In some embodiments, the devices, systems, and methods can allow for manual insertion of robotically-controlled medical instruments. In some embodiments, the devices, systems, and methods can offer reduced buckling through quick clamping of handle. For example, a user can reposition the handle close to the insertion point to reduce the likelihood of buckling. In some embodiments, use of the systems, methods, and devices can offer higher insertion speeds through increased user confidence, higher insertion speeds through lack of need for cumbersome insertion guide tube, and/or allow the physician to stabilize patient during scope insertion. Additionally, in some embodiments, the systems, methods, and devices can offer fly by wire elongated shaft articulation, for example, through wireless communication. Due to the ergonomic use of the systems, devices, and methods, they can offer ease of use and minimizes carpel tunnel syndrome (e.g., through higher torque mechanical advantage) compared to other devices.

3. Implementing Systems and Terminology

Implementations disclosed herein provide systems, methods and apparatus for driving medical instruments, and more particularly, to devices, systems, and methods for manually and robotically driving medical instruments, such as endoscopes, for example.

It should be noted that the terms "couple," "coupling," "coupled" or other variations of the word couple as used herein may indicate either an indirect connection or a direct connection. For example, if a first component is "coupled" to a second component, the first component may be either indirectly connected to the second component via another component or directly connected to the second component.

The phrases referencing specific computer-implemented processes and functions described herein may be stored as one or more instructions on a processor-readable or computer-readable medium. The term "computer-readable medium" refers to any available medium that can be accessed by a computer or processor. By way of example, and not limitation, such a medium may comprise random access memory (RAM), read-only memory (ROM), electrically erasable programmable read-only memory (EEPROM), flash memory, compact disc read-only memory (CD-ROM) or other optical disk storage, magnetic disk storage or other magnetic storage devices, or any other medium that can be used to store desired program code in the form of instructions or data structures and that can be accessed by a computer. It should be noted that a computer-readable medium may be tangible and non-transitory. As used herein, the term "code" may refer to software, instructions, code or data that is/are executable by a computing device or processor.

The methods disclosed herein comprise one or more steps or actions for achieving the described method. The method steps and/or actions may be interchanged with one another without departing from the scope of the claims. In other words, unless a specific order of steps or actions is required for proper operation of the method that is being described, the order and/or use of specific steps and/or actions may be modified without departing from the scope of the claims.

As used herein, the term "plurality" denotes two or more. For example, a plurality of components indicates two or more components. The term "determining" encompasses a wide variety of actions and, therefore, "determining" can include calculating, computing, processing, deriving, investigating, looking up (e.g., looking up in a table, a database or another data structure), ascertaining and the like. Also, "determining" can include receiving (e.g., receiving information), accessing (e.g., accessing data in a memory) and the like. Also, "determining" can include resolving, selecting, choosing, establishing and the like.

The phrase "based on" does not mean "based only on," unless expressly specified otherwise. In other words, the phrase "based on" describes both "based only on" and "based at least on."

The previous description of the disclosed implementations is provided to enable any person skilled in the art to make or use the present invention. Various modifications to these implementations will be readily apparent to those skilled in the art, and the generic principles defined herein may be applied to other implementations without departing from the scope of the invention. For example, it will be appreciated that one of ordinary skill in the art will be able to employ a number corresponding alternative and equivalent structural details, such as equivalent ways of fastening, mounting, coupling, or engaging tool components, equivalent mechanisms for producing particular actuation motions, and equivalent mechanisms for delivering electrical energy. Thus, the present invention is not intended to be limited to the implementations shown herein but is to be accorded the widest scope consistent with the principles and novel features disclosed herein.

What is claimed is:

1. A robotic system comprising:
   a medical instrument comprising a base and an elongated shaft, the base comprising drive inputs configured to be actuated to articulate the medical instrument;
   an instrument drive mechanism coupled to the base of the medical instrument, the instrument drive mechanism comprising drive outputs driven by actuators in the instrument drive mechanism, the drive outputs engaged with and configured to actuate the drive inputs of the base of the medical instrument, the instrument drive mechanism further comprising a first connector; and
   a robotic arm comprising a second connector configured to selectively couple to the first connector of the instrument drive mechanism, wherein:
      in a first configuration, the first connector is engaged with the second connector such that the instrument drive mechanism and medical instrument are coupled to the robotic arm, and
      in a second configuration, the first connector is disengaged from the second connector such that the instrument drive mechanism and medical instrument are uncoupled from the robotic arm,
   wherein the instrument drive mechanism is configured to cause articulation of the elongated shaft in the second configuration.

2. The system of claim 1, wherein, in the first configuration, the robotic arm is configured to move the instrument drive mechanism and the medical instrument.

3. The system of claim 2, wherein, in the second configuration the elongated shaft can be manually inserted into a patient during a medical procedure.

4. The system of claim 3, further comprising a device for driving the medical instrument, the device comprising:
   an articulation input configured to receive user inputs of commanded articulation of the elongated shaft; and
   a communications circuit positioned in the device and configured to transmit user inputs received at the articulation input to the instrument drive mechanism coupled to the medical instrument, the instrument drive mechanism configured to cause articulation of the elongated shaft based on the transmitted user inputs.

5. The system of claim 4, wherein the device further comprises:
   a handle configured to receive the elongated shaft of the medical instrument; and
   a gripping mechanism positioned in the handle for selectively engaging the elongated shaft, the gripping mechanism configured to fixedly attach to the elongated shaft when engaged and to allow the handle to slide along the elongated shaft when disengaged.

6. The system of claim 5, wherein the articulation input is positioned on the handle.

7. The system of claim 5, wherein:
   the handle comprises a channel configured to receive the elongated shaft; and
   the gripping mechanism comprises:
      a clamping mechanism positioned within the channel and configured to clamp onto the elongated shaft; and
      an actuator configured to release the clamping mechanism such that the elongated shaft is slidable within the channel when the actuator is actuated.

8. The system of claim 5, further comprising an insertion mechanism for driving insertion of the elongated shaft relative to the handle.

9. The system of claim 5, further comprising a roll mechanism for driving roll of the elongated shaft.

10. The system of claim 4, wherein the device is configured to automatically roll the elongated shaft using a roll mechanism to retain a gravity based orientation of the medical instrument.

11. The system of claim 4, wherein the device is configured to provide on-axis navigation such that user inputs of commanded articulation cause articulation of the elongated shaft in a gravity based orientation irrespective of roll of the elongated shaft.

12. The system of claim 4, wherein the device is configured to allow a user to advance, retract, and articulate the elongated shaft of the medical instrument with a single hand.

13. A method for driving a medical instrument, the method comprising:
   attaching a medical instrument to an instrument drive mechanism, wherein:
      the medical instrument comprises a base and an elongated shaft, the base comprising drive inputs configured to be actuated to articulate the medical instrument, and
      the instrument drive mechanism comprises drive outputs driven by actuators, the drive outputs configured to engage with and actuate the inputs of base of the medical instrument, the instrument drive mechanism further comprising a first connector;
   in a first configuration with the first connector of the instrument drive mechanism disengaged from a second connector of a robotic arm such that the instrument drive mechanism and medical instrument are uncoupled from the robotic arm, articulating the medical instrument using the instrument drive mechanism using the actuators of the instrument drive mechanism;
   attaching the first connector of the instrument drive mechanism to the second connector of the robotic arm to achieve a second configuration in which the instrument drive mechanism and medical instrument are coupled to the robotic arm; and
   in the second configuration, articulating the medical instrument with the instrument drive mechanism.

14. The method of claim 13, further comprising, in the second configuration, adjusting a position of the medical instrument using the robotic arm.

15. The method of claim 13, further comprising, in the first configuration inserting the elongated shaft of the medical instrument into a patient.

16. The method of claim 15, wherein inserting the elongated shaft of the medical instrument into the patient is performed manually.

17. The method of claim 15, wherein inserting the elongated shaft of the medical instrument into the patient comprises:
   positioning a handle on the elongated shaft of the medical instrument between a distal end of the elongated shaft and the base of the medical instrument;
   advancing or retracting the elongated shaft into or out of a patient using the handle; and
   providing user inputs for commanded articulation of the elongated shaft using an articulation input on the handle, wherein the instrument drive mechanism causes articulation of the elongated shaft based on the user inputs.

18. The method of claim 17, wherein positioning the handle on the elongated shaft comprises:
   disengaging a gripping mechanism to slide the handle along the elongated shaft; and
   engaging the gripping mechanism to fixedly attach the handle to the elongated shaft.

19. The method of claim 17, wherein advancing or retracting the elongated shaft into or out of the patient using the handle comprises moving the handle toward or away from the patient while a gripping mechanism is engaged.

* * * * *